(12) United States Patent (10) Patent No.: US 10,040,849 B2
Gearing (45) Date of Patent: Aug. 7, 2018

(54) CANINIZED ANTI-NERVE GROWTH FACTOR ANTIBODIES

(75) Inventor: David Gearing, Southbank, Victoria (AU)

(73) Assignee: NEXVET AUSTRALIA PTY LTD, Melbourne, Victoria (AU)

(*) Notice: Subject to any disclaimer, the term of this patent is extended or adjusted under 35 U.S.C. 154(b) by 427 days.

(21) Appl. No.: 14/115,784

(22) PCT Filed: May 8, 2012

(86) PCT No.: PCT/GB2012/051002
§ 371 (c)(1),
(2), (4) Date: Aug. 21, 2014

(87) PCT Pub. No.: WO2012/153121
PCT Pub. Date: Nov. 15, 2012

(65) Prior Publication Data
US 2015/0017154 A1 Jan. 15, 2015

Related U.S. Application Data

(60) Provisional application No. 61/483,481, filed on May 6, 2011, provisional application No. 61/531,439, filed on Sep. 6, 2011.

(30) Foreign Application Priority Data

Aug. 29, 2011 (GB) .................................. 1114858.2

(51) Int. Cl.
*C07K 16/22* (2006.01)
*C07K 16/46* (2006.01)
*A61K 39/395* (2006.01)
*A61K 45/06* (2006.01)

(52) U.S. Cl.
CPC .......... *C07K 16/22* (2013.01); *A61K 39/3955* (2013.01); *A61K 45/06* (2013.01); *C07K 16/467* (2013.01); *C07K 2317/24* (2013.01); *C07K 2317/41* (2013.01); *C07K 2317/71* (2013.01); *C07K 2317/72* (2013.01); *C07K 2317/734* (2013.01)

(58) Field of Classification Search
None
See application file for complete search history.

(56) References Cited

U.S. PATENT DOCUMENTS

2013/0330348 A1 12/2013 Lacy et al.
2016/0272701 A1 9/2016 Gearing

FOREIGN PATENT DOCUMENTS

| EP | 2 138 512 B1 | 12/2009 |
|---|---|---|
| WO | WO 93/16192 | 8/1993 |
| WO | WO-01/77332 | 10/2001 |
| WO | WO-03/002607 A1 | 1/2003 |
| WO | WO-03/060080 | 7/2003 |
| WO | WO-2004/020579 A2 | 3/2004 |
| WO | WO-2005/061540 A2 | 7/2005 |
| WO | WO-2006/131951 A1 | 12/2006 |
| WO | WO-2010/027488 A2 | 3/2010 |
| WO | WO-2010/110838 A2 | 9/2010 |
| WO | WO-2010/117448 A2 | 10/2010 |
| WO | WO-2012/024650 A2 | 2/2012 |

OTHER PUBLICATIONS

Brorson et al., "Mutational Analysis of Avidity and Fine Specificity of Anti-Levan Antibodies", J. Immunol., 163:6694-6701, Dec. 1999.
Brummell et al., "Probing the combining site of anti-carbohydrate antibody by saturation-mutagenesis: role of the heavy-chain CDR3 residues", Biochemistry, 32:1180-1187, Feb. 1993 (Abstract).
Burks et al., "In vitro scanning saturation mutagenesis of an antibody binding pocket", Proc. Natl. Acad. Sci. USA, 94:412-417, Jan. 1997.
Casset et al, "A peptide mimetic of an anti-CD4 monoclonal antibody by rational design", Biochemical and Biophysical Research Communications, 307:198-205, Jul. 2003.
Chen et al., "Selection and Analysis of an Optimized Anti-VEGF Antibody: Crystal Structure of an Affinity-matured Fab in Complex with Antigen", J. Mol. Biol., 293:865-881, Nov. 1999.
Colman, "Effects of amino acid sequence changes on antibody-antigen interactions", Research in Immunol., 145:33-36, Jan. 1994.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody", J. Immunol., 169:3076-3084, Sep. 2002.
Holm et al., "Functional mapping and single chain construction of the anti-cytokeratin 8 monoclonal antibody TS1", Molecular Immunology, 44:1075-1084, Feb. 2007.
Jang et al., "The structural basis for DNA binding by an anti-DNA autoantibody", Molecular Immunology, 35:1207-1217, Dec. 1998.
Kobayashi et al., "Tryptophan H33 plays an important role in pyrimidine (6-4) pyrimidone photoproduct binding by a high-affinity antibody", Protein Engineering, 12:879-884, Oct. 1999.
MacCallum et al., "Antibody-antigen Interactions: Contact Analysis and Binding Site Topography", J. Mol. Biol., 262:732-745, Oct. 1996.
Office action dated Jun. 9, 2015 issued in U.S. Appl. No. 14/115,787.
Rudikoff et al., "Single amino acid substitution altering antigen-binding specificity", Proc. Natl. Acad. Sci. USA, 79:1979-1983, Mar. 1982.

(Continued)

*Primary Examiner* — Robert C Hayes
(74) *Attorney, Agent, or Firm* — Foley & Lardner LLP

(57) ABSTRACT

A method of preparing an antibody suitable for use in a canine is provided. Also provided are caninized antibodies which specifically bind to canine neuronal growth factor (NGF) and neutralize the ability of canine NGF to bind to the p75 or TrkA canine NGF receptor. The invention extends to nucleic acids encoding same and to methods of treating pain and arthritis in a canine using said antibodies and/or nucleic acids.

1 Claim, 23 Drawing Sheets

(56) References Cited

OTHER PUBLICATIONS

Vajdos et al., "Comprehensive Functional Maps of the Antigen-binding Site of an Anti-ErbB2 Antibody Obtained with Shotgun Scanning Mutagenesis", J. Mol. Biol., 320:415-428, Jul. 2002.
Wu et al, "Humanization of a Murine Antibody by Simultaneous Optimization of Framework and CDR Residues", J. Mol. Biol. 294:151-162, Nov. 1999.
U.S. Appl. No. 14/115,772, filed Feb. 5, 2014, David Gearing.
U.S. Appl. No. 14/115,779, filed Feb. 6, 2014, David Gearing.
U.S. Appl. No. 14/115,787, filed Feb. 11, 2014, David Gearing.
U.S. Appl. No. 14/241,616, filed Feb. 27, 2014, David Gearing.
U.S. Appl. No. 14/342,943, filed Mar. 5, 2014, David Gearing.
Abe et al., "Protective Role of Nerve Growth Factor Against Postischemic Dysfunction of Sympathetic Coronary Innervation," Circulation, vol. 95, No. 1, Jan. 7, 1997.
Cattaneo et al., "Humanized alpha Dll antibody heavy chain variable region Seq ID No. 17," Database Accension No. AEB12537, Sep. 8, 2005.
Cattaneo, "Method for the humanization of antibodies and humanized antibodies thereby obtained Patent No. WO2005/061540-A2," Database Accesion No. CS126835, Jul. 20, 2005.
Covaceuszach et al., "Dissecting NGF Interactions with TrkA and p75 Receptors by Structural and Functional Studies of an Anti-NGF Neutralizing Antibody," Journal of Molecular Biology, Academic Press, vol. 381, No. 4, Sep. 12, 2008.
International Search Report dated Aug. 1, 2012 issued in connection with International Application No. PCT/GB2012/051008.
International Search Report dated Aug. 20, 2012 issued in connection with International Application No. PCT/GB2012/051004.
International Search Report dated Aug. 30, 2012 issued in connection with International Application No. PCT/GB2012/051003.
International Search Report dated Sep. 4, 2012 issued in connection with International Application No. PCT/GB2012/051002.
International Search Report dated Dec. 3, 2012 issued in connection with International Application No. PCT/GB2012/052115.
International Search Report dated Dec. 4, 2012 issued in connection with International Application No. PCT/GB2012/052174.
Karampetsou et al., "TNF-α antagonists beyond approved indications: stories of success and prospects for the future", QJM, vol. 103, No. 12, pp. 917-928, Aug. 27, 2010.
Pelat et al., "Non-human primate immune libraries combined with germline humanization: an (almost) new, and powerful approach for the isolation of therapeutic antibodies," mAbs, vol. 1, No. 4, pp. 377-381, Jul. 1, 2009.
Pelat et al., "Obtention and engineering of non-human primate (NHP) antibodies for therapeutics," Mini Reviews in Medicinal Chemistry, vol. 9, No. 14, pp. 1633-1638, Dec. 1, 2009.
Presta, "Engineering of therapeutic antibodies to minimize immunogenicity and optimize function," Advanced Drug Delivery Reviews, Elsevier vol. 58, No. 5-6, pp. 640-656, Aug. 7, 2006.
Gorman and Clark, "Humanisation of monoclonal antibodies for therapy," Seminars in Immunology, vol. 2, pp. 457-466, Nov. 1990.

Gorman et al., "Reshaping a therapeutic CD4 antibody," Proc. Natl. Acad. Sci USA, vol. 88, pp. 4181-4185, May 1991.
Riechmann et al., "Reshaping human antibodies for therapy," Nature, vol. 332, pp. 323-327, Mar. 1988.
Office Action dated Jan. 29, 2016 in U.S. Appl. No. 14/342,943 (US 2014/0328838).
Notice of Allowance dated Dec. 31, 2015 in U.S. Appl. No. 14/115,787 (US 2014/0147439).
Office Action dated Oct. 16, 2015 in U.S. Appl. No. 14/115,787 (US 2014/0147439).
Office Action dated Nov. 27, 2015 in U.S. Appl. No. 14/115,772 (US 2014/0170136).
Tang et al., "Cloning and characterization of cDNAs encoding four different canine immunoglobulin y chains", Vet. Immunol. Immunopathol., 80:259-270, Aug. 2001.
NCBI Genbank Accession No. AAA61986, "NGF-binding Ig light chain; partial [Rattus norvegicus]," Feb. 7, 1995.
NCBI Genbank Accession No. AAA61985, "NGF-binding Ig heavy chain, partial [Rattus norvegicus]," Feb. 7, 1995.
Gearing et al., "A fully caninised anti-NGF monoclonal antibody for pain relief in dogs," BMC Veterinary Research, 9:226, Nov. 2013.
Gearing et al., "In Vitro and In Vivo Characterization of a Fully Felinized Therapeutic Anti-Nerve Growth Factor Monoclonal Antibody for the Treatment of Pain in Cats," Journal of Veterinary Internal Medicine, vol. 30, pp. 1129-1137, 2016.
Office Action dated Aug. 10, 2016 in U.S. Appl. No. 14/115,779 (US 2014-0170137).
Office Action dated May 20, 2016 in U.S. Appl. No. 14/115,772 (US 2014-0170136).
Office Action dated Aug. 2, 2016 in U.S. Appl. No. 14/342,943 (US 2014-0328838).
Foote et al., "Antibody Framework Residues Affecting the Conformation of the Hypervariable Loops," J. Mol. Biol., vol. 224, pp. 487-499, 1992.
Office Action dated Feb. 24, 2017 in U.S. Appl. No. 14/115,772 (US 2014-0170136).
Office Action dated Mar. 17, 2017 in U.S. Appl. No. 14/342,943 (US 2014-0328838).
Abdiche et al., "Probing the binding mechanism and affinity of tanezumab, a recombinant humanized anti-NGF monoclonal antibody, using a repertoire of biosensors," Protein Science, vol. 17, pp. 1326-1335, Aug. 2008.
Staelens et al., "Humanization by variable domain resurfacing and grafting on a human IgG$^4$, using a new approach for determination of non-human like surface accessible framework residues based on homology modelling of variable domains," Molecular Immunology, vol. 43, pp. 1243-1257, Aug. 2005.
Covaceuszach, S. et al. "Single Cycle Structure-Based Humanization of an Anti-Nerve Growth Factor Therapeutic Antibody." PLoS One, vol. 7, No. 3, 2012 (12 pgs.).
Lazar, G. et al. "A molecular immunology approach to antibody humanization and functional optimization." Molecular Immunology, vol. 44, 2007, pp. 1986-1998.
Office Action dated Aug. 15, 2017 in U.S. Appl. No. 14/115,772 (US 2014-0170136).
Williams, D. et al. "Humanising Antibodies by CDR Grafting." Antibody Engineering vol. 1, Chapter 21, R. Kontermann et al. Eds., 2010, pp. 319-339.

```
                        *  ** *     *
Caninised VL    DIQMTQSPASLSLSQEEKVTITCRASEDIYNALAWYQQKP
40

** *                         *   *   *
Caninised VL    GQAPKLLIYNTDTLHTGVPSRFSGSGSGTEYSLTINSLES
80

*              *   *
Caninised VL    EDVAVYFCQHYFHYPRTFGAGTKVELK 107
```

Figure 6 – Light chain variable domain

```
                       *   *   **   *  **   *  *  *
Caninised VH    EVQLVESGGDLVNPGGTLTLSCVVSGFSLTNNNVNWVRQA
40

*          *                             *
Caninised VH    LGRGLEWVGGVWAGGATDYNSALKSRLTITRDTSKSTVFL
80

82ABC              100ABCDEF         *
Caninised VH    KMHSLQSEDTATYYCARDGGYSSSTLYAMDAWGQGTLVTVSS
113
```

Figure 7 – Heavy chain variable domain

DIQMTQSPASLSLSQEEKVTITCRASEDIYNALAWYQ
QKPGQAPKLLIYNTDTLHTGVPSRFSGSGSGTEYSLTI
NSLESEDVAVYFCQHYFHYPRTFGAGTKVELKRNDA
QPAVYLFQPSPDQLHTGSASVVCLLNSFYPKDINVKW
KVDGVIQDTGIQESVTEQDKDSTYSLSSTLTMSSTEYL
SHELYSCEITHKSLPSTLIKSFQRSECQRVD

Figure 8 – Caninised anti-NGF VL canine kappa light chain (caN-kLC)

EVQLVESGGDLVNPGGTLTLSCVVSGFSLTNNNVNWVR
QALGRGLEWVGGVWAGGATDYNSALKSRLTITRDTSKS
TVFLKMHSLQSEDTATYYCARDGGYSSSTLYAMDAWG
QGTLVTVSSASTTAPSVFPLAPSCGSTSGSTVALACLVS
GYFPEPVTVSWNSGSLTSGVHTFPSVLQSSGLHSLSSMV
TVPSSRWPSETFTCNVVHPASNTKVDKPVFNECRCTDTP
PCPVPEPLGGPSVLIFPPKPKDILRITRTPEVTCVVLDLGR
EDPEVQISWFVDGKEVHTAKTQSREQQFNGTYRVVSVL
PIEHQDWLTGKEFKCRVNHIDLPSPIERTISKARGRAHKP
SVYVLPPSPKELSSSDTVSITCLIKDFYPPDIDVEWQSNG
QQEPERKHRMTPPQLDEDGSYFLYSKLSVDKSRWQQG
DPFTCAVMHETLQNHYTDLSLSHSPGK

Figure 9 – Caninised anti-NGF VH canine IgG-A heavy chain (caN-HCA)

EVQLVESGGDLVNPGGTLTLSCVVSGFSLTNNNVNWVR
QALGRGLEWVGGVWAGGATDYNSALKSRLTITRDTSKS
TVFLKMHSLQSEDTATYYCARDGGYSSSTLYAMDAWG
QGTLVTVSSASTTAPSVFPLAPSCGSTSGSTVALACLVS
GYFPEPVTVSWNSGSLTSGVHTFPSVLQSSGLYSLSSMV
TVPSSRWPSETFTCNVAHPASKTKVDKPVPKRENGRVP
RPPDCPKCPAPEMLGGPSVFIFPPKPKDTLLIARTPEVTC
VVVDLDPEDPEVQISWFVDGKQMQTAKTQPREEQFNGT
YRVVSVLPIGHQDWLKGKQFTCKVNNKALPSPIERTISKA
RGQAHQPSVYVLPPSREELSKNTVSLTCLIKDFYPPDIDV
EWQSNGQQEPESKYRTTPPQLDEDGSYFLYSKLSVDKS
RWQRGDTFICAVMHEALHNHYTQESLSHSPGK

Figure 10 – Caninised anti-NGF VH canine IgG-B heavy chain (caN-HCB)

EVQLVESGGDLVNPGGTLTLSCVVSGFSLTNNNVNWVR
QALGRGLEWVGGVWAGGATDYNSALKSRLTITRDTSKS
TVFLKMHSLQSEDTATYYCARDGGYSSSTLYAMDAWG
QGTLVTVSSASTTAPSVFPLAPSCGSQSGSTVALACLVS
GYIPEPVTVSWNSVSLTSGVHTFPSVLQSSGLYSLSSMV
TVPSSRWPSETFTCNVAHPATNTKVDKPVAKECECKCN
CNNCPCPGCGLLGGPSVFIFPPKPKDILVTARTPTVTCVV
VDLDPENPEVQISWFVDSKQVQTANTQPREEQSNGTYR
VVSVLPIGHQDWLSGKQFKCKVNNKALPSPIEEIISKTPG
QAHQPNVYVLPPSRDEMSKNTVTLTCLVKDFFPPEIDVE
WQSNGQQEPESKYRMTPPQLDEDGSYFLYSKLSVDKSR
WQRGDTFICAVMHEALHNHYTQISLSHSPGK

Figure 11 – Caninised anti-NGF VH canine IgG-C heavy chain (caN-HCC)

EVQLVESGGDLVNPGGTLTLSCVVSGFSLTNNNVNWVR
QALGRGLEWVGGVWAGGATDYNSALKSRLTITRDTSKS
TVFLKMHSLQSEDTATYYCARDGGYSSSTLYAMDAWG
QGTLVTVSSASTTAPSVFPLAPSCGSTSGSTVALACLVS
GYFPEPVTVSWNSGSLTSGVHTFPSVLQSSGLYSLSSTV
TVPSSRWPSETFTCNVVHPASNTKVDKPVPKESTCKCIS
PCPVPESLGGPSVFIFPPKPKDILRITRTPEITCVVLDLGRE
DPEVQISWFVDGKEVHTAKTQPREQQFNSTYRVVSVLPI
EHQDWLTGKEFKCRVNHIGLPSPIERTISKARGQAHQPS
VYVLPPSPKELSSSDTVTLTCLIKDFYPPEIDVEWQSNGQ
PEPESKYHTTAPQLDEDGSYFLYSKLSVDKSRWQQGDT
FTCAVMHEALQNHYTDLSLSHSPGK

Figure 12 – Caninised anti-NGF VH canine IgG-D heavy chain (caN-HCD)

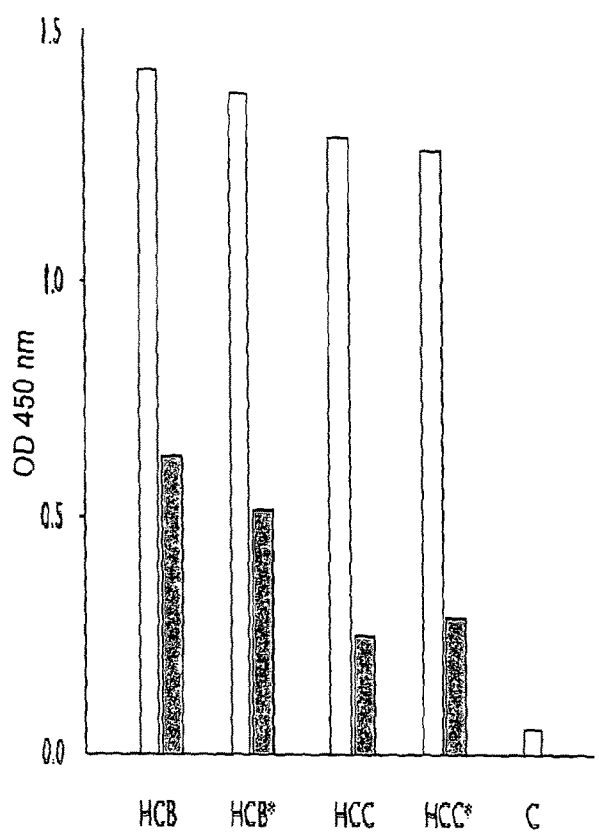 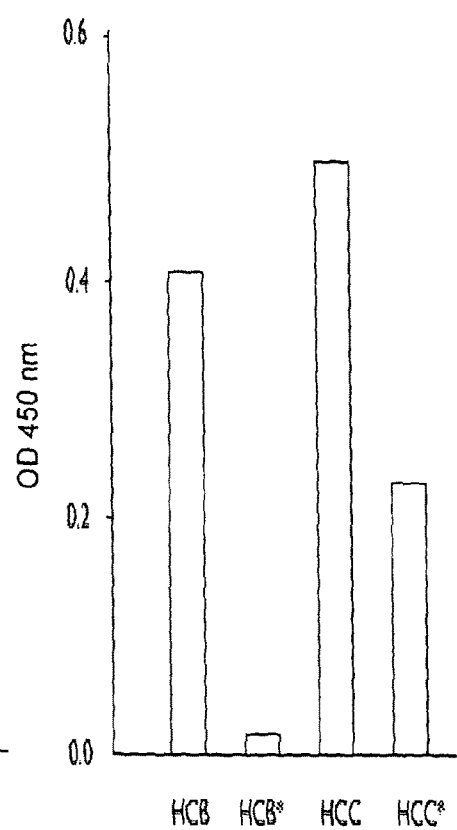
Figure 14A                    Figure 14B

| Peak Retention time (Mins) | Approximate MW (KDa) | % of Total Peak area |
|---|---|---|
| 8.05 | 353 | 2.6 |
| 9.17 | 156 | 89.7 |
| 11.18 | 36 | 7.7 |

SDS-PAGE

Figure 16A

| Study Day | | | -1 | 1 | 3 | 7 |
|---|---|---|---|---|---|---|
| Animal ID | Sex | Age on Study Day 0 (months) | | | | |
| 68305 | M | 11 | 9.6 | 10.0 | 9.9 | 10.0 |
| 26885 | F | 19 | 9.2 | 9.9 | 9.5 | 9.8 |
| 32886 | F | 11 | 9.4 | 9.9 | 9.7 | 10.0 |

| Study Day | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Animal ID | | | | | | | | | | | | | | | |
| 68305 | 38.2 | 38.6 | 38.6 | 38.5 | 38.4 | 38.5 | 38.4 | 38.3 | 38.7 | 38.2 | 38.3 | 38.9 | 38.4 | 38.6 | 38.5 |
| 26886 | 37.8 | 38.2 | 38.0 | 38.2 | 38.4 | 37.7 | 38.1 | 38.2 | 38.4 | 38.2 | 38.4 | 38.6 | 38.5 | 38.4 | 38.6 |
| 32886 | 36.8 | 38.7 | 38.9 | 38.8 | 38.7 | 38.8 | 38.7 | 38.5 | 38.8 | 38.7 | 38.3 | 39.2 | 38.7 | 38.7 | 38.8 |

Figure 17

CANINIZED ANTI-NERVE GROWTH FACTOR ANTIBODIES

FIELD OF THE INVENTION

The present invention relates to antibodies, and fragments thereof, which act as antagonists of canine nerve growth factor. The invention extends to methods of preparing same and to the therapeutic use of these antibodies and fragments in treating conditions associated with nerve growth factor such as pain, pain related disorders and conditions which result in the occurrence of chronic pain in canines.

BACKGROUND TO THE INVENTION

Nerve growth factor (NGF) is a naturally occurring secreted protein which consists of an alpha, beta and gamma polypeptide chain. NGF is a member of the neurotrophin family and is implicated in a number of different roles. NGF promotes survival and differentiation of sensory and sympathetic neurons and signals via two membrane bound receptors, p75, a low affinity NGF receptor and TrkA, a transmembrane tyrosine kinase and a high affinity NGF receptor. The binding of NGF to TrkA or p75 results in an upregulation of neuropeptides in sensory neurons.

The use of NGF antagonists to treat pain and pain sensitivity in humans has been described (Cattaneo A., Curr. Op. Mol. Ther. 2010 12(1):94-106). For example, International Patent Application No. WO 2006/131951 describes a humanised form of the rat alphaD11 (αD11, αD11) monoclonal antibody. The αD11 antibody has binding specificity to mouse NGF, but is also known to bind to human and rat forms of NGF. Humanisation of the αD11 rat derived monoclonal antibody is required prior to administration to humans in order to minimise the production of neutralising antibodies which result from a human anti-mouse antibody (HAMA) response being mounted against rodent derived antibodies. Furthermore, the replacement of mouse constant domains with human constant domains allows downstream effector functions to be selected for.

Pain management in canines is currently provided through administration of analgesic drugs of several classes, including local and general anaesthetics, opioid analgesics, α2 agonists, non-steroidal anti-inflammatory drugs (NSAIDs) and steroids. Each of these needs to be administered frequently and also has limitations in efficacy and safety. There is accordingly a need for an infrequently dosed, long lasting and efficacious form of pain relief for canines suffering from chronic pain, such as those with cancer pain or arthritis.

While NGF is expressed in canine tissues and the canine NGF molecule has been characterised (Eisele I. Wood I S. German A J. Hunter L. Trayhurn P. "Adipokine gene expression in dog adipose tissues and dog white adipocytes differentiated in primary culture" Hormone & Metabolic Research. 37(8):474-81, 2005 Genbank XP_540250), no antagonist to canine NGF has been described, nor has the use of blocking NGF mediated signalling in canines to prevent or alleviate pain. The use in canines of known antibodies which act as anti-NGF antagonists in other species would not be feasible due to the production of neutralising antibodies. Furthermore, the production of a chimeric antibody comprising canine derived constant domains and variable domains derived from a known anti-NGF antibody such as alphaD11 could not be guaranteed to bind to canine NGF. Furthermore, such an antibody may exhibit cross-reactivity to other target epitopes which may be present in canines, but not present in the species from which the antibody was originally derived. Furthermore, the production of neutralising antibodies would limit the long term therapeutic administration of the antibody, this being a particularly important requirement when treating a chronic pain related condition or a cancerous condition. Likewise, the production of a caninised form of an anti-NGF antibody using CDR grafting, or a related technique may also result in neutralising antibody production and may further exhibit a reduction in antigen binding affinity and avidity. Accordingly, there is a serious need for binding members which act as antagonists of canine NGF for use in pain management in canines, wherein the binding members retain high levels of binding affinity and avidity, while avoiding the production of neutralising antibodies there against.

SUMMARY OF THE INVENTION

Following extensive efforts, the present inventor has surprisingly identified a method for preparing antibodies which produces non-immunogenic antibodies and binding fragments which bind specifically to canine NGF and which neutralise canine NGF biological activity. In particular, it is demonstrated herein, quite unexpectedly, that the binding of the antibodies and binding fragments of the invention to canine NGF sequesters the biological activity of canine NGF by inhibiting the binding of canine NGF to the high affinity TrkA receptor or to the p75 receptor. This, in turn, prevents the upregulation of neuropeptides in sensory neurons with the resulting effect that the sensation of pain will be reduced or removed. The antibodies have been produced using recombinant DNA methods and are unexpectedly non-immunogenic, that is, neutralising antibodies are not raised against them following administration to a canine subject. Such a finding is entirely surprising and unexpected, as the antibodies were not produced using standard methodologies, such as CDR grafting, or the like.

According to a first aspect of the invention there is provided a method of preparing an antibody suitable for use in a canine comprising or consisting essentially of the steps of:

providing a donor antibody from a species other than a canine, wherein the donor antibody has binding specificity for a target antigen present in canines;

comparing each amino acid residue of the amino acid sequence of framework regions of the donor antibody with each amino acid residue present at a corresponding position in the amino acid sequence of framework regions of one or more canine antibodies to identify one or more amino acid residues within the amino acid sequence of the framework regions of the donor antibody that differ from one or more amino acid residues at the corresponding position within the amino acid sequence of framework regions of the one or more canine antibodies; and substituting the one or more identified amino acid residues in the donor antibody with the one or more amino acid residues present at the corresponding position in the one or more canine antibodies.

The method of the present invention modifies a donor antibody for use in a canine in such a way that the modified antibody does not contain any amino acid in any position within the framework regions which would be foreign at that position in canines. The modified antibody therefore retains the specificity and affinity of the donor antibody for the target antigen, but importantly is modified such that no potentially foreign epitopes are created. The modified antibody is therefore not seen as foreign in canines and hence does not induce an immune response in canines which could lead to a neutralisation of the efficacy of the antibody, especially following long term administration.

In certain embodiments, the step of substituting the one or more identified amino acid residues comprises substituting the one or more identified amino acid residues with the one or more amino acid residues present at the corresponding position which have the highest homology to the one or more substituted amino acid residues.

In certain embodiments, the method further comprises the step of replacing constant domains of the heavy chain and/or light chain of the donor antibody with constant domains of a heavy and/or light chain derived from a canine antibody. Typically, the constant domain of the heavy chain is replaced with a type HCA or HCD canine constant domain.

In certain embodiments, the target antigen is nerve growth factor (NGF).

The method of the first aspect of the invention does not comprise CDR grafting. Antibodies prepared according to the method of the first aspect of the invention comprise CDRs of the donor antibody, caninised framework regions prepared according to the method of the first aspect of the invention and canine constant domains.

The present invention extends to antibodies prepared according to the first aspect of the present invention such as those described below.

Accordingly, according to a further aspect of the invention there is provided a caninised antibody or binding fragment thereof which binds specifically to canine neuronal growth factor (NGF). Typically, the caninised antibody or binding fragment thereof neutralises NGF biological function, when bound thereto. That is, the binding of the caninised antibody or binding fragment to NGF sequesters the ability of NGF to bind to the TrkA receptor or to the p75 receptor. In certain embodiments, the caninised antibody, or binding fragment thereof, binds to NGF with a binding affinity $K_D$ of $1 \times 10^{-8}$ or less.

In a further or related aspect of the invention there is provided a neutralising antibody, or an antigen binding fragment thereof, which is capable of specifically binding to canine nerve growth factor (NGF), the antibody or antibody binding fragment comprising, consisting of or consisting essentially of a light chain variable region comprising the amino acid sequence of SEQ ID NO:1 or SEQ ID NO:3 or an amino acid sequence which has an identity of at least 85, 90, 95 or 99% thereto. In certain embodiments said identity is over a length of at least about 15 amino acids, preferably about 20 amino acids, more preferably about 25 amino acids.

In some embodiments the neutralising antibody is a monoclonal antibody. In some embodiments, the antibody is a chimeric antibody. In some embodiments, the antibody is a caninised antibody, that is, an antibody which has an amino acid sequence which has been de-immunised such that neutralising antibodies will not be produced there against when administered to a canine subject. In certain embodiments, the caninised antibody is prepared according to the method of preparing an antibody of the first aspect of the invention. Typically the heavy chain constant domains of the antibody are selected or modified by way of amino acid substitution or deletion such that the constant domains do not mediate downstream effector functions.

In some embodiments, the antibody or antibody binding fragment comprises, consists of, or consists essentially of a light chain comprising the amino acid sequence of SEQ ID NO:5 or SEQ ID NO:10, or an amino acid sequence which has at least 85, 90, 95 or 99% sequence homology thereto.

In certain embodiments said identity is over a length of at least about 15 amino acids, preferably about 20 amino acids, more preferably about 25 amino acids.

In a further or related aspect, there is provided a neutralising antibody, or an antigen binding fragment thereof, which is capable of specifically binding to canine nerve growth factor (NGF), the antibody or antibody binding fragment comprising, consisting of or consisting essentially of a heavy chain variable region comprising the amino acid sequence of SEQ ID NO:2 or SEQ ID NO:4 or an amino acid sequence which has an identity of at least 85, 90, 95 or 99% thereto. In certain embodiments said identity is over a length of at least about 15 amino acids, preferably about 20 amino acids, more preferably about 25 amino acids.

Typically, the variable region of the heavy chain (VH) is conjoined to a further amino acid sequence which comprises at least one immunoglobulin constant domain. In certain embodiments, the immunoglobulin constant domain is derived from an antibody of the subclass IgG (immunoglobulin G) to form the complete heavy chain of the caninised antibody of the invention. Four different canine constant domains are known. Typically, said constant domains comprise CH1, CH2 and CH3 along with a suitable linker (or "hinge") located between the CH1 and CH2 domains. Typically, the anti-canine NGF antibody of the invention comprises a heavy chain variable domain conjoined to a constant domain, wherein the constant domain does not mediate downstream effector functions such as complement fixation, ADCC, Fc receptor binding, or the like. Typically said heavy chain has a canine heavy chain isotype A or D.

In certain embodiments, the antibody or antibody binding fragment comprises, consists of, or consists essentially of a heavy chain comprising the amino acid sequence selected from the group consisting of SEQ ID NO:6, SEQ ID NO:7, SEQ ID NO:8, SEQ ID NO:9, SEQ ID NO:11, SEQ ID NO:12, SEQ ID NO:13 and SEQ ID NO:14, or an amino acid sequence which has a sequence identity of at least 85, 90, 95 or 99% thereto. In certain embodiments said identity is over a length of at least about 15 amino acids, preferably about 20 amino acids, more preferably about 25 amino acids.

In certain further embodiments, the antibody or binding fragment may comprise a heavy chain where at least one amino acid residue in the constant domain has been substituted or deleted in order to prevent the glycosylation of that amino acid residue. Accordingly, in certain further embodiments, the antibody or antibody binding fragment comprises, consists of, or consists essentially of a heavy chain comprising the amino acid sequence selected from the group consisting of SEQ ID NO:15, SEQ ID NO:16, SEQ ID NO:17, SEQ ID NO:18, SEQ ID NO:19, SEQ ID NO:20, SEQ ID NO:21 and SEQ ID NO:22, or an amino acid sequence which has a sequence identity of at least 85, 90, 95 or 99% thereto. In certain embodiments said identity is over a length of at least about 15 amino acids, preferably about 20 amino acids, more preferably about 25 amino acids.

In some embodiments, antibodies or fragments having a heavy chain constant domain which do not mediate downstream effector functions such as complement fixation, ADCC, Fc receptor binding, or the like are preferred. Such heavy chains may comprise heavy chains of the canine derived subtype IgG-A and may have an amino acid sequence of SEQ ID NO:6, 11, 15 or 19. Further, such heavy chains may comprise heavy chains of the canine derived subtype IgG-D and may have an amino acid sequence of SEQ ID NO:9, 14, 18 and 22.

In a further or related aspect, the present invention extends to a neutralising antibody, or an antigen binding fragment thereof, which is capable of specifically binding to canine nerve growth factor (NGF), the antibody or antibody binding fragment comprising, consisting of or consisting essentially of a light chain and a heavy chain wherein the variable region of the light chain (VL) comprises an amino acid sequence of SEQ ID NO:1 or SEQ ID NO:3 or an amino acid sequence which has a sequence identity of at least 85, 90, 95 or 99% thereto, and wherein the variable region of the heavy chain (VH) comprises, consists or consists essentially of an amino acid sequence which is identical or substantially homologous to the amino acid sequence of SEQ ID NO:2 or SEQ ID NO:4 or an amino acid sequence which has a sequence identity of at least 85, 90, 95 or 98% thereto. In certain embodiments said identity is over a length of at least about 15 amino acids, preferably about 20 amino acids, more preferably about 25 amino acids.

In certain embodiments, the antibody or binding member comprises a light chain which comprises, consists of or consists essentially of the amino acid sequence of SEQ ID NO:5 or SEQ ID NO:10, or to a sequence having an amino acid identity of at least 85%, more preferably of 95% and most preferably at least 98% identity thereto. In certain embodiments said identity is over a length of at least about 15 amino acids, preferably about 20 amino acids, more preferably about 25 amino acids.

In certain embodiments, the antibody or binding member comprises a heavy chain which comprises, consists of or consists essentially of an amino acid sequence selected from the group consisting of SEQ ID NO:6, SEQ ID NO:7, SEQ ID NO:8, SEQ ID NO:9, SEQ ID NO:11, SEQ ID NO:12, SEQ ID NO:13 and SEQ ID NO:14, or an amino acid sequence having a sequence identity of at least 85%, more preferably of 95% and most preferably at least 98% thereto. In certain embodiments said identity is over a length of at least about 15 amino acids, preferably about 20 amino acids, more preferably about 25 amino acids.

In certain embodiments, the antibody may be conjugated to at least one reporter molecule.

In certain further embodiments at least one residue in the constant domain can be substituted or deleted in order to prevent the glycosylation of that residue. Accordingly, in certain further embodiments, the antibody or antibody binding fragment comprises, consists of, or consists essentially of a heavy chain comprising the amino acid sequence selected from the group consisting of SEQ ID NO:15, SEQ ID NO:16, SEQ ID NO:17, SEQ ID NO:18, SEQ ID NO:19, SEQ ID NO:20, SEQ ID NO:21 and SEQ ID NO:22, or a sequence having an amino acid identity of at least 85%, more preferably of 95% and most preferably at least 98% identity thereto. In certain embodiments said identity is over a length of at least about 15 amino acids, preferably about 20 amino acids, more preferably about 25 amino acids.

The inventor has further defined a series of framework regions (FR) which can be combined with complementarity determining regions (CDRs) to form caninised heavy and light chain variable domains. Each of the heavy and light chain domains has 4 framework regions, designated FR1, FR2, FR3 and FR4.

An antibody molecule may comprise a heavy chain variable domain comprising CDR1, CDR2 and CDR3 regions and associated interposed framework regions. The heavy chain variable domain (VH) CDRs are known as HCDRs, with these CDRs being found at the following positions according to the Kabat numbering system: VHCDR1—Kabat residues 31-35, VHCDR2—Kabat residues 50-65, VHCDR3—Kabat residues 95-102 (Kabat E A et al. (1991) Sequences of proteins of immunological interest, 5$^{th}$ edition. Bethesda: US Department of Health and Human Services).

Furthermore, an antibody further comprises a light chain variable domain comprising CDR1, CDR2 and CDR3 regions and associated interposed framework regions. The light chain variable domain (VL) CDRs are known as VLCDRs, with these CDRs being found at the following amino acid residue positions according to the Kabat numbering system: VLCDR1—Kabat residues 24-34, VLCDR2—Kabat residues 50-56, VLCDR3—Kabat residues 89-97.

A light or heavy chain variable domain comprises four framework regions, FR1, FR2, FR3 and FR4, interposed with CDRs in the following arrangement: FR1-CDR1-FR2-CDR2-FR3-CDR3-FR4.

In a yet further aspect, the present invention extends to an anti-NGF antibody, or an NGF binding fragment thereof, the antibody or antibody binding fragment comprising a light chain variable region comprising at least one of:
- an FR1 framework region consisting or comprising of the amino acid sequence of SEQ ID NO:23 or SEQ ID NO:24,
- an FR2 framework region consisting or comprising of the amino acid sequence of SEQ ID NO:25,
- an FR3 framework region consisting or comprising of the amino acid sequence of SEQ ID NO:26 or SEQ ID NO:27,
- an FR4 framework region consisting or comprising of the amino acid sequence of SEQ ID NO:28, and/or a heavy chain variable region comprising at least one of:
- an FR1 framework region consisting or comprising of the amino acid sequence of SEQ ID NO:29,
- an FR2 framework region consisting or comprising of the amino acid sequence of SEQ ID NO:30,
- an FR3 framework region consisting or comprising of the amino acid sequence of SEQ ID NO:31 or SEQ ID NO:32,
- an FR4 framework region consisting or comprising of the amino acid sequence of SEQ ID NO:33.

Typically the light and heavy chain CDRs are derived from an antibody which has binding specificity to canine NGF.

Typically, the production of the caninised anti-canine NGF antibody of the invention does not require back mutations to be introduced into the framework regions of the light or heavy chain variable domains.

In certain embodiments, the light chain variable domain comprising said at least one framework region described above is conjoined to a canine derived light chain constant domain, typically a light chain kappa constant domain, but optionally a lambda light chain. In certain embodiments, said light chain comprises an FR1 region with an amino acid sequence of SEQ ID NO:23 or SEQ ID NO:24, an FR2 region with an amino acid sequence of SEQ ID NO:25, an FR3 region with an amino acid sequence of SEQ ID NO:26 or SEQ ID NO:27, and an FR4 region with an amino acid sequence of SEQ ID NO:28 or a framework region with an amino acid sequence which has a sequence identity of at least 85, 90, 95 or 98% to the foregoing. In certain embodiments said identity is over a length of at least about 5 amino acids, preferably about 10 amino acids.

In certain further embodiments, the heavy chain variable region comprising at least one of the framework regions described above is conjoined to a canine derived heavy chain constant domain. In certain embodiments, the amino acid sequence of the constant domain lacks any post-translational modifications, or may be modified to remove any or all residues which may be subject to N-linked or O-linked glycosylation, such that the constant domains are aglycosylated. In certain embodiments the heavy chain comprises an FR1 region with an amino acid sequence of SEQ ID NO:29, an FR2 region with an amino acid sequence of SEQ ID NO:30, an FR3 region with an amino acid sequence of SEQ ID NO:31 or SEQ ID NO:32 and an FR4 region with an amino acid sequence of SEQ ID NO:33 or a framework region with an amino acid sequence which has a sequence identity of at least 85, 90, 95 or 98% to the foregoing. In certain embodiments said identity is over a length of at least about 5 amino acids, preferably about 10 amino acids.

In certain further embodiments, modifications may be made to the framework regions described herein. That is, the inventor has identified that for some residues in each framework region, there is a choice of amino acid residues which may be present at a given position. Importantly, these framework region modifications do not result in a conformational change to the complementarity determining regions, as this may alter the binding specificity and/or affinity of the resulting antibody. In certain embodiments, the invention extends to introducing 2 or more amino acid substitutions to the amino acid residues of the framework regions of the light chain variable region and/or heavy chain variable region.

Accordingly, in certain further embodiments, the invention extends to polypeptides, such as an antibody, or antigen binding fragment thereof, which comprises a light chain variable domain having an FR1 region comprising the amino acid sequence of SEQ ID NO:23 which has been modified by one or more of the following amino acid substitutions (where the amino acids are denoted by their single letter code): amino acid residue Q at position 3 (Q3) is replaced by the amino acid residue V, T5 is M, S7 is T, A9 is L, L13 is V, Q15 is P or R, E16 is G, K18 is T or P, V19 is A, T20 is S, and T22 is S. Furthermore, one or more of the following substitutions may be further be provided: T5 is I, A9 is P, S12 is A, S14 is R or T, E16 is D, E17 is D, K18 is A, E or L, T22 is Y and C23 is Y.

In certain further embodiments, where the light chain variable domain has the FR1 region comprising the amino acid sequence of SEQ ID NO:24, this may be modified by one or more of the following amino acid substitutions: amino acid residue V at position 3 (V3) is replaced by the amino acid residue Q, T5 is M, S7 is T, A9 is L, L13 is V, Q15 is P or R, E16 is G, K18 is T or P, V19 is A, T20 is S, and T22 is S. Furthermore, one or more of the following substitutions may be further be provided: T5 is I, A9 is P, S12 is A, S14 is R or T, E16 is D, E17 is D, K18 is A, E or L, T22 is Y and C23 is Y.

In certain further embodiments, the light chain FR2 region having the amino acid sequence of SEQ ID NO:25 may be modified by one or more of the following amino acid substitutions: Y2 is F, Q3 is R, A9 is S, K11 is Q, and L12 is R. Furthermore, Y2 can be I or L, Q3 can be I or L, Q4 can be H, K5 can be R, P6 can be A or S, G7 can be D, A9 can be P or T, K11 can be E or R, L12 can be A, G, P or S, I14 can be L, and Y15 can be E, F, N, S or V.

In certain further embodiments, the light chain FR3 region having the amino acid sequence of SEQ ID NO:26 may be modified by one or more of the following amino acid substitutions: S4 is D, E14 is D, Y15 is F, S16 is T, L17 is F, T18 is K, N20 is S, L22 is V, S24 is P, V27 is A, F31 is Y. Furthermore, G1 can be A, V2 can be A, P3 can be S, F6 can be L or V, S7 can be I, G8 can be A, T13 can be A, S16 can be R, T18 can be R, S24 can be A, E25 can be D, G, I or N, V27 can be G, S or T, A28 can be G, and V29 can be I or L.

In certain further embodiments, where the light chain variable domain has the FR3 region comprising the amino acid sequence of SEQ ID NO:27, this may be modified by one or more of the following amino acid substitutions: S4 is D, E14 is D, F15 is Y, S16 is T, L17 is F, T18 is K, S20 is N, L22 is V, P24 is S, V27 is A, Y31 is F. Furthermore, G1 can be A, V2 can be A, P3 can be S, F6 can be L or V, S7 can be I, G8 can be A, T13 can be A, S16 can be R, T18 can be R, S24 can be A, E25 can be D, G, I or N, V27 can be G, S or T, A28 can be G, and V29 can be I or L.

In certain further embodiments, the light chain FR4 region having the amino acid sequence of SEQ ID NO:28 may be modified by one or more of the following amino acid substitutions: E8 is D. Furthermore, G2 can be S, A3 can be P, Q or T, G4 can be E, T5 can be P, K6 can be Q or S, V7 can be L or W, E8 can be R, or L9 can be I.

In certain further embodiments, the heavy chain FR1 region having the amino acid sequence of SEQ ID NO:29 may be modified by one or more of the following amino acid substitutions: D10 is G, N13 is Q, G15 is T, G16 is E, T17 is S, T19 is R, V24 is A, S28 is T, L29 is F, T30 is S. Furthermore, E1 can be D or G, V2 can be E, G, I, L or M, Q3 can be A, E, H, K, L, P, R, S or V, L4 can be P or V, V5 can be A, E, L or M, E6 can be A or Q, S7 can be F, L or T, G9 can be E, D10 can be A, E, N or T, L11 can be Q, R, V or W, V12 can be A, I or M, N13 can be K or R, P14 can be F or T, G15 can be A or E, G16 can be A, T17 can be P, L18 can be R, T19 can be G, K or V, L20 can be I or V, S21 can be Y, V23 can be A, E, I or L, V24 can be G, I, S or T, S25 can be G, P or T, G26 can be D, R or T, F27 can be D, I, L, S, T or V, S28 can be A, D, I, L, M, N, P or R, L29 can be I, M or V, T30 can be D, G, H, I, K, N, R, V.

In certain further embodiments, the heavy chain FR2 region having the amino acid sequence of SEQ ID NO:30 may be modified by one or more of the following amino acid substitutions: L6 is P, R8 is K, E11 is Q, G14 is A. Furthermore, W1 can be C, V2 can be A, F, I or L, Q4 can be H or L, A5 can be D, G, P, S, T or V, G7 can be E, L or R, R8 can be A, E, G, M or Q, G9 can be D, E, R, T or V, L10 can be F, M or P, E11 can be D, H, L, P or R, W12 can be C, F, L, M, S or Y, V13 can be F, I or L, G14 can be L, S or T.

In certain further embodiments, the heavy chain FR3 region having the amino acid sequence of SEQ ID NO:31 may be modified by one or more of the following amino acid substitutions: L2 is F, T5 is S, T8 is N, S9 is A, S11 is N, V13 is L, F14 is Y, K16 is Q, H18 is N, Q21 is R, S22 is A, T27 is V, R32 is K. Furthermore, R1 can be Q, L2 can be V, T3 can be A, I or S, 14 can be L, M, T or V, T5 can be A or F, R6 can be K, D7 can be E or N, T8 can be D, G, I or S, S9 can be D, G, P, T or V, K10 can be E, G, M, N, Q or R, S11 can be D, H, K or R, T12 can be A, I, M or S, V13 can be A, I or M, F14 can be H, S or T, L15 can be I, K16 can be A, D, E, H or R, M17 can be L, H18 can be D, K, P, R, S or T, S19 can be D, G, N, R or T, L20 can be V, Q21 can be G, I, K, S or T, S22 can be D, G, P, T or V, E23 can be A, D or V, T25 can be A, M or S, A26 can be G or V, T27 can be F, I, K, L, M or Q, Y28 can be H, Y29 can be F or H, A31 can be C, G, L, M, R, S, T or V, R32 is A, D, E, G, I, L, M, N, P, Q, S, T or V.

In certain further embodiments, where the heavy chain variable domain has the FR3 region comprising the amino acid sequence of SEQ ID NO:32, this may be modified by one or more of the following amino acid substitutions: L2 is F, T5 is S, T8 is N, S9 is A, S11 is N, V13 is L, F14 is Y, Q16 is K, H18 is N, R21 is Q, S22 is A, T27 is V, R32 is K. Furthermore, R1 can be Q, L2 can be V, T3 can be A, I or S, 14 can be L, M, T or V, T5 can be A or F, R6 can be K, D7 can be E or N, T8 can be D, G, I or S, S9 can be D, G, P, T or V, K10 can be E, G, M, N, Q or R, S11 can be D, H, K or R, T12 can be A, I, M or S, V13 can be A, I or M, F14 can be H, S or T, L15 can be I, K16 can be A, D, E, H or R, M17 can be L, H18 can be D, K, P, R, S or T, S19 can be D, G, N, R or T, L20 can be V, Q21 can be G, I, K, S or T, S22 can be D, G, P, T or V, E23 can be A, D or V, T25 can be A, M or S, A26 can be G or V, T27 can be F, I, K, L, M or Q, Y28 can be H, Y29 can be F or H, A31 can be C, G, L, M, R, S, T or V, R32 is A, D, E, G, I, L, M, N, P, Q, S, T or V.

In certain further embodiments, the heavy chain FR4 region having the amino acid sequence of SEQ ID NO:33 may be modified by one or more of the following amino acid substitutions: L6 is S. Furthermore, W1 can be L, G2 can be A or S, Q3 can be D, H, P or R, T5 can be A, I, N or S, L6 can be P, Q or R, V7 can be I, L or P, T8 can be A, F, I, L, P, S or Y, V9 can be A, S10 can be A, C, P or T, S11 can be A, L or P.

In certain embodiments of the above aspects of the invention, the antibody is a monoclonal antibody. Typically the antibody is a caninised antibody.

In certain embodiments of the above aspects of the invention, the caninised NGF neutralising antibody of the invention, or the binding fragment derived therefrom specifically binds to canine NGF (nerve growth factor) with a binding affinity having an equilibrium dissociation constant ($K_D$) of $1 \times 10^{-8}$ or less. Furthermore, it is preferred that the caninised antibodies are not cross-reactive to any other epitopes present in canines, and further that neutralising antibodies are not generated against the antibodies of the invention when they are administered to a canine. Furthermore, it is preferred that the constant domains of the antibodies do not mediate any downstream effector functions including, but not limited to, complement fixation and activation, ADCC and Fc receptor binding and activation.

In certain embodiments of the above aspects of the invention, the antibody, or antigen binding fragment thereof, has a serum half-life in canines of at least one week. Typically the serum half-life is at least 8 days. Typically, the antibody is not immunogenic in canines.

In certain embodiments of the above aspects of the invention, the antibody, or antigen binding fragment thereof, is purifiable or purified by a method comprising anion exchange chromatography, hydrophobic interaction chromatography and size exclusion chromatography. In alternative embodiments, the antibody, or antigen binding fragment thereof, is purifiable or purified by a method comprising Captoadhere affinity chromatography followed by anion exchange chromatography.

In certain embodiments, the antibody, or antigen binding fragment thereof, does not mediate downstream effector functions. Typically the antibody or binding fragment has a canine heavy chain isotype A or D.

In certain embodiments, the caninised antibody is prepared according to the method of preparing an antibody of the first aspect of the invention.

In certain further embodiments, modifications to the amino acid sequence of the constant regions of the heavy chain may be made to the antibodies of the invention. Said modification may involve the addition, substitution or deletion of one or more amino acid residues. Said amino acid changes are typically performed in order to modify the functional characteristics of the antibody. For example, amino acid modification may be performed to prevent downstream effector functions mediated by the antibody constant domains, for example by preventing the ability of the antibody to bind to Fc receptors, activate complement or induce ADCC. Furthermore, modifications may be made to the amino acid residues of the hinge region of the heavy chain constant domain in order to modify the circulatory half life of an antibody when it is administered to a canine.

The present invention extends to antibody fragments which bind to canine NGF and sequester its ability to bind to the p75 or TrkA receptors.

In certain embodiments the antibody binding fragment may comprise a heavy chain and light chain sequence of the invention being connected by a flexible linker to form a single chain antibody.

A single chain Fv (scFv) comprises a VH and VL domain. The VH and VL domains associate to form a target binding site. These 2 domains are covalently linked by a peptide linker. A scFv molecule can have the form of VL-linker-VH, in cases where the light chain variable domain is required at the N-terminal, or as VH-linker-VL in cases where the VH domain is required at the N-terminal. Accordingly, in certain further embodiments, the antigen binding fragment is a single chain Fv (scFv) antibody fragment. In certain further embodiments, the antibody binding fragment is selected from the group consisting of, but not limited to, a Fab antibody fragment, a Fab' antibody fragment, a F(ab')$_2$ antibody fragment, an Fv antibody fragment, a scFV antibody fragment, and the like.

In some embodiments, the invention provides multispecific or multivalent antibodies comprising an anti-NGF antibody or binding fragment of the invention coupled or conjoined to other antibodies with different binding specificities for use in combination therapy. A multispecific antibody comprises at least one antibody or binding fragment specific to a first NGF epitope, and at least one binding site specific to another epitope present on NGF, or to a different antigen. A multivalent antibody comprises antibodies or antibody binding fragments which have binding specificity to the same NGF epitope. Accordingly, in certain embodiments, the invention extends to an antibody fusion protein comprising four or more Fv regions or Fab regions of the caninised antibodies of the present invention. A yet further embodiment extends to an antibody fusion protein comprising one or more Fab region derived from an antibody described herein along with one or more Fab or Fv regions from antibodies specific for NGF. In certain further embodiments, the invention extends to a bispecific antibody, wherein an antibody or binding fragment thereof according to the present invention is linked to a secondary antibody or binding fragment thereof which has binding specific for a secondary target, said target not being NGF. Preferably said secondary target assists in preventing NGF mediated signalling through the p75 or TrkA receptors. Such multivalent, bispecific or multispecific antibodies can be made by a variety or recombinant methods which would be well known to the person skilled in the art.

A yet further aspect of the invention provides an anti-neurotrophin neutralising antibody comprising a light chain variable domain having the amino acid sequence of SEQ ID NO:1 or SEQ ID NO:3 and/or a heavy chain variable domain having the amino acid sequence of SEQ ID NO:2 or SEQ ID NO:4. In certain embodiments, the neurotrophin is canine nerve growth factor (NGF).

A yet further aspect of the invention provides a method for treating, inhibiting or ameliorating pain in a canine, the method comprising the steps of:

providing a therapeutically effective amount of an anti-canine NGF antibody, or antigen binding fragment thereof, and administering the same to a canine in need thereof.

In certain embodiments, the antibody is a caninised antibody.

In certain embodiments, the antibody comprises a light chain variable domain comprising the amino acid sequence of SEQ ID NO:1 or SEQ ID NO:3 or a sequence which has at least 85% identity thereto and/or a heavy chain variable domain comprising the amino acid sequence of SEQ ID NO:2 or SEQ ID NO:4 or an amino acid sequence having at least 85% sequence homology thereto.

In certain embodiments, the antibody comprises a light chain having the amino acid sequence of SEQ ID NO:5 or SEQ ID NO:10 or a sequence having a sequence identity of at least 85% thereto and/or a heavy chain which comprises, consists of or consists essentially of an amino acid sequence selected from the group consisting of SEQ ID NO:6, SEQ ID NO:7, SEQ ID NO:8, SEQ ID NO:9, SEQ ID NO:11, SEQ ID NO:12, SEQ ID NO:13 and SEQ ID NO:14, or a sequence having an amino acid identity of at least 85% and more preferably at least 98% identity thereto.

In certain embodiments, the anti-canine NGF antibody or antigen binding fragment thereof is any of those provided by the foregoing aspects of the invention.

In certain embodiments, the pain is neuropathic pain. In particular, the pain may be peri-operative, post-operative or post-surgical pain. Post-operative pain may result following any operating procedure which in canines may include, but is not limited to, orthopaedic surgery, soft tissue surgery, ovariohysterectomy procedures, castration procedures and the like. In certain further embodiments, the pain is chronic pain associated with cancer or a cancerous condition (oncologic pain). In certain further embodiments, the pain is associated with, or resulting from, rheumatoid arthritis or osteoarthritis. In certain embodiments, the pain is inflammatory pain or pruritic pain.

According to a yet further aspect of the present invention there is provided a method for the treatment of arthritis or an arthritic condition in a canine subject, said method comprising the steps of:

providing a therapeutically effective amount of an anti-canine NGF antibody according to the invention or antigen binding fragment thereof, and administering the same to a canine in need thereof.

In certain embodiments, the antibody is a caninised antibody. In certain embodiments, the antibody comprises a light chain variable domain comprising the amino acid sequence of SEQ ID NO:1 or SEQ ID NO:3 or a sequence which has at least 85% identity thereto and/or a heavy chain variable domain comprising the amino acid sequence of SEQ ID NO:2 or SEQ ID NO:4 or an amino acid sequence having at least 85% sequence homology thereto.

In certain embodiments, arthritis or arthritic condition includes the conditions selected from the group consisting of immune mediated polyarthritis, rheumatoid arthritis, osteoarthritis and related conditions.

Typically, the treatment of the arthritis or arthritic condition comprises ameliorating, inhibiting, reducing, suppressing or delaying the onset of pain associated with, or attributable to, the arthritic condition.

A further aspect of the present invention provides a method for the treatment of a condition caused by, associated with or resulting in increased expression of canine NGF or increased sensitivity to NGF in a canine subject, said method comprising the steps of:

providing a therapeutically effective amount of a caninised anti-canine NGF antibody according to the invention or antigen binding fragment thereof, and administering the same to a canine in need thereof.

According to a yet further aspect of the present invention there is provided a method for the treatment of a tumour induced to proliferate by NGF in a canine and conditions associated therewith, said method comprising the steps of:

providing a therapeutically effective amount of an anti-canine NGF antibody according to the invention or antigen binding fragment thereof, and administering the same to a canine in need thereof.

In certain embodiments, the tumour is an osteosarcoma. In certain embodiments, the tumour is induced to proliferate by autocrine or paracrine NGF.

In certain embodiments, the foregoing methods of the invention further comprise the step of co-administering at least one further agent which may enhance and/or complement the effectiveness of the anti-NGF antibody of the invention. For example, the antibody or antigen binding fragment thereof may be co-administered along with at least one analgesic, NSAID, opioid, corticosteroid or steroid.

Examples of suitable analgesics include, but are not limited to, butorphanol, buprenorphine, fentanyl, flunixin meglumine, merpidine, morphine, nalbuphine and derivatives thereof. Suitable NSAIDS include, but are not limited to, acetaminophen, acetylsalicylic acid, carprofen, etodolac, ketoprofen, meloxicam, firocoxib, robenacoxib, deracoxib and the like.

In certain further embodiments, the at least one further agent may be a therapeutically active agent which may be one or more of the group selected from an antibiotic, an antifungal therapeutic agent, an antiprotozoal therapeutic agent, an antiviral therapeutic agent or similar therapeutic agents. Furthermore the at least one further agent may be an inhibitor of mediator(s) of inflammation such as a PGE-receptor antagonist, an immunosuppressive agent, such as cyclosporine, or an anti-inflammatory glucocorticoids. In certain further embodiments the at least one further agent may be an agent which is used for the treatment of cognitive dysfunction or impairment, such as memory loss or related conditions which may become increasingly prevalent in older canines. Further still, the at least one further agent may be an anti-hypertensive or other compound used for the treatment of cardiovascular dysfunction, for example, to treat hypertension, myocardial ischemia, congestive heart failure and the like. Further still, the at least one further agent may be a diuretic, vasodilator, beta-adrenergic receptor antagonist, angiotensin-II converting enzyme inhibitor, calcium channel blocker or HMG-CoA reductase inhibitor.

In certain embodiments, the antibody or antigen binding fragment is administered to the canine as part of the foregoing methods at a dose ranging from about 0.01 mg/kg of body weight to about 10 mg/kg of body weight, in particular from 0.03 mg/kg of body weight to about 3 mg/kg of body weight.

In various further aspects, the present invention extends to a composition comprising an antibody or binding fragment thereof according to any foregoing aspect of the invention. In certain embodiments, the composition further comprises at least one pharmaceutically acceptable carrier.

A yet further aspect of the invention provides a pharmaceutical composition for treating pain or a condition resulting in or caused by chronic pain in a canine or a tumour induced to proliferate by NGF, comprising a pharmaceutically effective amount of an antibody according to the present invention, along with at least one pharmaceutically acceptable carrier, excipient or diluent.

In certain embodiments, the composition may further comprise at least one analgesic, NSAID, opioid, corticosteroid or steroid.

In various further aspects, the present invention extends to an isolated nucleic acid which encodes the antibody or antibody binding fragments of the invention.

Accordingly, a yet further aspect of the invention provides an isolated nucleic acid that encodes an antibody or antigen binding fragment according to any of the foregoing aspects of the invention.

In certain embodiments, the polynucleotide encodes a light chain variable domain of an anti-canine NGF antibody or antibody fragment having the amino acid sequence of SEQ ID NO:1 or SEQ ID NO:3, or a light chain having the amino acid sequence of SEQ ID NO:5 or 10.

In certain further embodiments the polynucleotide encodes a heavy chain variable domain of an anti-canine NGF antibody or antibody fragment having the amino acid sequence of SEQ ID NO:2 or SEQ ID NO:4 or a heavy chain having the amino acid sequence selected from the group consisting of SEQ ID NO:6-SEQ ID NO:9, SEQ ID NO:11-SEQ ID NO:14, SEQ ID NO:15-SEQ ID NO:18 and SEQ ID NO:19-SEQ ID NO:22.

In certain embodiments, the isolated nucleic acid further encodes one or more regulatory sequences operably linked thereto.

In a further aspect there is provided an expression vector comprising a polynucleotide comprising a polynucleotide encoding a heavy and/or light chain variable domain or a heavy and/or light chain constant domain of the invention. In certain embodiments the expression vector further comprises one or more regulatory sequences. In certain embodiments the vector is a plasmid or a retroviral vector.

A yet further aspect provides a host cell incorporating the expression vector of the foregoing aspect of the invention. A further aspect of the invention provides a host cell which produces the antibody of any of the foregoing aspects of the invention.

A yet further aspect of the invention provides a method for producing an anti-canine NGF neutralising antibody, the method comprising the step of culturing the host cell of the foregoing aspect of the invention to allow the cell to express the anti-canine NGF neutralising antibody.

A further aspect of the present invention provides a method of purifying an anti-canine NGF antibody according to the invention comprising the steps of:
(i) anion exchange chromatography;
(ii) hydrophobic interaction chromatography; and
(iii) size exclusion chromatography.

A further aspect of the present invention provides a method of purifying an anti-canine NGF antibody according to the invention comprising the steps of:
(i) Captoadhere affinity chromatography; and
(ii) anion exchange chromatography.

A yet further aspect of the present invention provides a method of producing an anti-canine NGF caninised antibody according to the invention comprising the steps of: expressing one or more of the polynucleotides/nucleic acids or vectors of the foregoing aspects of the invention which express the light and/or heavy chains of the antibodies of the invention in a suitable host cell, recovering the expressed polypeptides, which may be expressed together in a host cell, or separately in different host cells, and isolating antibodies.

A yet further aspect of the invention provides a method for treating, ameliorating or inhibiting pain in a canine or treating a tumour induced to proliferate by NGF, the method comprising the step of administering to the canine an effective amount of a polynucleotide according to any of the foregoing aspects of the invention.

A yet further aspect of the invention provides an antibody or antibody binding fragment according to any of the foregoing aspects of the invention, or a pharmaceutical composition according to the foregoing aspects of the invention, or a nucleic acid or vector comprising the same according to any of the foregoing aspects of the invention for use in the treatment or prevention of pain in a canine.

In certain embodiments the pain is acute pain. In certain further embodiments, the pain is chronic pain. Furthermore, the pain may be post-operative pain, or pain resulting from any operating procedure which in canines may include, but is not limited to, orthopaedic surgery, soft tissue surgery, ovariohysterectomy procedures, castration procedures and the like. In certain further embodiments, the pain is chronic pain associated with cancer or a cancerous condition. In certain further embodiments, the pain is associated with, or resulting from, rheumatoid arthritis or osteoarthritis. In certain embodiments, the pain is inflammatory pain or pruritic pain.

A yet further aspect of the invention provides an antibody or antibody binding fragment according to any of the foregoing aspects of the invention, or a pharmaceutical composition according to the foregoing aspects of the invention, or a nucleic acid or vector comprising the same according to any of the foregoing aspects of the invention for use in the treatment of arthritis, in particular osteoarthritis and/or rheumatoid arthritis.

A yet further aspect of the invention provides an antibody or antibody binding fragment according to any of the foregoing aspects of the invention, or a pharmaceutical composition according to the foregoing aspects of the invention, or a nucleic acid or vector comprising the same according to any of the foregoing aspects of the invention for use in the treatment of a tumour induced to proliferate by NGF in a canine subject and conditions associated therewith, in particular osteosarcoma. In certain embodiments, the tumour is induced to proliferate by autocrine or paracrine NGF.

A yet further aspect of the invention provides use of an antibody or antibody binding fragment according to any of the foregoing aspects of the invention, or a pharmaceutical composition according to the foregoing aspects of the invention, or a nucleic acid or vector comprising the same according to any of the foregoing aspects of the invention in the preparation of a medicament for the treatment or prevention of pain in a canine.

Typically the pain is chronic pain. Furthermore, the pain may be post-operative pain, or pain resulting from any operating procedure which in canines may include, but is not limited to, orthopaedic surgery, soft tissue surgery, ovariohysterectomy procedures, castration procedures and the like. In certain further embodiments, the pain is chronic pain associated with cancer or a cancerous condition. In certain further embodiments, the pain is associated with, or resulting from, rheumatoid arthritis or osteoarthritis. In certain embodiments, the pain is inflammatory pain or pruritic pain.

A yet further aspect of the invention provides use of an antibody or antibody binding fragment according to any of the foregoing aspects of the invention, or a pharmaceutical composition according to the foregoing aspects of the invention, or a nucleic acid or vector comprising the same according to any of the foregoing aspects of the invention in the preparation of a medicament for the treatment, inhibition amelioration or prevention of rheumatoid arthritis or osteoarthritis in a canine.

A yet further aspect of the invention provides use of an antibody or antibody binding fragment according to any of the foregoing aspects of the invention, or a pharmaceutical composition according to the foregoing aspects of the invention, or a nucleic acid or vector comprising the same according to any of the foregoing aspects of the invention in the preparation of a medicament for the treatment of a tumour induced to proliferate by NGF in a canine and conditions associated therewith, in particular osteosarcoma. In certain embodiments, the tumour is induced to proliferate by autocrine or paracrine NGF.

In a yet further aspect there is provided a cell line, or a derivative or progeny cell thereof that produces anti-canine NGF neutralising monoclonal antibodies, or fragments thereof according to the invention.

A yet further aspect of the present invention provides a kit for the treatment of pain in canines, or for the treatment of a condition associated with pain, or for the treatment, amelioration or inhibition of pain associated with osteoarthritis or rheumatoid arthritis comprising an anti-canine NGF antibody of binding fragment according to any of the foregoing aspects of the invention and instructions for use of the same.

A yet further aspect of the present invention provides a diagnostic kit for the detection of an anti-canine NGF monoclonal antibody in fluids in vitro, ex vivo and in vivo, for use in determining the concentration of said antibody. The kit may comprise any of the antibodies of the invention or a binding fragment thereof. The kit may comprise instructions for use of same.

BRIEF DESCRIPTION OF THE FIGURES

FIG. 6 shows the amino acid sequence of a light chain variable domain of the caninised anti-NGF (SEQ ID NO:1). The three CDR regions, identified according to Kabat numbering, are underlined. Asterisks above a specific residue indicate differences in the sequence between the caninised sequence and the amino acid sequence of the rat alphaD11 anti-murine NGF monoclonal antibody.

FIG. 7 shows the amino acid sequence of a heavy chain variable domain of the caninised anti-NGF (SEQ ID NO:2). The three CDR regions, identified according to Kabat numbering, are underlined. Asterisks above a specific residue indicate differences in the sequence between the rat aD11 anti-murine NGF monoclonal antibody.

FIG. 8 shows the amino acid sequence (SEQ ID NO:5) of a caninised anti-NGF light chain variable domain canine kappa light chain (caN-kLC) antibody. Variable domain residues are shown in bold.

FIG. 9 shows the amino acid sequence (SEQ ID NO:6) of a caninised anti-NGF heavy chain variable domain canine IgG-A heavy chain (caN-HCA). Variable domain residues are shown in bold.

FIG. 10 shows the amino acid sequence (SEQ ID NO:7) of a caninised anti-NGF heavy chain variable domain canine IgG-B heavy chain (caN-HCB). Variable domain residues are shown in bold.

FIG. 11 shows the amino acid sequence (SEQ ID NO:8) of a caninised anti-NGF heavy chain variable domain canine IgG-C heavy chain (caN-HCC). Variable domain residues shown in bold.

FIG. 12 shows the amino acid sequence (SEQ ID NO:9) of a caninised anti-NGF heavy chain variable domain canine IgG-D heavy chain (caN-HCD). Variable domain residues are shown in bold.

FIG. 14A shows a graph showing the comparison of binding to NGF of N-glycosylated and aglycosylated variants of anti-canine-NGF monoclonal antibodies with HCB and HCC heavy chain isotypes. FIG. 14B shows a graph showing complement deposition of the supernatants from FIG. 14A.

FIG. 15A shows the results of fractionation by size exclusion HPLC. FIG. 15C: SDS-PAGE analysis under non-reducing and reducing conditions. Lane 1 is MWS, lane 2 is 3450 sample 2 µg/mL and 0 µl reducing agent, lane 3 is 3450 sample 4 µg/mL and 0 µl reducing agent, lane 4 is 3450 sample 6 µg/mL and 0 µl reducing agent, lane 5 is MWS, lane 6 is 3450 sample 2 µg/mL and 3 µl reducing agent, lane 7 is 3450 sample 4 µg/mL and 3 µl reducing agent, lane 8 is 3450 sample 6 µg/mL and 3 µl reducing agent and lane 9 is MWS.

FIG. 16 shows a comparison of anti-NGF monoclonal antibody purified by Methods I and II. FIG. 16A: comparison by non-reducing and reducing SDS-PAGE.

FIG. 17 shows body weight (upper panel) and temperature (lower panel) are stable following intravenous administration of anti-canine NGF antibodies into dogs.

DETAILED DESCRIPTION OF THE INVENTION

Figure 1:
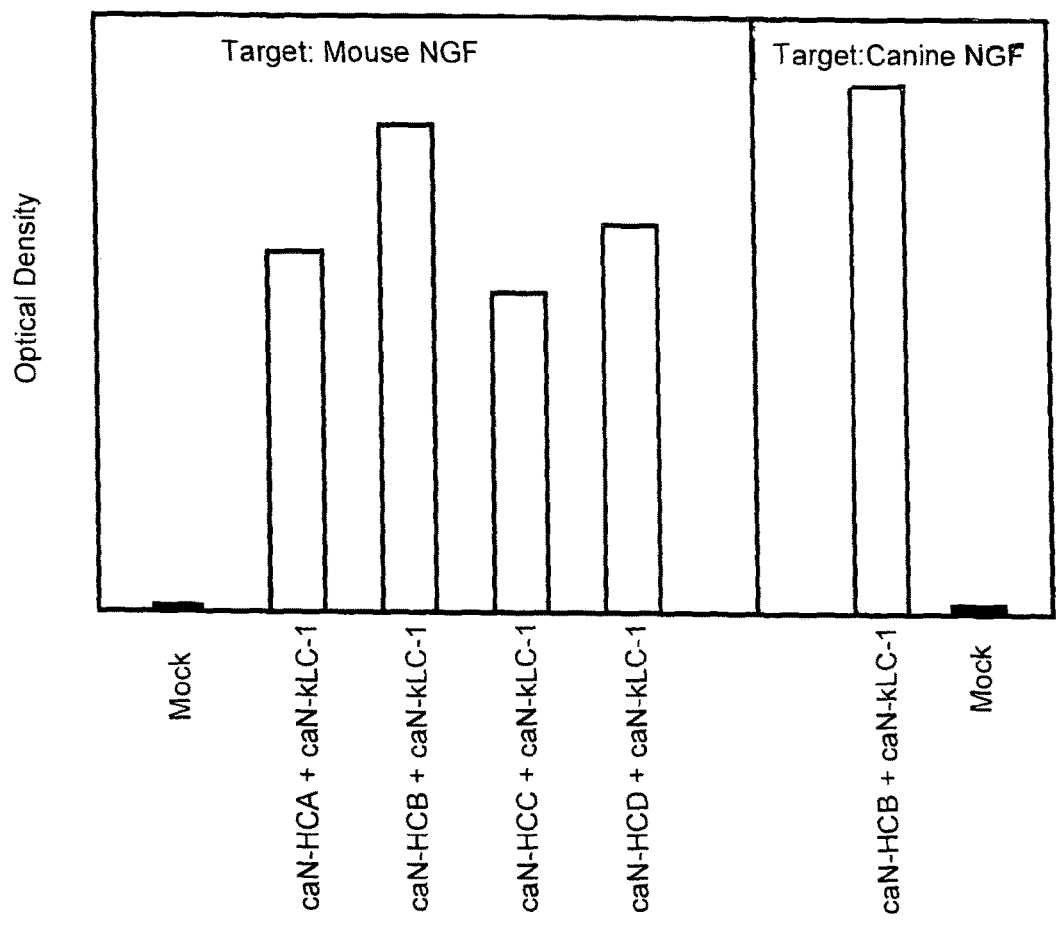
FIG. 1 is a graph showing the binding of caninised antibodies produced according to the invention to murine NGF and canine NGF.

Following extensive experimentation, the inventor has taken the rat anti-mouse NGF monoclonal antibody (MAb) αD11 amino acid sequence and surprisingly used this to produce a non-immunogenic anti-canine NGF antibody. The resulting non-immunogenic antibody, which is not produced using standard CDR grafting techniques, is shown to exhibit high affinity binding to canine NGF. The antibody neutralises canine NGF biological function, most specifically by inhibiting the binding of NGF to cell based receptors TrkA and p75. Furthermore, it has also been discovered, unexpectedly, that when administered to a canine, neutralising antibodies are not produced there against. Accordingly, the caninised antibody of the invention is suitable for long term chronic pain relief in dogs.

The process of generating the heavy and light chain variable domains for the antibodies of the invention which has been employed by the inventor results in the replacement of specific rat (donor) amino acid residues which are present within the framework regions of the light and heavy chain variable domains with residues which, based on the inventor's analysis, will retain the conformation of the CDR regions and therefore maintain binding specificity and avidity, while reducing the presence of immunogenic epitopes which may result in neutralising antibodies being generated against the antibody, if it were to be administered to canines in an unaltered form. Specifically, the method of preparing antibodies of the invention (known as PETisation) comprises assessing the sequence of the framework regions of a donor (e.g. rat) antibody for suitability for administering to a canine by comparing the sequence of the framework regions of the donor antibody with the sequence of an antibody or a pool of antibodies derived from canines. Although the comparison may be between the donor sequence and a single member of the target sequence, it will be obvious that comparison with a pool of target sequences is preferred because this will expand the number of natural options at each Kabat position in the target species. Not only will this increase the chance of a "match" between the donor and the target, but it will also expand the options for replacement where a match does not exist. As a result, a replacement with characteristics as close as possible to the donor will be able to be chosen. Where the donor sequence and the canine sequence differ at any Kabat number or corresponding position, the donor sequence is modified to substitute the amino acid residue in question with an amino acid residue which is known to be natural at that position in canines.

Where substitution of an amino acid residue present in a donor immunoglobulin framework region is required, typically this is undertaken using the principle of conservative substitution wherein an amino acid residue is replaced with an amino acid residue which is natural at that Kabat position in a canine and is as closely related as possible in size, charge and hydrophobicity to the amino acid being substituted in the donor sequence. The intention is to choose a replacement which would cause no, or at least only minimum, perturbation or disruption to the three-dimensional structure of the donor antibody. In certain situations, there will be no clear option and each choice will have benefits and downsides. A final decision may require three-dimensional modelling or even expression of various alternative sequences. However, generally, a clear preference will be available. As a result of this procedure, a change in the donor sequence is only made when that residue would be foreign in the target and the replacement amino acid is as closely related as possible to that which it replaces. Thus, the creation of foreign epitopes is avoided, but the overall three-dimensional structure is preserved and as a result, affinity and specificity are also preserved.

The light and heavy chain constant regions are typically derived from canine (target) derived antibodies. The heavy chain constant domains are selected or modified such that they do not mediate downstream effector functions. As it has been found, quite surprisingly, that no or minimal neutralising antibodies are produced against the antibodies produced according to the invention, the antibodies have surprisingly been found to have the associated benefit of long circulatory half life and the option for repeat dosing. Furthermore, as the substitution of the framework residues is performed in such a manner that it does not affect the three dimensional conformation of the CDR regions, there will be no variation in binding specificity to the desired target.

There are four major IgG isotypes in man and mouse and while nomenclature is similar they differ in behaviour and function including affinity for bacterial products such as Protein A and Protein G, their ability to activate the complement dependent cytolysis (CDC) and their ability to induce killing of target cells through antibody dependent cellular cytotoxity (ADCC). The selection of IgG isotypes with CDC and ADCC active or "armed" constant domains is considered to be of clinical benefit when antibodies are designed to eliminate target cells bearing their cognate antigen, such as in oncology or infection control (e.g. in human medical use human IgG1 isotypes are preferred for the above purposes). By contrast, the activation of the immune system is considered undesirable in other settings such as in the relief of inflammation, pain or autoimmunity and so human IgG isotypes with minimal CDC and ADCC activity are preferred (e.g. in such human medical use, IgG4 isotypes are often preferred). Four distinct immunoglobulin gamma (IgG) heavy chain constant domain isotypes have been described in the canine immune system (U.S. Pat. No. 5,852,183, Tang L. et al. 2001. Veterinary Immunology and Immunopathology, 80. 259-270) along with single kappa and lambda constant domain sequences. The four canine heavy chain constant domains A, B, C and D have not been characterised in terms of functional activity mediated thereby. Despite overall homology to the IgG family, the proteins encoding canine IgG are more related to one another than to family members from other species, so it has not been possible by homology alone to define which of the above functions if any can be ascribed to each of the four canine isotypes. The selection of IgG isotypes with CDC and ADCC active constant domains is considered to be of benefit when antibodies are designed to eliminate target cells bearing the cognate antigen, such as in oncology or infection control, e.g. in human medical use human IgG1 isotypes are preferred. By contrast, the activation of the immune system is considered undesirable in other settings such as in the relief of inflammation, pain or autoimmunity and so human IgG isotypes with minimal or "disarmed" CDC and ADCC activity are preferred, e.g. in human medical use, IgG4 isotypes would be selected.

The antibodies of the invention comprise canine derived heavy and light chain constant domains. Furthermore, the complementarity determining regions are derived from the rat alphaD11 anti-mouse NGF antibody. The αD11 antibody was first described by Cattaneo et al. (Cattaneo A, Rapposelli B, Calissano P. (1988) "Three distinct types of monoclonal antibodies after long-term immunization of rats with mouse nerve growth factor". J Neurochem 50(4):1003-1010). The alphaD11 antibody was subsequently cloned by Ruberti et al. (Ruberti, F. et al. (1993) "Cloning and Expression of an Anti-Nerve Growth Factor (NGF) Antibody for Studies Using the Neuroantibody Approach". Cellular and Molecular Neurobiology. 13(5):559-568).

The CDR regions derived from the αD11 antibody are combined with framework region sequences which have been determined by the inventor to preserve CDR tertiary structure, and therefore binding specificity, while preventing neutralising antibodies being raised there against, when the antibody is administered to a canine.

Each of the light and heavy chain variable regions contains four framework regions, referred to as FR1-FR4. For each of these framework regions, the inventor has identified a preferred amino residue (a so called preferred residue) for each specific position, and furthermore alternative amino acid residues which could also be provided at that position. Tables 1 to 8 below illustrate the 4 framework regions for each of the heavy and light chains. The tables provide the amino acid position relative to that specific framework region and further according to the Kabat numbering system used to identify the position of a particular residue along the length of the complete heavy or light chain variable domain. The residue or residues shown as group 1 residues are the preferred residues, while the group 2 residues are alternative residues. However these would generally not be preferable to the residues shown in group 1 relating to that specific position. The amino acid residues are identified using the single letter system.

TABLE 1

Light chain variable domain FR1 residues

| Light chain FR1 position | Kabat light chain numbering position | Group 1 amino acid residues | Group 2 amino acid residues |
|---|---|---|---|
| 1 | 1 | D | |
| 2 | 2 | I | |
| 3 | 3 | QV | |
| 4 | 4 | M | |
| 5 | 5 | TM | I |
| 6 | 6 | Q | |
| 7 | 7 | ST | |
| 8 | 8 | P | |
| 9 | 9 | AL | P |
| 10 | 10 | S | |
| 11 | 11 | L | |
| 12 | 12 | S | A |
| 13 | 13 | LV | |
| 14 | 14 | S | RT |
| 15 | 15 | QPR | |
| 16 | 16 | GE | D |
| 17 | 17 | E | D |
| 18 | 18 | TKP | AEL |
| 19 | 19 | VA | |
| 20 | 20 | TS | |
| 21 | 21 | I | |
| 22 | 22 | ST | Y |
| 23 | 23 | C | Y |

TABLE 2

Light chain variable domain FR2 residues

| Light chain FR2 position | Kabat light chain numbering position | Group 1 amino acid residues | Group 2 amino acid residues |
|---|---|---|---|
| 1 | 35 | W | |
| 2 | 36 | YF | IL |
| 3 | 37 | QR | IL |
| 4 | 38 | Q | H |
| 5 | 39 | K | R |
| 6 | 40 | P | AS |
| 7 | 41 | G | D |
| 8 | 42 | Q | |
| 9 | 43 | SA | PT |
| 10 | 44 | P | |
| 11 | 45 | KQ | ER |
| 12 | 46 | LR | AGPS |
| 13 | 47 | L | |
| 14 | 48 | I | L |
| 15 | 49 | Y | EFNSV |

TABLE 3

Light chain variable domain FR3 residues

| Light chain FR3 position | Kabat light chain numbering position | Group 1 amino acid residues | Group 2 amino acid residues |
|---|---|---|---|
| 1 | 57 | G | A |
| 2 | 58 | V | A |
| 3 | 59 | P | S |
| 4 | 60 | SD | |
| 5 | 61 | R | |
| 6 | 62 | F | LV |
| 7 | 63 | S | I |
| 8 | 64 | G | A |
| 9 | 65 | S | |
| 10 | 66 | G | |
| 11 | 67 | S | |
| 12 | 68 | G | |
| 13 | 69 | T | A |
| 14 | 70 | DE | |
| 15 | 71 | FY | |
| 16 | 72 | ST | R |
| 17 | 73 | FL | |
| 18 | 74 | KT | R |
| 19 | 75 | I | |
| 20 | 76 | SN | |
| 21 | 77 | S | |
| 22 | 78 | LV | |
| 23 | 79 | E | |
| 24 | 80 | PS | A |
| 25 | 81 | E | DGIN |
| 26 | 82 | D | |
| 27 | 82A | VA | GST |
| 28 | 82B | A | G |
| 29 | 82C | V | IL |
| 30 | 83 | Y | |
| 31 | 84 | YF | |
| 32 | 85 | C | |

TABLE 4

Light chain variable domain FR4 residues

| Light chain FR4 position | Kabat light chain numbering position | Group 1 amino acid residues | Group 2 amino acid residues |
|---|---|---|---|
| 1 | 95 | F | |
| 2 | 96 | G | S |
| 3 | 97 | A | PQT |
| 4 | 98 | G | E |
| 5 | 99 | T | P |
| 6 | 100 | K | QS |
| 7 | 101 | V | LW |
| 8 | 102 | ED | R |
| 9 | 103 | L | I |
| 10 | 104 | K | |

TABLE 5

Heavy chain variable domain FR1 residues

| Heavy chain FR1 position | Kabat heavy chain numbering position | Group 1 amino acid residues | Group 2 amino acid residues |
|---|---|---|---|
| 1 | 1 | E | DG |
| 2 | 2 | V | EGILM |
| 3 | 3 | Q | AEHKLPRSV |
| 4 | 4 | L | PV |
| 5 | 5 | V | AELM |
| 6 | 6 | E | AQ |
| 7 | 7 | S | FLT |
| 8 | 8 | G | |
| 9 | 9 | G | E |
| 10 | 10 | GD | AENT |
| 11 | 11 | L | QRVW |
| 12 | 12 | V | AIM |
| 13 | 13 | QN | KR |
| 14 | 14 | P | FT |
| 15 | 15 | GT | AE |
| 16 | 16 | GE | A |
| 17 | 17 | ST | P |
| 18 | 18 | L | R |
| 19 | 19 | RT | GKV |
| 20 | 20 | L | IV |
| 21 | 21 | S | Y |
| 22 | 22 | C | |
| 23 | 23 | V | AEIL |
| 24 | 24 | AIV | GST |
| 25 | 25 | S | GPT |
| 26 | 26 | G | DRT |
| 27 | 27 | F | DILSTV |
| 28 | 28 | ST | ADILMNPR |
| 29 | 29 | LF | IMV |
| 30 | 30 | ST | DGHIKNRV |

TABLE 6

Heavy chain variable domain FR2 residues

| Heavy Chain FR2 position | Kabat heavy chain numbering position | Group 1 Amino Acid residues | Group 2 Amino Acid residues |
|---|---|---|---|
| 1 | 36 | W | C |
| 2 | 37 | V | AFIL |
| 3 | 38 | R | |
| 4 | 39 | Q | HL |
| 5 | 40 | A | DGPSTV |
| 6 | 41 | LP | |
| 7 | 42 | G | ELR |
| 8 | 43 | RK | AEGMQ |
| 9 | 44 | G | DERTV |
| 10 | 45 | L | FMP |
| 11 | 46 | EQ | DHLPR |
| 12 | 47 | W | CFLMSY |
| 13 | 48 | V | FIL |
| 14 | 49 | GA | LST |

TABLE 7

Heavy chain variable domain FR3 residues

| Heavy chain FR3 position | Kabat heavy chain numbering position | Group 1 amino acid residues | Group 2 amino acid residues |
|---|---|---|---|
| 1 | 66 | R | Q |
| 2 | 67 | LF | V |
| 3 | 68 | T | AIS |
| 4 | 69 | I | LMTV |
| 5 | 70 | ST | AF |
| 6 | 71 | R | K |
| 7 | 72 | D | EN |
| 8 | 73 | TN | DGIS |
| 9 | 74 | AS | DGPTV |
| 10 | 75 | K | EGMNQR |
| 11 | 76 | SN | DHKR |
| 12 | 77 | T | AIMS |
| 13 | 78 | VL | AIM |
| 14 | 79 | FY | HST |
| 15 | 80 | L | I |
| 16 | 81 | KQ | ADEHR |
| 17 | 82 | M | L |
| 18 | 82A | HN | DKPRST |
| 19 | 82B | S | DGNRT |
| 20 | 82C | L | V |
| 21 | 83 | QR | GIKST |
| 22 | 84 | SA | DGPTV |
| 23 | 85 | E | ADV |
| 24 | 86 | D | |
| 25 | 87 | T | AMS |
| 26 | 88 | A | GV |
| 27 | 89 | TV | FIKLMQ |
| 28 | 90 | Y | H |
| 29 | 91 | Y | FH |
| 30 | 92 | C | |
| 31 | 93 | A | CGLMRSTV |
| 32 | 94 | RK | ADEGILMNPQSTV |

TABLE 8

Heavy chain variable domain FR4 residues

| Heavy Chain FR4 position | Kabat heavy chain numbering position | Group 1 Amino Acid residues | Group 2 Amino Acid residues |
|---|---|---|---|
| 1 | 103 | W | L |
| 2 | 104 | G | AS |
| 3 | 105 | Q | DHPR |
| 4 | 106 | G | |
| 5 | 107 | T | AINS |
| 6 | 108 | SL | PQR |
| 7 | 109 | V | ILP |
| 8 | 110 | T | AFILPSY |
| 9 | 111 | V | A |
| 10 | 112 | S | ACPT |
| 11 | 113 | S | ALP |

The caninised antibody of the invention therefore differs from, for example, a chimeric monoclonal antibody which consists of a complete variable region derived from a first species and constant domains derived from a second species, or from a CDR-grafted caninised antibody, where the complementarity determining regions (CDRs) of the heavy and light chain variable regions comprise amino acid residues derived from a donor antibody and introduced into framework regions (FR) and constant regions (CR) derived from a target antibody or from canine germline sequences.

It is preferred that the caninised antibody substantially retains the binding properties of the parent (donor) antibody from which the CDRs are derived. That means that the caninised antibody will exhibit the same or substantially the same antigen-binding affinity and avidity as the donor antibody from which the CDRs are derived. Ideally, the affinity of the caninised antibody will not be less than 10% of the donor antibody affinity for the target epitope, more preferably not less than about 30%, and most preferably the affinity will not be less than 50% of the parent (donor) antibody. Methods for assaying antigen-binding affinity are well known in the art and include half-maximal binding assays, competition assays, and Scatchard analysis.

As defined hereinbefore, the present invention extends to binding members or antigen binding fragments derived from the caninised antibodies of the invention. Such antigen binding fragments refer to one or more fragments of an antibody that retain the ability to specifically bind to canine NGF. It has been shown that the antigen binding function of an antibody can be performed by fragments of a full length antibody. In certain embodiments, the binding members or antigen binding fragments may be isolated binding members. A binding member or antigen binding fragment of the invention may comprise a fragment of the antibodies of the present invention, e.g. a fragment of a fully caninised antibody molecule, such as the heavy or light chain only, or, for example, the variable domain of the heavy and/or light chain. In certain embodiments, a binding member may typically comprise, consist, or consist essentially of an antibody VH and/or VL domain. VH domains of binding members are also provided as part of the invention. Within each of the VH and VL domains are 3 complementarity determining regions ("CDRs"), along with 4 associated framework regions ("FRs"). A VH domain typically comprises 3 HCDRs (heavy chain complementarity determining regions), and a VL domain typically comprises 3 LCDRs (light chain complementarity regions). Accordingly, a binding member may comprise a VH domain comprising, in sequence, VH CDR1 (or HCDR1), CDR2 (HCDR2) and CDR3 (HCDR3) regions along with a plurality of associated framework regions. A binding member may additionally or alternatively comprise a VL domain comprising VL CDR1, CDR2 and CDR3 domains along with associated framework regions. The VH or VL domains typically comprise four framework regions, FR1, FR2, FR3 and FR4. As used herein, the term "framework region" or "framework sequence" refers to the remaining sequences of a variable region minus the CDRs. Because the exact definition of a CDR sequence can be determined by different systems (Kabat, Chothia etc.), the meaning of a framework sequence is subject to correspondingly different interpretations. The six CDRs (VL-CDR1, CDR2 and CDR3 of the light chain and VH-CDR1, CDR2 and CDR3 of the heavy chain) divide the framework regions on the light chain and the heavy chain into four sub-regions known as FR1, FR2, FR3 and FR4 on each chain.

FIG. 6 shows the amino acid sequence of a light chain variable domain of an anti-NGF antibody according to the invention. The CDR1, CDR2 and CDR3 regions are underlined. As such, and as shown in FIG. 6 the VL-CDR1 is positioned between FR1 and FR2 framework regions, the VL-CDR2 is positioned between the FR2 and FR3 framework regions, and the VL-CDR3 is positioned between the FR3 and FR4 framework regions. FIG. 7 shows the amino acid sequence of a heavy chain variable domain of an anti-NGF antibody according to the invention. The CDR1, CDR2 and CDR3 regions are underlined. As with the light chain variable region shown in FIG. 6, the VH-CDR1 is positioned between FR1 and FR2 framework regions, the VH-CDR2 is position between the FR2 and FR3 framework regions, and the VH-CDR3 is positioned between the FR3 and FR4 framework regions.

In FIGS. 6 and 7, the residues of the light chain variable domain (FIG. 6) and heavy chain variable domain (FIG. 7) are conventionally numbered according to the numbering system devised by Kabat et al. (Kabat, E. A., Wu, T. T., Perry, H., Gottesman, K. and Foeller, C. (1991) Sequences of Proteins of Immunological Interest, Fifth Edition. NIH Publication No. 91-3242, Kabat et al. (1971) Ann. NY Acad, Sci. 190:382-391). The Kabat numbering system refers to a system of numbering amino acid residues which are more variable (i.e. hypervariable) than other amino acid residues in the heavy and light chain variable regions of an antibody, or an antigen binding portion thereof. The Kabat numbering system is therefore generally used when referring to a residue in the variable domain (approximately residues 1-104 of the light chain and residues 1-113 of the heavy chain). This numbering system may be used in the present specification, where stated. The Kabat residue designations do not always correspond directly with the linear numbering of the amino acid residues of the heavy and light chain variable regions of the present invention provided in the relevant sequences listed herein. In particular, the actual linear amino acid sequence may contain fewer or additional amino acids than in the strict Kabat numbering corresponding to a shortening of, or insertion into, a structural component, whether a framework region or complementarity determining region (CDR), of the basic variable domain structure of the heavy or light chain. The correct Kabat numbering of residues may be determined for any given antibody by alignment of residues in the sequence of the antibody with a standard sequence to which the Kabat numbering has been applied.

Furthermore, FIG. 7 shows a heavy chain variable domain amino acid sequence. This is also shown in SEQ ID NO:2. However, in FIG. 7, the numbering takes account of amino acid residues 80, 80A, 80B, and 80C, whereas in SEQ ID NO:2, the numbering continues sequentially, that is 80, 81, 82 and 83. The same is true for Kabat residues 100, 100A, 100B, 100C, 100D, 100E and 100F in FIG. 7.

As described hereinbefore, an antibody binding fragment may be selected from the group comprising, but not limited to, a Fab fragment, a Fab' fragment and a scFv (single chain variable fragment), or from a peptidomimetic, a diabody, or a related multivalent derivative.

In certain embodiments the antibody binding fragment is a Fab, or F(ab')2 fragment, which consists of the VL, VH, CL and CH1 domains of an antibody. In certain embodiments, the VL domain has an amino acid sequence of SEQ ID NO:1 or SEQ ID NO:3, and the VH domain has an amino acid sequence of SEQ ID NO:2 or SEQ ID NO:4. In certain embodiments, the CL and CH1 domains are based on the amino acid sequence of a CL and CH1 domain of a canine immunoglobulin.

Techniques used for the recombinant production of Fab, Fab' and F(ab')2 fragments are well known to the person skilled in the art and include those disclosed in International PCT Patent Publication WO 92/22324, and in Sawai et al., "Direct Production of the Fab Fragment Derived From the Sperm Immobilizing Antibody Using Polymerase Chain Reaction and cDNA Expression Vectors", 1995, AJRI 34:26-34. Examples of techniques which can be used to produce scFv (single chain Fv fragments) are disclosed in Huston et al., "Protein Engineering of Single-Chain Fv Analogs and Fusion Proteins", *Methods in Enzymology*, vol. 203:46-88 (1991), the contents of which are incorporated by reference.

In certain embodiments, antibody fragments can be derived from full length antibodies by proteolytic digestion according to the method of Morimoto (Morimoto et al., "Single-step purification of F(ab')2 fragments of mouse monoclonal antibodies (immunoglobulins G1) by hydrophobic interaction high performance liquid chromatography using TSKgel Phenyl-5PW" Journal of Biochemical and Biophysical Methods 24:107-117 (1992)). Antibody fragments can also be produced directly by host cells (Carter et al., "High level *Escherichia coli* expression and production of a bivalent humanized antibody fragment" Bio/Technology 10:163-167 (1992)).

In addition to providing a caninised monoclonal antibody which has binding specificity to canine NGF and which antagonises canine NGF function, the present invention further extends to binding members other than antibodies comprising a pair of binding domains based on the amino acid sequence of a VL (light chain variable) region as defined in SEQ ID NO:1 or SEQ ID NO:3 and an amino acid sequence of a VH (heavy chain variable) region as defined in SEQ ID NO:2 or SEQ ID NO:4. In particular, the invention extends to single binding domains which are based on either the VL or VH region of the caninised antibodies of the antibodies of the invention.

Accordingly, in certain further embodiments of the present invention, there is provided a binding member comprising, consisting or consisting essentially of a single binding domain derived from the humanised antibody of the invention. In certain embodiments, the single binding domain is derived from the amino acid sequence of the VH (heavy chain variable domain) as defined in SEQ ID NO:2 or SEQ ID NO:4. Such a binding domain may be used as a targeting agent to canine NGF.

In certain embodiments, further engineering techniques can be used to modify the antibodies of the present invention, for example by including modifications of the Fc region which can alter serum half life, complement fixation, Fc receptor binding and/or antigen dependent cellular cytotoxicity. Further, in certain embodiments, antibodies or antibody fragments can be produced which have altered glycosylation patterns. In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The inventor has provided aglycosylated canine constant domains, these being defined herein as SEQ ID NO:15, 16, 17, 18, 19, 20, 21, and 22.

In certain further embodiments, the anti-canine NGF antibodies of the invention can be PEGylated by reacting the antibody with a plyethylene glycol (PEG) derivative. In certain embodiments, the antibody is defucosylated and therefore lacks fucose residues.

In certain embodiments, modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (A. L. Lehninger, in Biochemistry, $2^{nd}$ Ed., 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Such substituted residues also may be introduced into the conservative substitution sites or, into the remaining (e.g., non-conserved) sites.

In various further aspects, the present invention extends to an immunoconjugate comprising an anti-canine NGF antibody of the invention, or an antigen binding portion thereof linked to a partner molecule. In certain embodiments, such an antibody-partner molecule conjugate is conjugated by means of a chemical linker, such as a peptidyl linker, a hydrazine linker or a disulphide linker. In certain embodiments, the coupling partner is an effector molecule, label, drug, or carrier molecule. Suitable techniques for coupling the antibodies of the invention to both peptidyl and non-peptidyl coupling partners will be well known to persons skilled in the art. Examples of suitable labels include detectable labels, such as a radiolabel, or an enzymatic label, such as horse radish peroxidase, or chemical moieties, such as biotin. Alternatively, the label may be a functional label, for example, ricin, or pro-drugs which are capable of converting prodrugs into active drugs at the site of antibody binding.

In various further aspects, the present invention extends to polynucleotides, and in particular isolated polynucleotides, which encode the caninised antibodies, antibody fragments and binding members of the present invention. As defined herein, a "polynucleotide" includes any polyribonucleotide or polydeoxyribonucleotide, which may be unmodified RNA or DNA, or modified RNA or DNA, including without limitation, single and double stranded RNA, and RNA which is a mixture of single and double stranded regions. A polynucleotide of the invention, e.g. a polynucleotide which encodes a polypeptide or polypeptides of the invention includes allelic variants thereof and/or their complements including a polynucleotide that hybridises to such nucleotide sequences under conditions of moderate or high stringency.

The present invention further extends to antibody mimetics, such as domain antibodies, nanobodies, unibodies, versabodies, and duocalins which are based on the canine NGF antibodies of the present invention. A wide variety of antibody mimetic technologies are known to the person skilled in the art. For example, so called, domain antibodies (Domantis, UK) are small functional binding units of antibodies which correspond to the variable regions of either the light or heavy chains of human antibodies. Directions for the production of such domain antibodies can be found in U.S. Pat. No. 6,291,158, U.S. Pat. No. 6,582,915 and U.S. Pat. No. 6,593,081. Nanobodies are antibody-derived therapeutic proteins which contain unique structural and functional properties of naturally occurring heavy chain antibodies found in camelids. Unibodies are a further antibody fragment technology, based upon the removal of the hinge region of IgG4 antibodies. The deletion of the hinge region results in a molecule which is approximately half the size of a traditional IgG4 antibody and which has a univalent binding region. Unibodies preserve the property of IgG4 antibodies of being inert and therefore not inducing immune responses.

Further binding molecules include affibody molecules (U.S. Pat. No. 5,831,012), DARPins (designed ankyrin repeat proteins) (International PCT Patent Application Publication WO 02/20565) and anticalins (U.S. Pat. No. 7,250,297 and WO 99/16873). Verabodies are a further antibody mimetic technology. Versabodies (Amunix, US Patent Application Publication No. 2007/0191272) are small proteins, referred to as microproteins, of 3-5 kDa with greater than 15% cysteine residues, which form a high disulphide bond density scaffold which replaces the hydrophobic core which protein typically exhibit Avimers are another type of antibody mimetic. Avimers originate from the recombination of families of human serum proteins. They are single protein chains composed of modular binding domains, each of which is designed to bind to a particular target site. The avimers can bind simultaneously to sites on a single protein target and/or sites on multiple protein targets. Known as multi-point attachment or avidity, this binding mechanism mimics the way cells and molecules interact in the body, supports the generation of antagonists and agonists, and results in drugs with multiple functions and potent activity. Avimers libraries can be produced according to WO 2004/044011 incorporated herein by reference and for example US 2005/0053973. Avimers libraries are also available commercially from Avidia Inc, Mountain View, Calif., USA.

Antibody Production

The antibodies and binding members of the invention may be produced wholly or partly by chemical synthesis. For example, the antibodies and binding members of the invention can be prepared by techniques which are well known to the person skilled in the art, such as standard liquid peptide synthesis, or by solid-phase peptide synthesis methods. Alternatively, the antibodies and binding members may be prepared in solution using liquid phase peptide synthesis techniques, or further by a combination of solid-phase, liquid phase and solution chemistry.

The present invention further extends to the production of the antibodies or binding members of the invention by expression of a nucleic acid which encodes at least one amino acid which comprises an antibody of the invention in a suitable expression system, such that a desired peptide or polypeptide can be encoded. For example, a nucleic acid encoding the amino acid light chain and a second nucleic acid encoding an amino acid heavy chain can be expressed to provide an antibody of the present invention.

Accordingly, in certain further aspects of the invention, there is provided nucleic acids encoding amino acid sequences which form the antibodies or binding members of the present invention.

Typically, nucleic acids encoding the amino acid sequences which form antibodies or binding members of the present invention can be provided in an isolated or purified form, or provided in a form which is substantially free of material which can be naturally associated with it, with the exception of one or more regulatory sequences. Nucleic acid which expresses an antibody or binding member of the invention may be wholly or partially synthetic and may include, but is not limited to DNA, cDNA and RNA.

Nucleic acid sequences encoding the antibodies or binding members of the invention can be readily prepared by the skilled person using techniques which are well known to those skilled in the art, such as those described in Sambrook et al. "Molecular Cloning", A laboratory manual, cold Spring Harbor Laboratory Press, Volumes 1-3, 2001 (ISBN-0879695773), and Ausubel et al. Short Protocols in Molecular Biology. John Wiley and Sons, $4^{th}$ Edition, 1999 (ISBN-0471250929). Said techniques include (i) the use of the polymerase chain reaction (PCR) to amplify samples of nucleic acid, (ii) chemical synthesis, or (iii) preparation of cDNA sequences. DNA encoding antibodies or binding members of the invention may be generated and used in any suitable way known to those skilled in the art, including taking encoding DNA, identifying suitable restriction enzyme recognition sites either side of the portion to be expressed, and cutting out said portion from the DNA. The excised portion may then be operably linked to a suitable promoter and expressed in a suitable expression system, such as a commercially available expression system. Alternatively, the relevant portions of DNA can be amplified by using suitable PCR primers. Modifications to the DNA sequences can be made by using site directed mutagenesis.

Nucleic acid sequences encoding the antibodies or binding members of the invention may be provided as constructs in the form of a plasmid, vector, transcription or expression cassette which comprises at least one nucleic acid as described above. The construct may be comprised within a recombinant host cell which comprises one or more constructs as above. Expression may conveniently be achieved by culturing, under appropriate conditions, recombinant host cells containing suitable nucleic acid sequences. Following expression, the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells and NS0 mouse myeloma cells. A common, preferred bacterial host is *E. coli*. The expression of antibodies and antibody fragments in prokaryotic cells such as *E. coli* is well established in the art.

Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor. Techniques for the preparation of recombinant antibody molecules are described in the above references and also in, for example, European Patent Number 0,368,684.

In certain embodiments of the invention, recombinant nucleic acids comprising an insert coding for a heavy chain variable domain and/or for a light chain variable domain of antibodies or binding members are employed. By definition, such nucleic acids comprise encode single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

An antibody of the invention may be produced by recombinant means, not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, Ipp, or heat-stable enterotoxin II leaders.

The term "isolated", when used in reference to the caninised antibodies of the invention, or to binding members derived therefrom, or polypeptides which encode the same, refers to the state in which said antibodies, binding members or nucleic acids (polynucleotides) are provided in an isolated and/or purified form, that is they have been separated, isolated or purified from their natural environment, and are provided in a substantially pure or homogeneous form, or, in the case of nucleic acid, free or substantially free of nucleic acid or genes of origin other than the sequence encoding a polypeptide with the required function. Accordingly, such isolated antibodies, binding members and isolated nucleic acids will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo.

Antibodies, binding members and nucleic acids may be formulated with diluents or adjuvants and still, for practical purposes, be considered as being provided in an isolated form. For example the antibodies and binding members can be mixed with gelatin or other carriers if used to coat microtitre plates for use in immunoassays, or will be mixed with pharmaceutically acceptable carriers or diluents when used in diagnosis or therapy. The antibodies or binding members may be glycosylated, either naturally or by systems of heterologous eukaryotic cells (e.g. CHO or NSO cells, or they may be (for example if produced by expression in a prokaryotic cell) unglycosylated.

Heterogeneous preparations comprising anti-canine NGF caninised antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

Purification of Antibodies

Canine anti-NGF MAbs isotypes A, B, C and D are equipotent. Canine IgG isotypes A and D may be preferred for use in the present invention as these isotypes have a desirable lack of binding to complement. However, these isotypes do not bind *Staphylococcus* Protein A or Streptococcal Protein G and so cannot be purified using these common tools. The inventors of the present invention have identified two alternative methods which can be used to purify isotypes A and/or D. The first method comprises a combination of anion exchange chromatography, hydrophobic interaction chromatography and size exclusion chromatography. The second method comprises a combination of captoadhere affinity chromatography and anion exchange chromatography.

Pharmaceutical Compositions

Typically the pharmaceutical compositions of the invention are formulated in a liquid formulation, a lyophilized formulation, a lyophilized formulation that is reconstituted as a liquid, or as an aerosol formulation. In certain embodiments, the antibody in the formulation is at a concentration of: about 0.5 mg/ml to about 250 mg/ml, about 0.5 mg/ml to about 45 mg/ml, about 0.5 mg/ml to about 100 mg/ml, about 100 mg/ml to about 200 mg/ml, or about 50 mg/ml to about 250 mg/ml.

In certain embodiments, the formulation further comprises a buffer. Typically the pH of the formulation is from about pH 5.5 to about pH 6.5. In certain embodiments, the buffer may comprise from about 4 mM to about 60 mM histidine buffer, about 5 mM to about 25 mM succinate buffer, or about 5 mM to 25 mM acetate buffer. In certain embodiments, the buffer comprises sodium chloride at a concentration of from about 10 mM to 300 mM, typically at around 125 mM concentration and sodium citrate at a concentration of from about 5 mM to 50 mM, typically 25 mM. In certain embodiments the formulation can further comprise a surfactant at a concentration of just above 0% to about 0.2%. In certain embodiments the surfactant is selected from the group consisting of, but not limited to: polysorbate-20, polysorbate-40, polysorbate-60, polysorbate-65, polysorbate-80, polysorbate-85, and combinations thereof. In a preferred embodiment, the surfactant is polysorbate-20 and may further comprise sodium chloride at a concentration of about 125 mM and sodium citrate at a concentration of about 25 mM.

Administration

The antibodies or binding members of the present invention may be administered alone but will preferably be administered as a pharmaceutical composition which will generally comprise a suitable pharmaceutically acceptable excipient, diluent or carrier selected depending on the intended route of administration. Examples of suitable pharmaceutical carriers include; water, glycerol, ethanol and the like.

The monoclonal antibody or binding member of the present invention may be administered to a canine patient in need of treatment via any suitable route. Typically, the composition can be administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal, rectal.

In embodiments where the composition is delivered as an injectable composition, for example in intravenous, intradermal or subcutaneous application, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The antibodies and compositions of the invention are typically administered to a subject in a "therapeutically effective amount", this being an amount sufficient to show benefit to the subject to whom the composition is administered. The actual dose administered, and rate and time-course of administration, will depend on, and can be determined with due reference to, the nature and severity of the condition which is being treated, as well as factors such as the age, sex and weight of the subject being treated, as well as the route of administration. Further due consideration should be given to the properties of the composition, for example, its binding activity and in-vivo plasma life, the concentration of the antibody or binding member in the formulation, as well as the route, site and rate of delivery.

Dosage regimens can include a single administration of the antibody or composition of the invention, or multiple administrative doses of the antibody or composition. The antibody or antibody containing compositions can further be administered sequentially or separately with other therapeutics and medicaments which are used for the treatment of the condition for which the antibody or binding member of the present invention is being administered to treat.

Examples of dosage regimens which can be administered to a subject can be selected from the group comprising, but not limited to; 1 µg/kg/day through to 20 mg/kg/day, 1 µg/kg/day through to 10 mg/kg/day, 10 µg/kg/day through to 1 mg/kg/day. In certain embodiments, the dosage will be such that a plasma concentration of from 1 µg/ml to 100 µg/ml of the antibody is obtained. However, the actual dose of the composition administered, and rate and time-course of administration, will depend on the nature and severity of the condition being treated. Prescription of treatment, e.g. decisions on dosage etc, is ultimately within the responsibility and at the discretion of veterinary practitioners and other veterinary doctors, and typically takes account of the disorder to be treated, the condition of the individual patient, the site of delivery, the method of administration and other factors known to practitioners.

Definitions

Unless otherwise defined, all technical and scientific terms used herein have the meaning commonly understood by a person who is skilled in the art in the field of the present invention. The meaning and scope of the terms should be clear, however, in the event of any ambiguity, definitions provided herein take precedent over any dictionary or extrinsic definition.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like. Further, unless otherwise required by context, singular terms shall include pluralities and plural terms shall include the singular.

As herein defined, the term "pain" means an unpleasant sensory and emotional experience associated with actual or potential tissue damage, or described in terms of such damage.

In relation to operative or post-operative pain, the US Animal Welfare Act (Animal Welfare Act 2002. AWA regulations, CFR, Title 9 (Animals and Animal Products), Chapter 1 (Animal and Plant Health Inspection Service, Department of Agriculture). Subchapter A (Animal Welfare), Parts 1-4) defines a painful procedure as any procedure that would reasonably be expected to cause more than slight or momentary pain or distress in a human being to which that procedure was applied, that is, pain in excess of that caused by injections or other minor procedures. Therefore, if a canine undergoes a painful surgical procedure, the animal should receive postoperative analgesics.

In further instance, a canine may be experiencing significant or chronic pain as a result of an associated medical condition such as rheumatoid arthritis, osteoarthritis, inflammation or a cancerous or malignant condition.

The term "nociception" refers to the perception of noxious stimuli. As herein defined "neuropathic pain" (also known as 'neuralgia') is a pain that comes from problems with signals from the nerves. It may arise as a consequence of a lesion or disease affecting the somatosensory system. There are causes of neuropathic pain and it may be associated with abnormal sensations called dysesthesia, which occur spontaneously. Alternatively, it may be associated with allodynia which results when the pain comes on, or gets worse, with a touch or stimulus that would not normally cause pain. For example, a slight touch on the face may trigger pain if you have trigeminal neuralgia, or the pressure of the bedclothes may trigger pain if you have diabetic neuropathy. Neuropathic pain may also result from allodynia, where the pain comes on, or gets worse, with a touch or stimulus that would not normally cause pain. For example, a slight touch to the face may trigger pain if a subject has trigeminal neuralgia. Neuropathic pain relating to hyperalgesia means that severe pain results from a stimulus or touch that would normally cause only slight discomfort, while paresthesia means that uncomfortable or painful feelings occur even when there is nothing in contact with the area causing the pain, for example pins and needles. Other forms of neuropathic pain involve pruritis or itch, which can be associated with allergic or inflammatory responses in the skin and inflammatory pain resulting from tissue damage and repair processes.

As defined herein, the term "NGF neutralising antibody" or similar describes an antibody that is capable of neutralising the biological activation and signalling of NGF. The neutralising antibody, which may also be referred to as an antagonistic antibody, or a blocking antibody, specifically, and preferably selectively, binds to NGF and inhibits one or more biological activities of NGF. For example, the neutralising antibody may inhibit the binding of a NGF to its target ligand, such as the cell membrane bound TrkA or p75 receptors.

As used herein, the term "biological activity" refers to any one or more inherent biological properties of a molecule (whether present naturally as found in vivo, or provided or enabled by recombinant means). Biological properties include but are not limited to receptor binding and/or activation; induction of cell signalling or cell proliferation, inhibiting cell growth, induction of cytokine production, induction of apoptosis, and enzymatic activity.

The term "complementarity determining region (CDR)", as used herein, refers to amino acid sequences which together define the binding affinity and specificity of the natural Fv region of a native immunoglobulin binding site as delineated by Kabat et al. (Kabat, E. A., Wu, T. T., Perry, H., Gottesman, K. and Foeller, C. (1991) Sequences of Proteins of Immunological Interest, Fifth Edition. NIH Publication No. 91-3242). The term "framework region (FR)", as used herein, refers to amino acid sequences interposed between CDRs. These portions of the antibody serve to hold the CDRs in appropriate orientation (allows for CDRs to bind antigen).

The term "constant region (CR)" as used herein, refers to the portion of the antibody molecule which confers effector functions. In the present invention, constant regions typically mean canine constant regions, that is that the constant regions of the subject canininsed antibodies are derived from canine immunoglobulins. The heavy chain constant region can be selected from any of the four isotypes: A, B, C or D.

The term "chimeric antibody" as used herein refers to an antibody containing sequences derived from two different antibodies, which typically are of different species. Most typically chimeric antibodies comprise variable domains derived from a donor specifies which bind specifically to a target epitope and constant domains derived from antibodies obtained from the target species to whom the antibody is to be administered.

The term "immunogenicity" as used herein refers to a measure of the ability of a targeting protein or therapeutic moiety to elicit an immune response (humoral or cellular) when administered to a recipient. The present invention is concerned with the immunogenicity of the subject caninised antibodies. Preferably the antibodies of the present invention have no immunogenicity, that is that no neutralising antibodies will be raised against them when administered to a canine, and further, no effector functions are mediated by the Fc regions of the antibody.

The term "identity" or "sequence identity" as used herein, means that at any particular amino acid residue position in an aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This may be referred to as conservative substitution. Preferably when the amino acid sequences of the invention are modified by way of conservative substitution of any of the amino acid residues contained therein, these changes have no effect on the binding specificity or functional activity of the resulting antibody when compared to the unmodified antibody.

Sequence identity with respect to a (native) polypeptide of the invention and its functional derivative relates to the percentage of amino acid residues in the candidate sequence which are identical with the residues of the corresponding native polypeptide, after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology. Methods and computer programs for performing an alignment of two or more amino acid sequences and determining their sequence identity or homology are well known to the person skilled in the art. For example, the percentage of identity or similarity of 2 amino acid sequences can be readily calculated using algorithms e.g. BLAST (Altschul et al. 1990), FASTA (Pearson & Lipman 1988), or the Smith-Waterman algorithm (Smith & Waterman 1981).

As used herein, reference to an amino acid residue having the "highest homology" to a second amino acid residue refers to the amino acid residue which has the most characteristics or properties in common with the second amino acid residue. In determining whether an amino acid residue has the highest homology to a second amino acid residue, an assessment may typically be made of factors such as, but not limited to, charge, polarity, hydrophobicity, side arm mass and side arm dimension.

The term "corresponding position" as used herein to refer to an amino acid residue that is present in a second sequence at a position corresponding to a specified amino acid residue in a first sequence is intended to refer to the position in the second sequence which is the same position as the position in the first sequence when the two sequences are aligned to allow for maximum sequence identity between the two sequences. Amino acid residues at corresponding positions have the same Kabat numbering.

The term "consists essentially of" or "consisting essentially of" as used herein means that a polypeptide may have additional features or elements beyond those described provided that such additional features or elements do not materially affect the ability of the antibody or antibody fragment to have binding specificity to canine NGF. That is, the antibody or antibody fragments comprising the polypeptides may have additional features or elements that do not interfere with the ability of the antibody or antibody fragments to bind to canine NGF and antagonise canine NGF functional activity. Such modifications may be introduced into the amino acid sequence in order to reduce the immunogenicity of the antibody. For example, a polypeptide consisting essentially of a specified sequence may contain one, two, three, four, five or more additional, deleted or substituted amino acids, at either end or at both ends of the sequence provided that these amino acids do not interfere with, inhibit, block or interrupt the role of the antibody or fragment in binding to canine NGF and sequestering its biological function. Similarly, a polypeptide molecule which contributes to the canine NGF antagonistic antibodies of the invention may be chemically modified with one or more functional groups provided that such functional groups do not interfere with the ability of the antibody or antibody fragment to bind to canine NGF and antagonise its function.

As used herein, the term "effective amount" or "therapeutically effective amount" means the amount of an agent, binding compound, small molecule, fusion protein or peptidomimetic of the invention which is required to suppress canine NGF binding to the p75 and/or TrkA receptors.

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide.

As herein defined an "antibody" encompasses antigen-binding proteins which specifically bind to a target antigen of interest, in this case canine nerve growth factor, having one or more polypeptides that can be recombinantly prepared or which are genetically encodable by immunoglobulin genes, or fragments of immunoglobulin genes. The term "antibody" encompasses monoclonal and chimeric antibodies, in particular caninised antibodies, and further encompasses polyclonal antibodies or antibodies of any class or subtype. An "antibody" further extends to hybrid antibodies, bispecific antibodies, heteroantibodies and to functional fragments thereof which retain antigen binding.

The phrase "specifically binds to" refers to the binding of an antibody to a specific protein or target which is present amongst a heterogeneous population of proteins. Hence, when present in specific immunoassay conditions, the antibodies bind to a particular protein, in this case canine NGF, and do not bind in a significant amount to other proteins present in the sample.

As defined herein, a "canine" may also be referred to as a "dog". Canines can be categorised as belonging to the subspecies with the trinomial name *Canis lupus familiaris* (*Canis familiaris domesticus*) or *Canis lupus dingo*. Canines include any species of dog and includes both feral and pet varieties, the latter also being referred to as companion animals.

The present invention will now be described with reference to the following examples which are provided for the purpose of illustration and are not intended to be construed as being limiting on the present invention. The methods and techniques of the present invention are generally performed according to conventional methods well known in the art and as described in various general and more specific references that are cited and discussed throughout the present specification unless otherwise indicated.

EXAMPLES

Example 1—Production of Antibodies

Whole antibody sequences were produced by combining caninised variable domain sequences with C-terminal canine constant heavy or constant light chain sequences. Four distinct immunoglobulin gamma (IgG) heavy chain constant domain isotypes have been described in the canine immune system (Tang L. et al. 2001. Veterinary Immunology and Immunopathology, 80. 259-270) along with single kappa and lambda constant domain sequences.

The caninised αD11 VH domain was combined with each of the four IgG heavy chain isotypes A, B, C and D and the caninised αD11 VL domain with the canine kappa light chain constant domain. The sequences of the full-length mature antibody chains (caN) are shown in SEQ ID 5 (VL1 and canine kappa constant domain), 6 (VH1 and heavy chain isotype A), 7 (VH1 and heavy chain isotype B), 8 (VH1 and heavy chain isotype C) and 9 (VH1 and heavy chain isotype D). The sequence of a light chain of a variant antibody (caN2) is shown in SEQ ID No:10 (light chain variant (VL2) and canine kappa constant domain). The amino acid sequences for heavy chains of a variant antibody (caN2) are provided in SEQ ID NO:11 (HCA variant—VH2 and heavy chain isotype A), SEQ ID NO:12 (HCB variant—VH2 and heavy chain isotype B), SEQ ID NO:13 (HCC variant—VH2 and heavy chain isotype C) and SEQ ID NO:14 (HCD variant—VH2 and heavy chain isotype D).

The combined amino acid sequences were converted to expressible form in mammalian cells by the optimal selection of codons and full chemical gene synthesis and cloning into a mammalian cell expression vector pcDNA3.1+.

The resultant cDNAs were transfected into CHO cells and the supernatants from heavy chains having the sequences SEQ ID NO:6-9 were analysed in Example 2. Antibodies having the light chain sequence SEQ ID NO:10 and the heavy chain sequence SEQ ID NO:11 were purified in Example 11.

Example 2—Determining Binding of Antibodies to Murine and Canine NGF

Combinations of caninised heavy and light chain cDNAs were transfected into CHO cells, the supernatants harvested and reacted in ELISA format with either canine or murine NGF. Following incubation and wash steps, the bound canine antibody was detected by reactivity with a goat-anti canine IgG specific polyclonal antibody linked to horseradish peroxidase (HRP) and developed using TMB. The optical density of the resulting product was measured at 450 nm and compared with that from mock empty vector transfected supernatant (denoted as "Mock" in FIG. 1).

The results are shown in the graph of FIG. 1. Binding to mouse NGF is shown for 4 caninised antibodies. Each of these antibodies has the same light chain (caN-kLC-1), that is a light chain comprising a canine kappa constant domain. Each antibody has a different heavy chain constant domain. Accordingly a specific heavy chain variable domain is combined with one of 4 different constant domains (caN-HCA, caN-HCB, caN-HCC or caN-HCD). In the second part of the graph, binding of a single antibody comprised of the caN-kLC-1 light chain and the caN-HCB constant chain to canine NGF is shown.

Example 3—Purification of Caninised Antibodies

The supernatants obtained from Example 2 were purified using a Protein A column, separated by SDS-PAGE and tested for reactivity to the anti-canine IgG polyclonal antibody HRP. This polyclonal antibody preferentially recognises the heavy chains.

Figure 2:
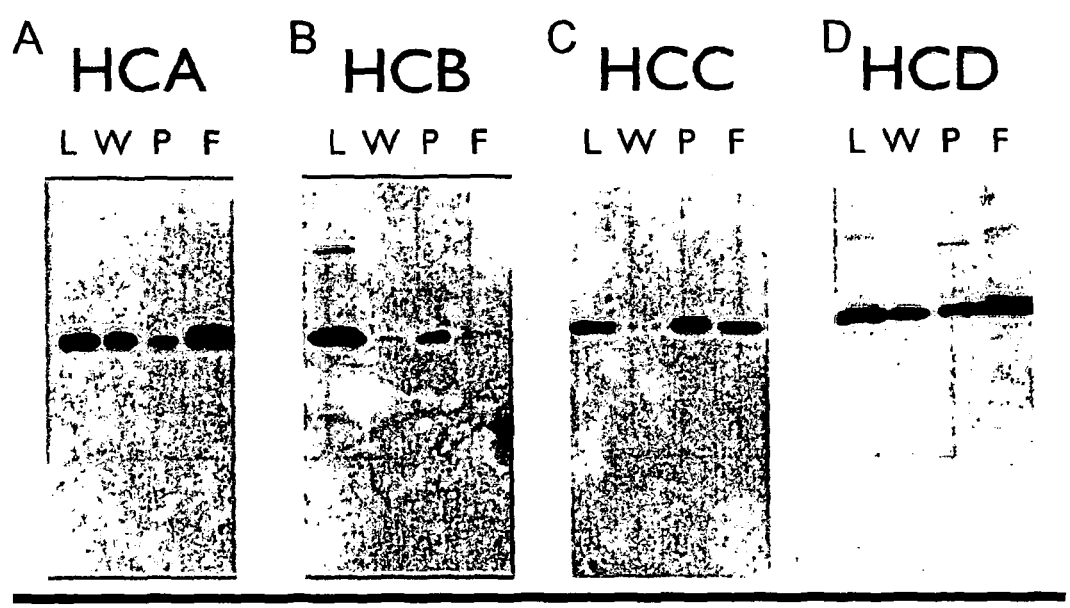
FIG. 2A-D shows a series of gels showing protein A purification of the caninised antibodies of the invention.

The results are shown in FIG. 2 A-D. Legend: A—HCA is a caninised antibody comprising the caN-HCA heavy chain and caN-kLC light chain, HCB is a caninised antibody comprising the caN-HCB heavy chain and the caN-kLC light chain, C—HCC is a caninised antibody comprising the caN-HCC heavy chain and a caN-kLC light chain, D—HCD is a caninised antibody comprising the caN-HCA heavy chain and a caN-kLC light chain. With each of FIGS. 2A-D, L means load, W means wash, P means peak fraction, and F means flow through.

It can be seen that Protein A preferentially binds to the HCB isotype (i.e. a caninised antibody comprising the caN-HCB heavy chain), whereas significant material is not retained and is easily washed off of Protein A by the HCA, HCC and HCD isotypes.

Example 4—Analysis of Purified Caninised Antibodies Using SDS-PAGE

Representative fractions of the peaks from the gels shown in Example 2 (FIGS. 2A-D) were separated by SDS-PAGE and stained with Coomassie blue.

Figure 3:
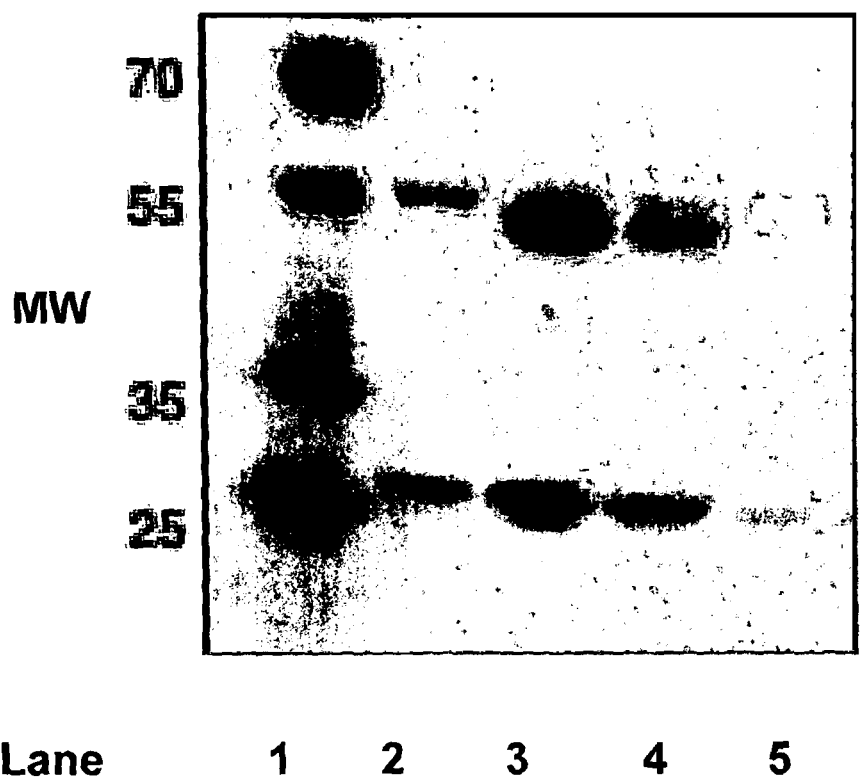
FIG. 3 shows a gel showing the results of purification of caninised antibodies using SDS-Page.

The results are shown in the gel shown in FIG. 3. This gel shows that heavy and light chains are clearly visible. Order of lanes from left: Lane 1—Size standards, Lane 2—HCA caN-HCA+caN-kLC1, Lane 3—HCB caN-HCB+caN-kLC1, Lane 4—HCC caN-HCC+caN-kLC1, Lane 5—HCD caN-HCA+caN-kLC.

Example 5—Inhibition of NGF Induced Proliferation of TF-1 Cells by Caninised Antibodies Serial dilutions of CHO cell transfectant supernatants from Example 2 ("antagonist") were incubated with TF-1 cells in the presence of 0.3 ng/mL NGF. The resultant proliferation was measured by thymidine incorporation.

Figure 4:
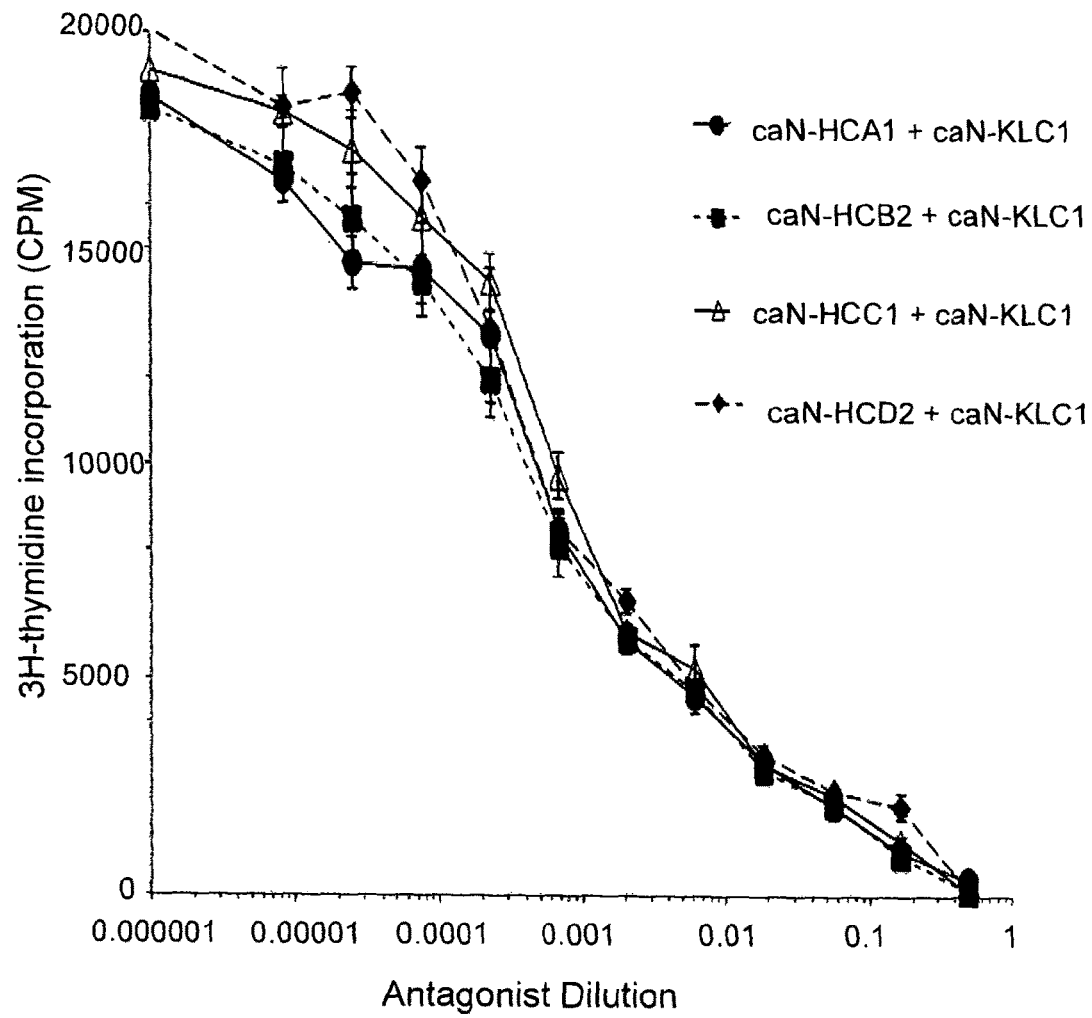
FIG. 4 shows a graph showing the inhibition of NGF induced proliferation of TF-1 cells by caninised antibodies.

The results are shown in FIG. 4. 50% inhibition was observed at a calculated 0.75-1.5 ng/mL monoclonal antibody (MAb).

Example 6—Complement Deposition Induced by Antigen-Captured Caninised Antibodies CHO cell transfectant supernatants from Example 2 were incubated with plates coated with 0.1 ng/mL NGF to capture the antibodies. The plates were washed and then incubated with human serum and bound complement C1q was measured by binding of anti-human C1q polyclonal antibody HRP and developed as above.

Complement Binding Method

Plates were coated with 100 µl/well of 5 µg/ml mouse NGF and blocked with 5% BSA/PBS. Coated wells were incubated for 1 hour at room temperature with cell culture supernatants, containing recombinant caninised anti-NGF IgG, diluted in PBS/1% BSA (100 µl/well). The plates were washed and incubated for 1 hour at room temperature with 100 µl/well of human serum diluted 1/100 in veronal buffered saline containing 0.5 mM $MgCl_2$, 2 mM $CaCl_2$, 0.05% Tween-20, 0.1% gelatin and 0.5% BSA. After washing, plates were incubated with 100 µl of a 1/800 dilution of sheep anti-C1q-HRP (Serotec) in PBS/1% BSA. After washing, plates were developed by the addition of 100 µl TMB substrate (Thermo Scientific). Development was stopped by the addition of 100 µl of 2N $H_2SO_4$ and absorbance read at 450 nm.

Figure 5:
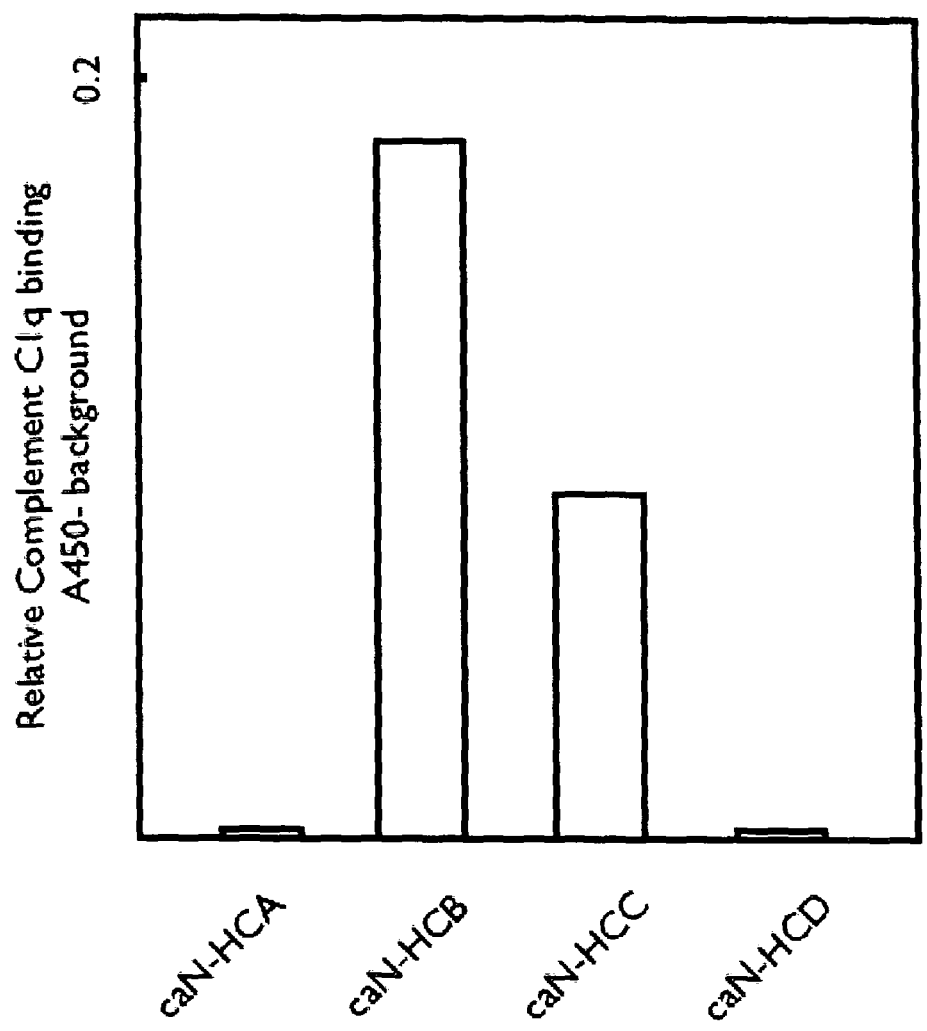
FIG. 5 shows a graph showing complement deposition induced by antigen-captured caninised antibodies.

The results are shown in the graph of FIG. 5. These results show binding of C1q to immobilised caninised HCB and HCC type antibodies and no binding of C1q to caninised HCA and HCD type antibodies. Hence, the results surprisingly indicate that different canine derived heavy chains exhibit different complement binding and activation characteristics and that the caninised antibodies with type HCA and HCD heavy chains have been unexpectedly shown to be preferable for use in antagonising canine NGF. The identification of canine derived heavy chains which do not mediate complement fixing is a particularly advantageous finding as NGF is a soluble mediator.

Example 7—Comparison of the Binding of Anti-Canine-NGF Monoclonal Antibodies to NGF A comparison of the binding of anti-canine-NGF monoclonal antibodies to NGF using frameworks VL1 and VH1 (SEQ ID NO:1 and 2) versus alternate frameworks VL2 and VH2 (SEQ ID NO:3 and 4) was carried out. DNA encoding the light and heavy chains described by SEQ ID NO:10 and SEQ ID NO:11 were synthesised and cloned into pcDNA3.1+ downstream of secretory signal sequence peptides. The DNAs were co-transfected into CHO cells and the supernatant compared by binding ELISA to mouse NGF with CHO supernatant from co-expression of SEQ ID NO:5 plus SEQ ID NO:7.

Figure 13A:
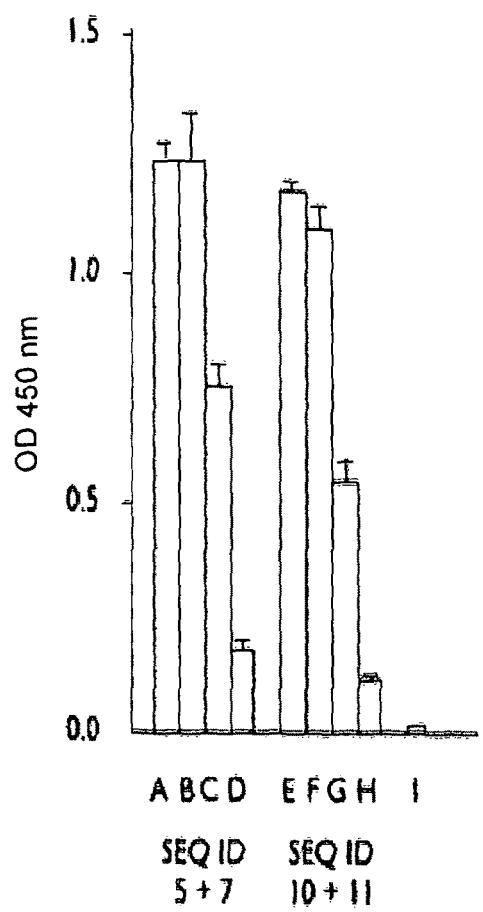
FIG. 13A shows a graph showing the comparison of binding to NGF of anti-canine-NGF monoclonal antibodies using varying dilutions of SEQ ID No: 5 and 7 and SEQ ID No: 10 and 11.

The results are shown in FIG. 13A. Lanes A-D show supernatant (undiluted, 1/10, 1/100, 1/1000 respectively) from SEQ ID NO:5 and SEQ ID NO:7. Lanes E-H show supernatant (undiluted, 1/10, 1/100, 1/1000 respectively) from SEQ ID NO:10 and SEQ ID NO:11. Lane I shows an undiluted negative control supernatant.

Example 8—Complement Deposition Induced by NGF-Captured Caninised Antibodies CHO cell transfectant supernatants from Example 7 were tested for their ability to recruit complement using a C1q ELISA assay (using the method described in FIG. 5).

Figure 13B:
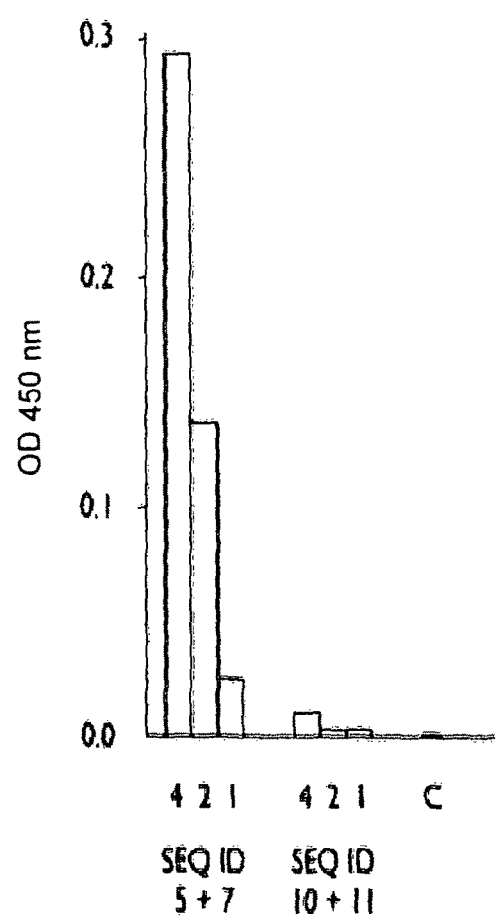
FIG. 13B shows a graph showing complement deposition of the supernatants from FIG. 13A.

The results are shown in FIG. 13B. The combination of VL2 (in SEQ ID 10) and VH2 frameworks plus HCA type constant domains (SEQ ID 11) was inactive at recruiting complement despite equivalent binding to NGF observed in Panel A to that of the HCB type heavy chain in MAb (SEQ ID 5+7). The MAbs were tested in a dilution series of 4, 2 and 1 ug/ml. C was a negative control.

Example 9—Comparison of Binding to NGF of N-Glycosylated and Aglycosylated Variants of Anti-Canine-NGF Monoclonal Antibodies with HCB and HCC Heavy Chain Isotypes A comparison of the binding of N-glycosylated and aglycosylated variants of anti-canine-NGF monoclonal antibodies to NGF with HCB and HCC heavy chain isotypes was carried out. Expression vectors encoding the light and heavy chain pairs described by SEQ ID NO:5 and SEQ ID NO:7 (HCB), SEQ ID NO:5 and SEQ ID NO:16 (HCB*), SEQ ID NO:5 and SEQ ID NO:8 (HCC), or SEQ ID NO:5 and SEQ ID NO:17 (HCC*) were co-transfected into CHO cells and the supernatants compared by binding ELISA to mouse NGF.

The results are shown in FIG. 14A. The white boxes show undiluted supernatant, the shaded boxes show a 1/100 dilution and C shows an undiluted negative control supernatant. Equivalent binding to NGF was observed.

Example 10—Complement Deposition Induced by NGF-Captured Caninised Antibodies CHO cell transfectant supernatants from Example 9 were tested for their ability to recruit complement using a C1q ELISA assay (using the method described in FIG. 5).

The results are shown in FIG. 14B. The ability to recruit complement C1q was abolished by removal of the N-linked glycosylation site in the B type heavy chain (HCB*) and was diminished by a similar mutation in the C type heavy chain (HCC*).

Accordingly, it is demonstrated herein, quite surprisingly, that where an antibody of the invention has a canine derived heavy chain of the HCA or HCD subtype, the binding of the antibody to canine NGF does not result in complement activation or other downstream effector functions, such as ADCC. Hence, said antibodies, in antagonising the biological functional activity of canine NGF by preventing binding of canine NGF to the membrane bound TrkA or p75 receptors, inhibit the associated downstream intracellular signalling cascade. Furthermore, as NGF expression frequently occurs in the proximity of nerves and the like, the NGF antagonising or neutralising antibodies of the invention, which have canine derived heavy chain of the HCA or HCD subtype, can sequester canine NGF biological activity without recruiting a wider immune response. Such functional properties are unexpected, yet highly desirable.

Example 11—Purification of Anti-NGF Monoclonal Antibodies Following Expression in CHO Cells Since canine anti-NGF monoclonal antibodies of the HCA and HCD isotypes have desirable lack of binding to complement (FIG. 5), but bind weakly to *Staphylococcus* Protein A (FIG. 2), alternative methods of purification were developed. Anti-canine NGF monoclonal antibodies derived from expression vectors expressing SEQ ID NO:10 (light chain variant (VL2) and canine kappa constant domain) and SEQ ID NO:11 (HCA variant—VH2 and heavy chain isotype A) were expressed in CHO cells and following extensive experimentation it was found that the canine anti-NGF antibody could be fractionated to high purity by two alternative purification methods.

Figure 15A:
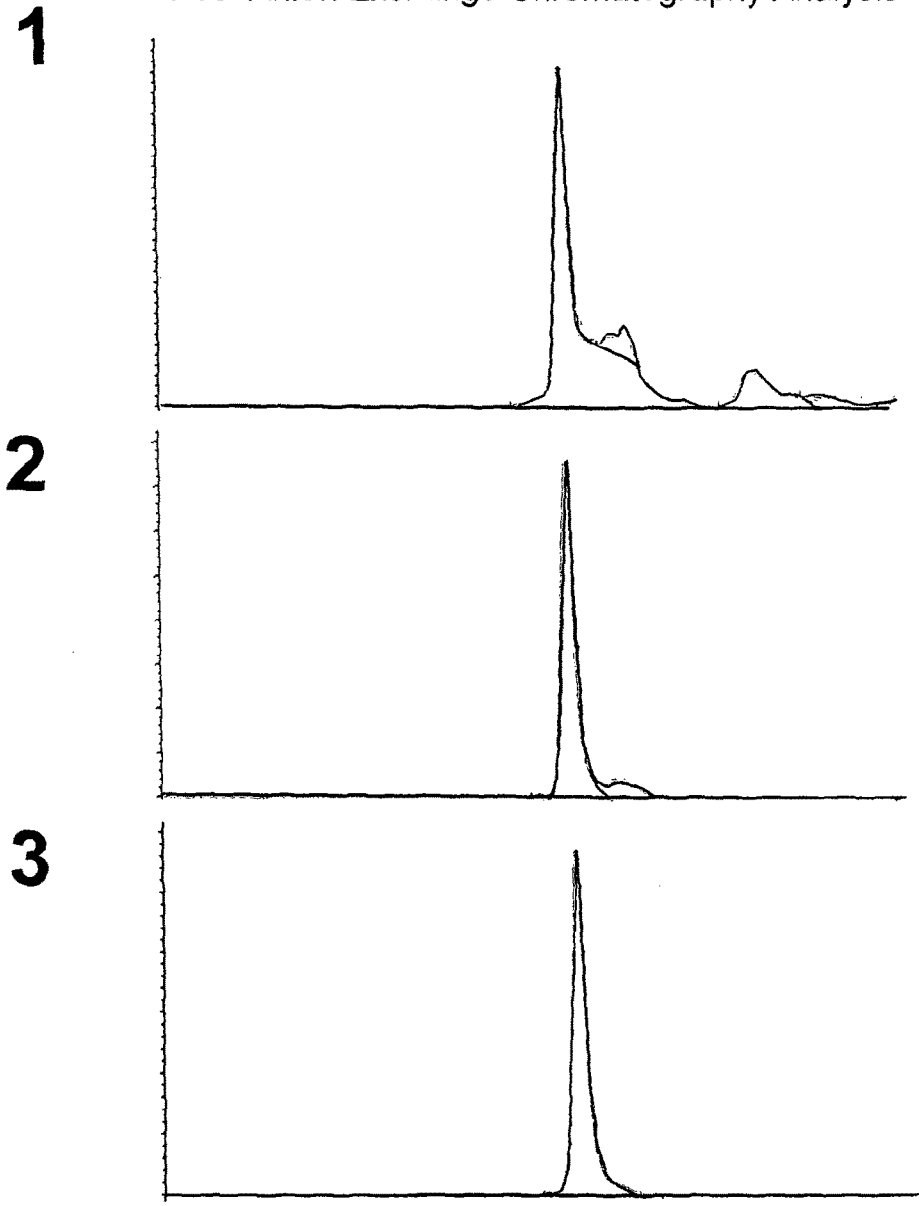
FIGS. 15A and B show the quantitative purification of the anti-canine NGF antibodies of the present invention using a three-step method (Method I) comprising (1) anion exchange chromatography, (2) hydrophobic interaction chromatography and (3) size exclusion chromatography.
Figure 15B:
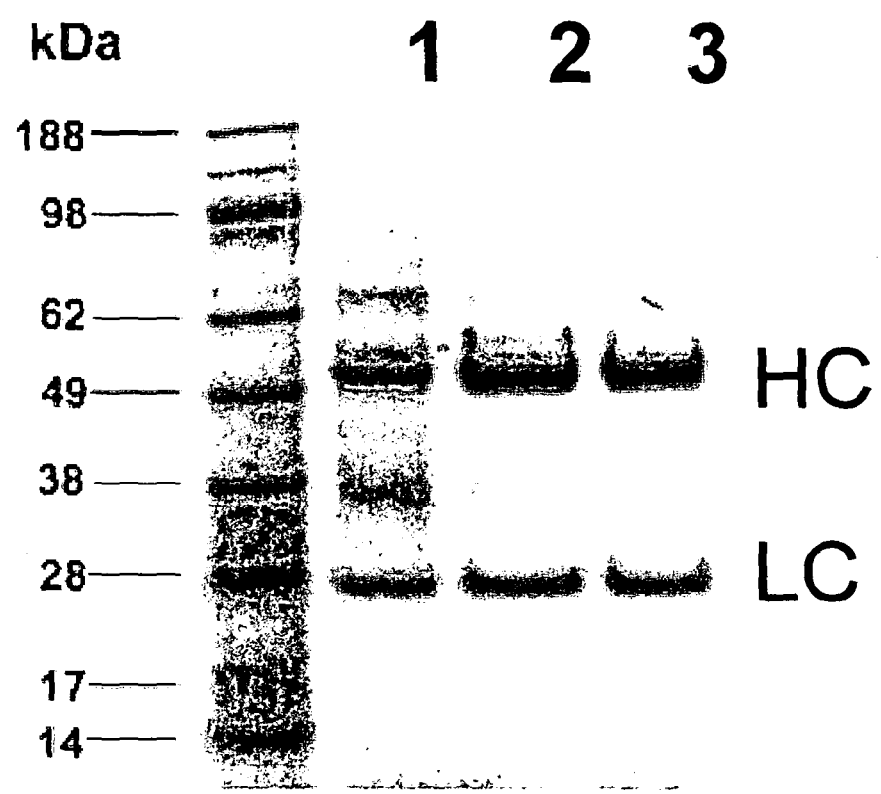
FIG. 15B shows a reducing SDS-PAGE gel of fractions following each step.
Figure 15C:
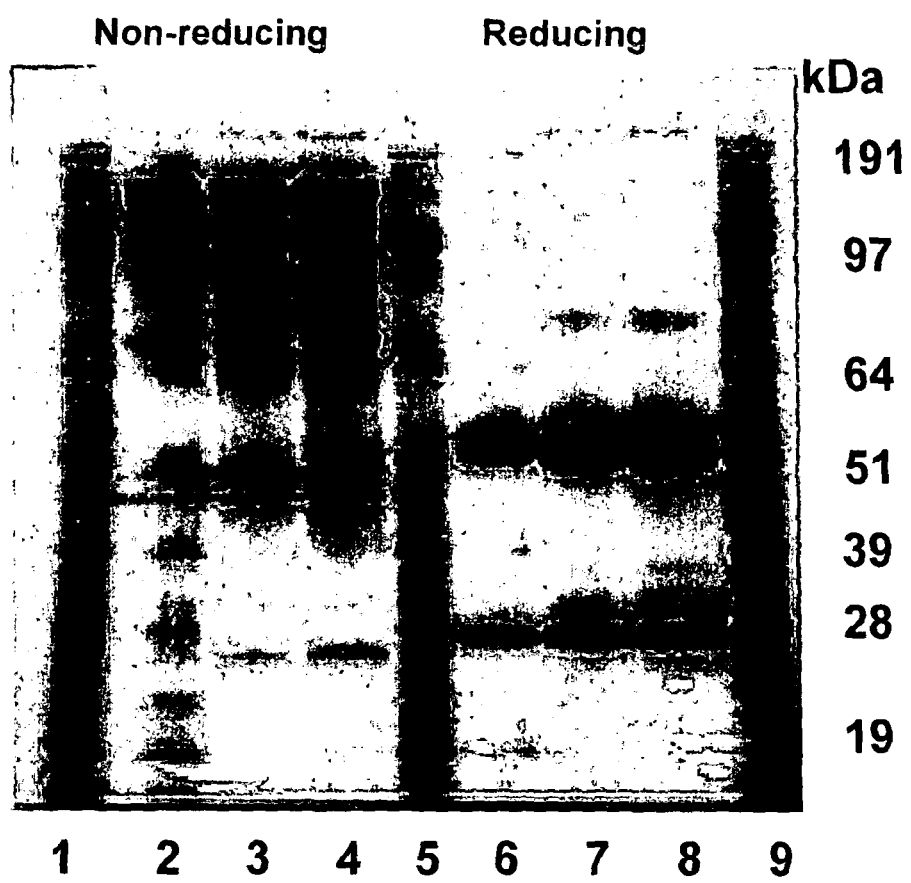
FIGS. 15C and D show the quantitative purification of the anti-canine NGF antibodies of the present invention using a two-step method (Method II) comprising Captoadhere chromatography and anion exchange chromatography.
Figure 15D:
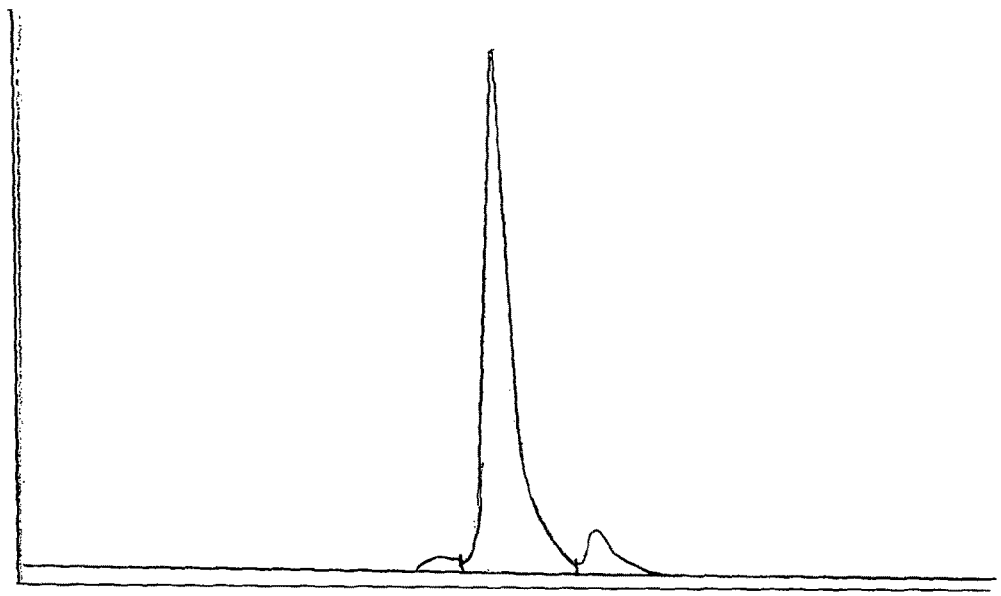
FIG. 15D: size exclusion chromatography.

In the first method, anti-canine NGF monoclonal antibody was purified by anion exchange chromatography, hydrophobic interaction chromatography and size exclusion chromatography (Method I—FIGS. 15A and B). In the second method, the anti-NGF antibody could be purified by Captoadhere affinity chromatography followed by anion exchange chromatography (Method II—FIGS. 15C and D).

Figure 16A:
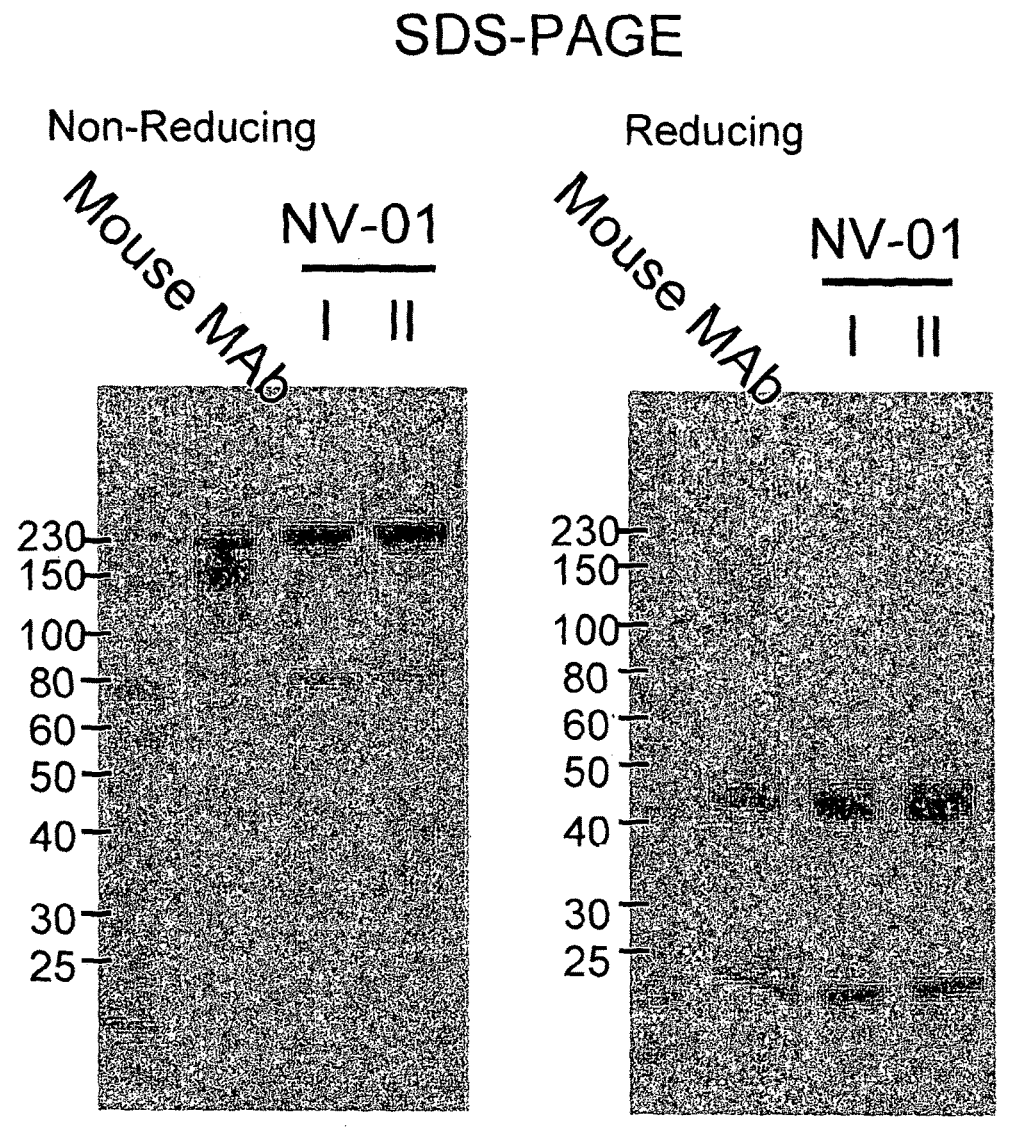
Figure 16B:
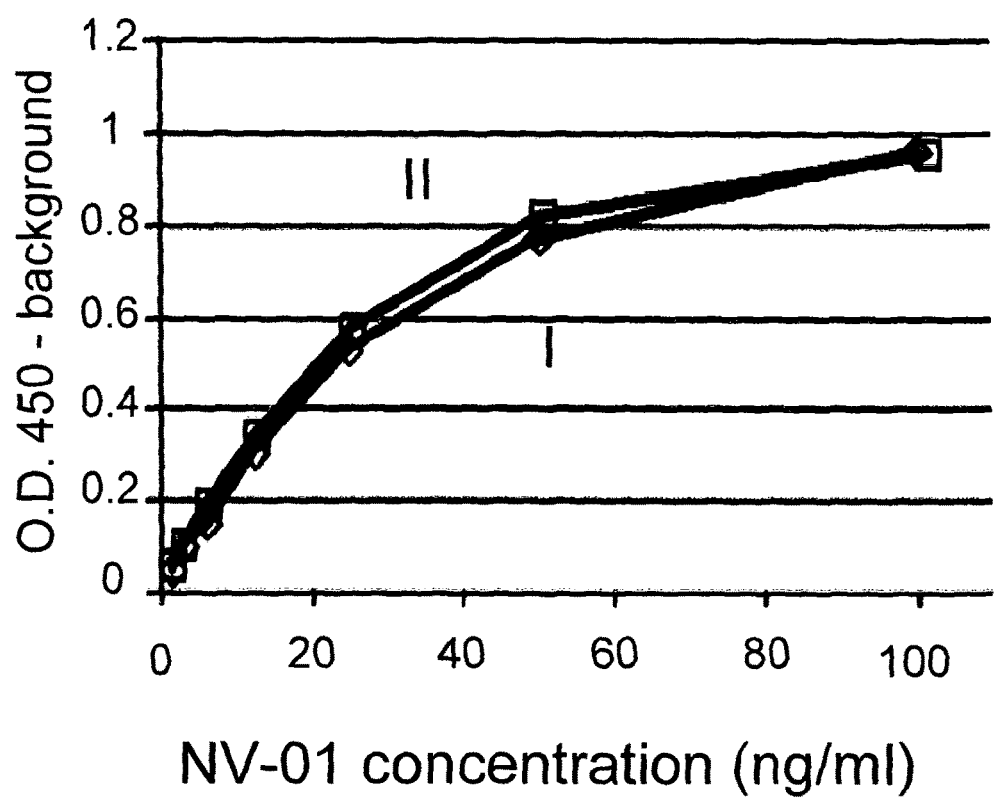
FIG. 16B: comparison by anti-NGF ELISA.

The main peak of anti-NGF monoclonal antibody purified by either method corresponds to a molecular weight of approximately 150 kDa. Comparison by SDS-PAGE and ELISA (FIG. 16) illustrates that Methods I and II produce antibody preparations with similar purity and bioactivity. Purified anti-NGF monoclonal antibodies produced by these methods were tested in the TF-1 NGF neutralisation assay (described in FIG. 4) and shown to have high potency (IC50 13 pM anti-NGF neutralised 37 μM NGF; not shown).

Example 12—Anti-Canine NGF Monoclonal Antibodies can be Safely Administered Intravenously to Canines and do not Cause Pyrexia Anti-canine NGF monoclonal antibodies derived from expression vectors expressing SEQ ID NO:10 and SEQ ID NO:11 (canine HCA type heavy chain) were expressed in CHO cells and purified by a combination of ion exchange chromatography, hydrophobic interaction chromatography and size exclusion chromatography (Method I, FIGS. 15A and B) and buffer exchanged into phosphate buffered saline. The antibodies were injected intravenously into beagle dogs at 2 mg/kg body weight and assessed for signs of toxicity by visual inspection by a veterinarian, change in body weight, body temperature and plasma biochemistry. FIG. 17 illustrates the body weight and temperature measurements. No changes were observed in these or any plasma biochemistry analyte measured (including sodium, potassium, chloride, calcium, phosphate, urea, creatinine, glucose, cholesterol, bilirubin, alanine transaminase, alkaline phosphatase, amylase, lipase, total protein or albumin: not shown).

Figure 18:
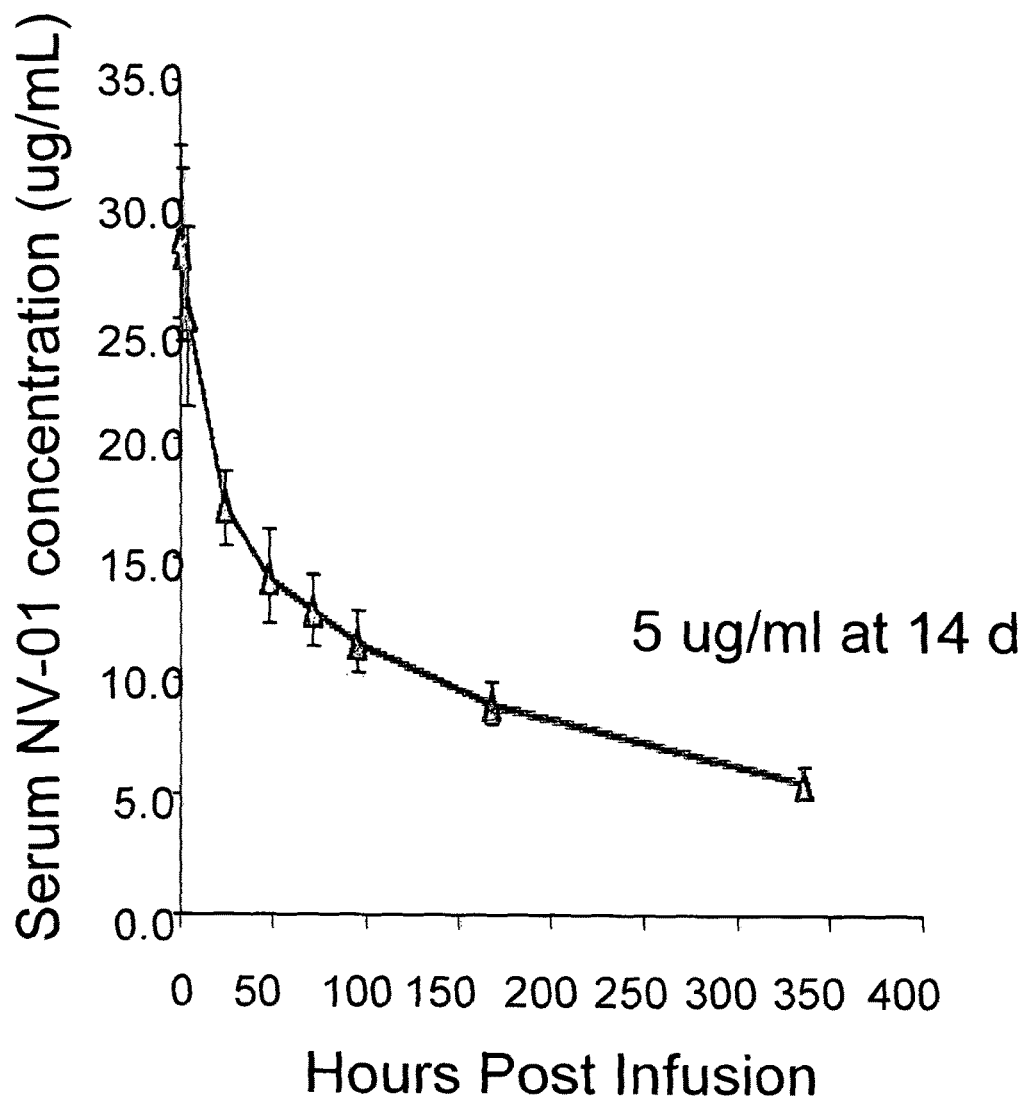
FIG. 18 shows kinetic analysis of plasma anti-canine NGF monoclonal antibody concentration following intravenous injection to a dog. A beagle dog was injected intravenously with anti-NGF antibody at 2 mg/kg, samples of plasma were taken at the times indicated and anti-NGF monoclonal antibody was detected by NGF ELISA. The anti-canine NGF monoclonal antibody had a surprisingly long elimination (beta) phase half life of approximately 9 days.

Example 13—Plasma Pharmacokinetics of Anti-Canine NGF Monoclonal Antibodies In Vivo Demonstrates Long Serum Half-Life and Lack of Immunogenicity Anti-canine NGF monoclonal antibodies derived from expression vectors expressing SEQ ID NO:10 and SEQ ID NO:11 (canine HCA type heavy chain) were expressed in CHO cells and purified by a combination of ion exchange chromatography, hydrophobic interaction chromatography and size exclusion chromatography and buffer exchanged into phosphate buffered saline (Method 1, FIGS. 15A and B). The antibodies were injected intravenously into beagle dogs at 2 mg/kg body weight and plasma samples were taken at various times over the following 2 weeks. Diluted plasma samples were assessed for anti-canine NGF antibody concentration by ELISA using NGF as target and anti-canine polyclonal antibody-horseradish peroxidase secondary reagent and developed as per FIG. 1. The results are shown in FIG. 18. The plasma concentrations measured were consistent with two-phase kinetics, with a tissue distribution (alpha) phase half-life of approximately 33 hours and surprisingly long elimination (beta) phase of approximately 9 days.

The absence of a sharp decline in plasma concentration of anti-canine NGF antibody concentration between 100 and 300 hours demonstrates that there are neither pre-existing neutralising antibodies to recombinant anti-NGF monoclonal antibodies in dog blood nor were any such neutralising antibodies generated following infusion. By comparison, recombinant human immunoglobulin based proteins are neutralised by antibodies in dog blood at approximately 200 hours post infusion (Richter et al, Drug Metabolism and Disposition 27: 21, 1998). These results therefore show that anti-canine NGF antibodies of the present invention have a long serum half life (9 days) in vivo following intravenous injection and that there are neither pre-existing antibodies nor newly generated antibodies that neutralise the injected anti-NGF antibodies over time.

Example 14—Effect of Anti-Canine NGF Monoclonal Antibodies in Reducing Inflammatory Pain In Vivo Antibody Therapy:
Anti-canine NGF monoclonal antibodies derived from expression vectors expressing SEQ ID NO:10 and SEQ ID NO:11 (canine HCA type heavy chain) were expressed in CHO cells and purified by a combination of ion exchange chromatography, hydrophobic interaction chromatography and size exclusion chromatography (Method I) and buffer exchanged into phosphate buffered saline.
Canine Model of Inflammation:
All experiments were carried out with prior approval of the Institutional Ethics Committee (CRL, Ireland). Beagle dogs were injected (=day −1) with kaolin into the footpad of one hind leg in order to generate a self-resolving inflammation beginning approximately 24 hours later and which causes the dogs to become temporarily lame. In this model, once the initial inflammation response to kaolin recedes, the dogs become steadily less lame over the period of approximately 1-2 weeks and then make a full recovery.

Groups of 3 dogs were injected intravenously with either anti-canine NGF monoclonal antibodies at 200 μg/kg body weight or phosphate buffered saline as vehicle control (=day 0). The dogs were assessed for lameness over 7 days by a visual scoring method (score 0, no lameness (full weight bearing); score 1, slight lameness (not full weight bearing but walking well); score 2, moderate lameness (slightly weight bearing and not walking well), score 3, severe lameness (not weight bearing)). Observers were blinded to which dogs received which injection.

Figure 19:
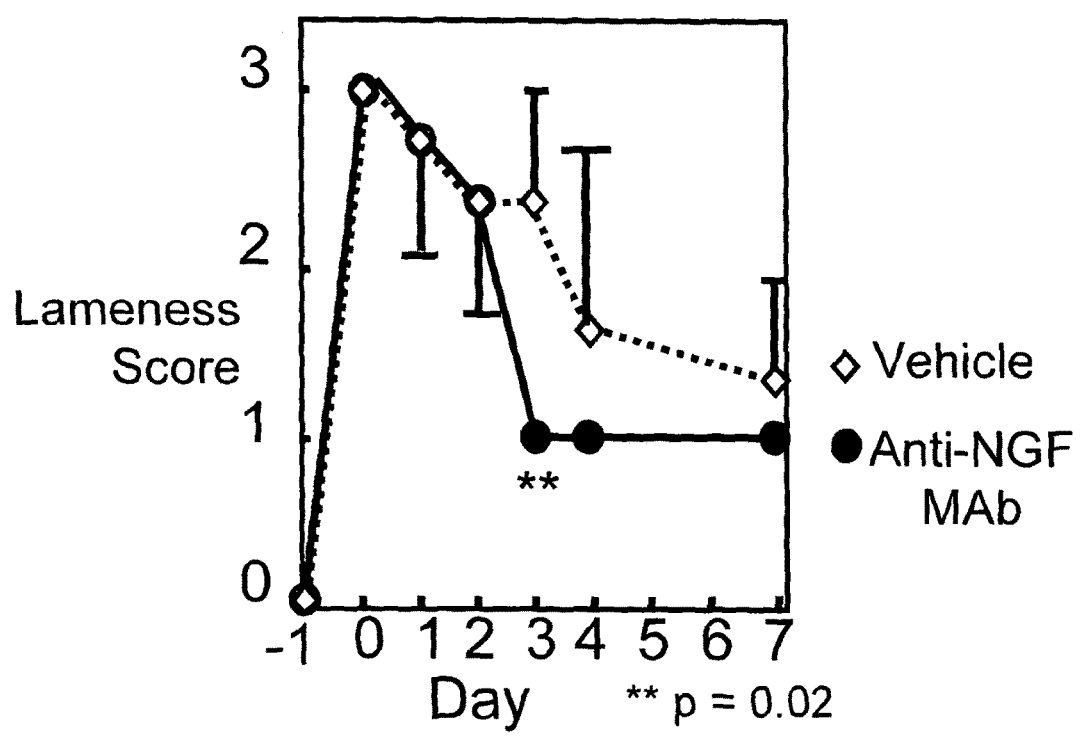
FIG. 19 shows that anti-canine NGF monoclonal antibodies reduce inflammatory pain in dogs. Kaolin was injected into the footpad of beagle dogs at Day −1, antibody or vehicle control at Day 0 and lameness was measured by a visual scoring scale.

The results are shown in FIG. 19. Lameness scores were reduced in the dogs receiving anti-NGF monoclonal antibodies by day 3 post-injection compared with vehicle control, indicating that the anti-NGF monoclonal antibodies had an effect in reducing the pain in the dogs over that seen with vehicle alone. The delayed activity is consistent with the plasma pharmacokinetics of anti-canine NGF monoclonal antibodies which demonstrated a slow tissue distribution (alpha) phase of approximately 30 hours and the relatively poor vascularisation of the footpad area. The results shown in FIG. 19 show that the anti-canine NGF antibodies of the present invention reduce inflammatory pain in dogs with a consequent reduction in lameness.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:
1. A caninized antibody or caninized antigen binding fragment thereof, wherein the light chain variable region comprises the amino acid sequence of SEQ ID NO: 1 and the heavy chain variable region comprises the amino acid sequence of SEQ ID NO: 2.

* * * * *

```
                        SEQUENCE LISTING

<160> NUMBER OF SEQ ID NOS: 33

<210> SEQ ID NO 1
<211> LENGTH: 107
<212> TYPE: PRT
<213> ORGANISM: Artificial Sequence
<220> FEATURE:
<223> OTHER INFORMATION: Variable light chain mark 1 (VL1)

<400> SEQUENCE: 1

Asp Ile Gln Met Thr Gln Ser Pro Ala Ser Leu Ser Leu Ser Gln Glu
1               5                   10                  15

Glu Lys Val Thr Ile Thr Cys Arg Ala Ser Glu Asp Ile Tyr Asn Ala
            20                  25                  30

Leu Ala Trp Tyr Gln Gln Lys Pro Gly Gln Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Glu Tyr Ser Leu Thr Ile Asn Ser Leu Glu Ser
65                  70                  75                  80

Glu Asp Val Ala Val Tyr Phe Cys Gln His Tyr Phe His Tyr Pro Arg
                85                  90                  95

Thr Phe Gly Ala Gly Thr Lys Val Glu Leu Lys
            100                 105

<210> SEQ ID NO 2
<211> LENGTH: 122
<212> TYPE: PRT
<213> ORGANISM: Artificial Sequence
<220> FEATURE:
<223> OTHER INFORMATION: Variable heavy chain mark 1 (VH1)

<400> SEQUENCE: 2

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80
```

```
Lys Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser
        115                 120

<210> SEQ ID NO 3
<211> LENGTH: 107
<212> TYPE: PRT
<213> ORGANISM: Artificial Sequence
<220> FEATURE:
<223> OTHER INFORMATION: Variable light chain mark 2 (VL2)

<400> SEQUENCE: 3

Asp Ile Val Met Thr Gln Ser Pro Ala Ser Leu Ser Leu Ser Gln Glu
1               5                   10                  15

Glu Lys Val Thr Ile Thr Cys Arg Ala Ser Glu Asp Ile Tyr Asn Ala
            20                  25                  30

Leu Ala Trp Tyr Gln Gln Lys Pro Gly Gln Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Glu Phe Ser Leu Thr Ile Ser Ser Leu Glu Pro
65                  70                  75                  80

Glu Asp Val Ala Val Tyr Tyr Cys Gln His Tyr Phe His Tyr Pro Arg
                85                  90                  95

Thr Phe Gly Ala Gly Thr Lys Val Glu Leu Lys
            100                 105

<210> SEQ ID NO 4
<211> LENGTH: 122
<212> TYPE: PRT
<213> ORGANISM: Artificial Sequence
<220> FEATURE:
<223> OTHER INFORMATION: variable heavy chain mark 2 (VH2)

<400> SEQUENCE: 4

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser
        115                 120

<210> SEQ ID NO 5
<211> LENGTH: 217
<212> TYPE: PRT
<213> ORGANISM: Artificial Sequence
```

```
<220> FEATURE:
<223> OTHER INFORMATION: full light chain - VL1 and Kappa light chain
      constant domain

<400> SEQUENCE: 5

Asp Ile Gln Met Thr Gln Ser Pro Ala Ser Leu Ser Leu Ser Gln Glu
1               5                   10                  15

Glu Lys Val Thr Ile Thr Cys Arg Ala Ser Glu Asp Ile Tyr Asn Ala
            20                  25                  30

Leu Ala Trp Tyr Gln Gln Lys Pro Gly Gln Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Glu Tyr Ser Leu Thr Ile Asn Ser Leu Glu Ser
65                  70                  75                  80

Glu Asp Val Ala Val Tyr Phe Cys Gln His Tyr Phe His Tyr Pro Arg
                85                  90                  95

Thr Phe Gly Ala Gly Thr Lys Val Glu Leu Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215

<210> SEQ ID NO 6
<211> LENGTH: 453
<212> TYPE: PRT
<213> ORGANISM: Artificial Sequence
<220> FEATURE:
<223> OTHER INFORMATION: full heavy chain - VH1 and HCA

<400> SEQUENCE: 6

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110
```

```
Gly Gln Gly Thr Leu Val Thr Val Ser Ser Ala Ser Thr Ala Pro
            115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu His Ser Leu Ser Ser Met Val Thr
            180                 185                 190

Val Pro Ser Ser Arg Trp Pro Ser Glu Thr Phe Thr Cys Asn Val Val
    195                 200                 205

His Pro Ala Ser Asn Thr Lys Val Asp Lys Pro Val Phe Asn Glu Cys
210                 215                 220

Arg Cys Thr Asp Thr Pro Pro Cys Pro Val Pro Glu Pro Leu Gly Gly
225                 230                 235                 240

Pro Ser Val Leu Ile Phe Pro Pro Lys Pro Lys Asp Ile Leu Arg Ile
                245                 250                 255

Thr Arg Thr Pro Glu Val Thr Cys Val Val Leu Asp Leu Gly Arg Glu
            260                 265                 270

Asp Pro Glu Val Gln Ile Ser Trp Phe Val Asp Gly Lys Glu Val His
    275                 280                 285

Thr Ala Lys Thr Gln Ser Arg Glu Gln Gln Phe Asn Gly Thr Tyr Arg
290                 295                 300

Val Val Ser Val Leu Pro Ile Glu His Gln Asp Trp Leu Thr Gly Lys
305                 310                 315                 320

Glu Phe Lys Cys Arg Val Asn His Ile Asp Leu Pro Ser Pro Ile Glu
                325                 330                 335

Arg Thr Ile Ser Lys Ala Arg Gly Arg Ala His Lys Pro Ser Val Tyr
            340                 345                 350

Val Leu Pro Pro Ser Pro Lys Glu Leu Ser Ser Ser Asp Thr Val Ser
    355                 360                 365

Ile Thr Cys Leu Ile Lys Asp Phe Tyr Pro Pro Asp Ile Asp Val Glu
370                 375                 380

Trp Gln Ser Asn Gly Gln Gln Glu Pro Glu Arg Lys His Arg Met Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Pro Phe Thr Cys Ala
            420                 425                 430

Val Met His Glu Thr Leu Gln Asn His Tyr Thr Asp Leu Ser Leu Ser
    435                 440                 445

His Ser Pro Gly Lys
    450

<210> SEQ ID NO 7
<211> LENGTH: 457
<212> TYPE: PRT
<213> ORGANISM: Artificial Sequence
<220> FEATURE:
<223> OTHER INFORMATION: full heavy chain - VH1 and HCB

<400> SEQUENCE: 7

Glu Val Gln Leu Val Glu Ser Gly Gly Asp Leu Val Asn Pro Gly Gly
1               5                   10                  15
```

-continued

```
Thr Leu Thr Leu Ser Cys Val Val Ser Gly Phe Ser Leu Thr Asn Asn
             20                  25                  30
Asn Val Asn Trp Val Arg Gln Ala Leu Gly Arg Gly Leu Glu Trp Val
         35                  40                  45
Gly Gly Val Trp Ala Gly Gly Ala Thr Asp Tyr Asn Ser Ala Leu Lys
     50                  55                  60
Ser Arg Leu Thr Ile Thr Arg Asp Thr Ser Lys Ser Thr Val Phe Leu
65                  70                  75                  80
Lys Met His Ser Leu Gln Ser Glu Asp Thr Ala Thr Tyr Tyr Cys Ala
                 85                  90                  95
Arg Asp Gly Gly Tyr Ser Ser Thr Leu Tyr Ala Met Asp Ala Trp
            100                 105                 110
Gly Gln Gly Thr Leu Val Thr Val Ser Ser Ala Ser Thr Ala Pro
        115                 120                 125
Ser Val Phe Pro Leu Ala Pro Ser Cys Gly Ser Thr Ser Gly Ser Thr
    130                 135                 140
Val Ala Leu Ala Cys Leu Val Ser Gly Tyr Phe Pro Glu Pro Val Thr
145                 150                 155                 160
Val Ser Trp Asn Ser Gly Ser Leu Thr Ser Gly Val His Thr Phe Pro
                165                 170                 175
Ser Val Leu Gln Ser Ser Gly Leu Tyr Ser Leu Ser Ser Met Val Thr
            180                 185                 190
Val Pro Ser Ser Arg Trp Pro Ser Glu Thr Phe Thr Cys Asn Val Ala
        195                 200                 205
His Pro Ala Ser Lys Thr Lys Val Asp Lys Pro Val Pro Lys Arg Glu
    210                 215                 220
Asn Gly Arg Val Pro Arg Pro Asp Cys Pro Lys Cys Pro Ala Pro
225                 230                 235                 240
Glu Met Leu Gly Gly Pro Ser Val Phe Ile Phe Pro Pro Lys Pro Lys
                245                 250                 255
Asp Thr Leu Leu Ile Ala Arg Thr Pro Glu Val Thr Cys Val Val Val
            260                 265                 270
Asp Leu Asp Pro Glu Asp Pro Glu Val Gln Ile Ser Trp Phe Val Asp
        275                 280                 285
Gly Lys Gln Met Gln Thr Ala Lys Thr Gln Pro Arg Glu Glu Gln Phe
    290                 295                 300
Asn Gly Thr Tyr Arg Val Val Ser Val Leu Pro Ile Gly His Gln Asp
305                 310                 315                 320
Trp Leu Lys Gly Lys Gln Phe Thr Cys Lys Val Asn Asn Lys Ala Leu
                325                 330                 335
Pro Ser Pro Ile Glu Arg Thr Ile Ser Lys Ala Arg Gly Gln Ala His
            340                 345                 350
Gln Pro Ser Val Tyr Val Leu Pro Pro Ser Arg Glu Glu Leu Ser Lys
        355                 360                 365
Asn Thr Val Ser Leu Thr Cys Leu Ile Lys Asp Phe Tyr Pro Pro Asp
    370                 375                 380
Ile Asp Val Glu Trp Gln Ser Asn Gly Gln Gln Glu Pro Glu Ser Lys
385                 390                 395                 400
Tyr Arg Thr Thr Pro Pro Gln Leu Asp Glu Asp Gly Ser Tyr Phe Leu
                405                 410                 415
Tyr Ser Lys Leu Ser Val Asp Lys Ser Arg Trp Gln Arg Gly Asp Thr
            420                 425                 430
Phe Ile Cys Ala Val Met His Glu Ala Leu His Asn His Tyr Thr Gln
```

```
                435                 440                 445
Glu Ser Leu Ser His Ser Pro Gly Lys
    450                 455
```

<210> SEQ ID NO 8
<211> LENGTH: 455
<212> TYPE: PRT
<213> ORGANISM: Artificial Sequence
<220> FEATURE:
<223> OTHER INFORMATION: full heavy chain - VH1 and HCC

<400> SEQUENCE: 8

```
Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Gln Ser Gly Ser Thr
    130                 135                 140

Val Ala Leu Ala Cys Leu Val Ser Gly Tyr Ile Pro Glu Pro Val Thr
145                 150                 155                 160

Val Ser Trp Asn Ser Val Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Thr Asn Thr Lys Val Asp Lys Pro Val Ala Lys Glu Cys
    210                 215                 220

Glu Cys Lys Cys Asn Cys Asn Asn Cys Pro Cys Pro Gly Cys Gly Leu
225                 230                 235                 240

Leu Gly Gly Pro Ser Val Phe Ile Phe Pro Pro Lys Pro Lys Asp Ile
                245                 250                 255

Leu Val Thr Ala Arg Thr Pro Thr Val Thr Cys Val Val Val Asp Leu
            260                 265                 270

Asp Pro Glu Asn Pro Glu Val Gln Ile Ser Trp Phe Val Asp Ser Lys
        275                 280                 285

Gln Val Gln Thr Ala Asn Thr Gln Pro Arg Glu Glu Gln Ser Asn Gly
    290                 295                 300

Thr Tyr Arg Val Val Ser Val Leu Pro Ile Gly His Gln Asp Trp Leu
305                 310                 315                 320

Ser Gly Lys Gln Phe Lys Cys Lys Val Asn Asn Lys Ala Leu Pro Ser
                325                 330                 335

Pro Ile Glu Glu Ile Ile Ser Lys Thr Pro Gly Gln Ala His Gln Pro
```

```
                    340                 345                 350
Asn Val Tyr Val Leu Pro Pro Ser Arg Asp Glu Met Ser Lys Asn Thr
            355                 360                 365

Val Thr Leu Thr Cys Leu Val Lys Asp Phe Phe Pro Glu Ile Asp
    370                 375                 380

Val Glu Trp Gln Ser Asn Gly Gln Gln Glu Pro Glu Ser Lys Tyr Arg
385                 390                 395                 400

Met Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Ile Ser
            435                 440                 445

Leu Ser His Ser Pro Gly Lys
    450                 455

<210> SEQ ID NO 9
<211> LENGTH: 453
<212> TYPE: PRT
<213> ORGANISM: Artificial Sequence
<220> FEATURE:
<223> OTHER INFORMATION: full heavy chain - VH1 and HCD

<400> SEQUENCE: 9

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Thr Val Thr
            180                 185                 190

Val Pro Ser Ser Arg Trp Pro Ser Glu Thr Phe Thr Cys Asn Val Val
        195                 200                 205

His Pro Ala Ser Asn Thr Lys Val Asp Lys Pro Val Pro Lys Glu Ser
    210                 215                 220

Thr Cys Lys Cys Ile Ser Pro Cys Pro Val Pro Glu Ser Leu Gly Gly
225                 230                 235                 240

Pro Ser Val Phe Ile Phe Pro Pro Lys Pro Lys Asp Ile Leu Arg Ile
```

```
                245                 250                 255
Thr Arg Thr Pro Glu Ile Thr Cys Val Val Leu Asp Leu Gly Arg Glu
            260                 265                 270

Asp Pro Glu Val Gln Ile Ser Trp Phe Val Asp Gly Lys Glu Val His
        275                 280                 285

Thr Ala Lys Thr Gln Pro Arg Glu Gln Gln Phe Asn Ser Thr Tyr Arg
    290                 295                 300

Val Val Ser Val Leu Pro Ile Glu His Gln Asp Trp Leu Thr Gly Lys
305                 310                 315                 320

Glu Phe Lys Cys Arg Val Asn His Ile Gly Leu Pro Ser Pro Ile Glu
            325                 330                 335

Arg Thr Ile Ser Lys Ala Arg Gly Gln Ala His Gln Pro Ser Val Tyr
        340                 345                 350

Val Leu Pro Pro Ser Pro Lys Glu Leu Ser Ser Ser Asp Thr Val Thr
    355                 360                 365

Leu Thr Cys Leu Ile Lys Asp Phe Tyr Pro Pro Glu Ile Asp Val Glu
370                 375                 380

Trp Gln Ser Asn Gly Gln Pro Glu Pro Glu Ser Lys Tyr His Thr Thr
385                 390                 395                 400

Ala Pro Gln Leu Asp Glu Asp Gly Ser Tyr Phe Leu Tyr Ser Lys Leu
            405                 410                 415

Ser Val Asp Lys Ser Arg Trp Gln Gln Gly Asp Thr Phe Thr Cys Ala
        420                 425                 430

Val Met His Glu Ala Leu Gln Asn His Tyr Thr Asp Leu Ser Leu Ser
    435                 440                 445

His Ser Pro Gly Lys
    450

<210> SEQ ID NO 10
<211> LENGTH: 217
<212> TYPE: PRT
<213> ORGANISM: Artificial Sequence
<220> FEATURE:
<223> OTHER INFORMATION: VL2 and kappa light chain constant domain

<400> SEQUENCE: 10

Asp Ile Val Met Thr Gln Ser Pro Ala Ser Leu Ser Leu Ser Gln Glu
1               5                   10                  15

Glu Lys Val Thr Ile Thr Cys Arg Ala Ser Glu Asp Ile Tyr Asn Ala
            20                  25                  30

Leu Ala Trp Tyr Gln Gln Lys Pro Gly Gln Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Glu Phe Ser Leu Thr Ile Ser Ser Leu Glu Pro
65                  70                  75                  80

Glu Asp Val Ala Val Tyr Tyr Cys Gln His Tyr Phe His Tyr Pro Arg
            85                  90                  95

Thr Phe Gly Ala Gly Thr Lys Val Glu Leu Lys Arg Asn Asp Ala Gln
        100                 105                 110

Pro Ala Val Tyr Leu Phe Gln Pro Ser Pro Asp Gln Leu His Thr Gly
    115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
```

```
                145                 150                 155                 160
Glu Ser Val Thr Glu Gln Asp Lys Asp Ser Thr Tyr Ser Leu Ser Ser
                    165                 170                 175

Thr Leu Thr Met Ser Ser Thr Glu Tyr Leu Ser His Glu Leu Tyr Ser
                180                 185                 190

Cys Glu Ile Thr His Lys Ser Leu Pro Ser Thr Leu Ile Lys Ser Phe
            195                 200                 205

Gln Arg Ser Glu Cys Gln Arg Val Asp
        210                 215

<210> SEQ ID NO 11
<211> LENGTH: 453
<212> TYPE: PRT
<213> ORGANISM: Artificial Sequence
<220> FEATURE:
<223> OTHER INFORMATION: full heavy chain - VH2 and HCA

<400> SEQUENCE: 11

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu His Ser Leu Ser Ser Met Val Thr
            180                 185                 190

Val Pro Ser Ser Arg Trp Pro Ser Glu Thr Phe Thr Cys Asn Val Val
        195                 200                 205

His Pro Ala Ser Asn Thr Lys Val Asp Lys Pro Val Phe Asn Glu Cys
    210                 215                 220

Arg Cys Thr Asp Thr Pro Pro Cys Pro Val Pro Glu Pro Leu Gly Gly
225                 230                 235                 240

Pro Ser Val Leu Ile Phe Pro Pro Lys Pro Lys Asp Ile Leu Arg Ile
                245                 250                 255

Thr Arg Thr Pro Glu Val Thr Cys Val Val Leu Asp Leu Gly Arg Glu
            260                 265                 270

Asp Pro Glu Val Gln Ile Ser Trp Phe Val Asp Gly Lys Glu Val His
        275                 280                 285

Thr Ala Lys Thr Gln Ser Arg Glu Gln Gln Phe Asn Gly Thr Tyr Arg
```

```
              290                 295                 300
Val Val Ser Val Leu Pro Ile Glu His Gln Asp Trp Leu Thr Gly Lys
305                 310                 315                 320

Glu Phe Lys Cys Arg Val Asn His Ile Asp Leu Pro Ser Pro Ile Glu
                325                 330                 335

Arg Thr Ile Ser Lys Ala Arg Gly Arg Ala His Lys Pro Ser Val Tyr
            340                 345                 350

Val Leu Pro Pro Ser Pro Lys Glu Leu Ser Ser Ser Asp Thr Val Ser
        355                 360                 365

Ile Thr Cys Leu Ile Lys Asp Phe Tyr Pro Pro Asp Ile Asp Val Glu
    370                 375                 380

Trp Gln Ser Asn Gly Gln Gln Glu Pro Glu Arg Lys His Arg Met Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Pro Phe Thr Cys Ala
            420                 425                 430

Val Met His Glu Thr Leu Gln Asn His Tyr Thr Asp Leu Ser Leu Ser
        435                 440                 445

His Ser Pro Gly Lys
    450

<210> SEQ ID NO 12
<211> LENGTH: 457
<212> TYPE: PRT
<213> ORGANISM: Artificial Sequence
<220> FEATURE:
<223> OTHER INFORMATION: full heavy chain - VH2 and HCB

<400> SEQUENCE: 12

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
```

```
            195                 200                 205
His Pro Ala Ser Lys Thr Lys Val Asp Lys Pro Val Pro Lys Arg Glu
    210                 215                 220

Asn Gly Arg Val Pro Arg Pro Asp Cys Pro Lys Cys Pro Ala Pro
225                 230                 235                 240

Glu Met Leu Gly Gly Pro Ser Val Phe Ile Phe Pro Pro Lys Pro Lys
                    245                 250                 255

Asp Thr Leu Leu Ile Ala Arg Thr Pro Glu Val Thr Cys Val Val Val
                260                 265                 270

Asp Leu Asp Pro Glu Asp Pro Glu Val Gln Ile Ser Trp Phe Val Asp
            275                 280                 285

Gly Lys Gln Met Gln Thr Ala Lys Thr Gln Pro Arg Glu Glu Gln Phe
        290                 295                 300

Asn Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
                340                 345                 350

Gln Pro Ser Val Tyr Val Leu Pro Pro Ser Arg Glu Glu Leu Ser Lys
            355                 360                 365

Asn Thr Val Ser Leu Thr Cys Leu Ile Lys Asp Phe Tyr Pro Pro Asp
        370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
                420                 425                 430

Phe Ile Cys Ala Val Met His Glu Ala Leu His Asn His Tyr Thr Gln
            435                 440                 445

Glu Ser Leu Ser His Ser Pro Gly Lys
        450                 455

<210> SEQ ID NO 13
<211> LENGTH: 455
<212> TYPE: PRT
<213> ORGANISM: Artificial Sequence
<220> FEATURE:
<223> OTHER INFORMATION: full heavy chain - VH2 and HCC

<400> SEQUENCE: 13

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
                20                  25                  30

Asn Val Asn Trp Val Arg Gln Ala Leu Gly Arg Gly Leu Glu Trp Val
            35                  40                  45

Gly Gly Val Trp Ala Gly Gly Ala Thr Asp Tyr Asn Ser Ala Leu Lys
        50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
```

```
            100                 105                 110
Gly Gln Gly Thr Leu Val Thr Val Ser Ser Ala Ser Thr Ala Pro
            115                 120                 125
Ser Val Phe Pro Leu Ala Pro Ser Cys Gly Ser Gln Ser Gly Ser Thr
    130                 135                 140
Val Ala Leu Ala Cys Leu Val Ser Gly Tyr Ile Pro Glu Pro Val Thr
145                 150                 155                 160
Val Ser Trp Asn Ser Val Ser Leu Thr Ser Gly Val His Thr Phe Pro
                165                 170                 175
Ser Val Leu Gln Ser Ser Gly Leu Tyr Ser Leu Ser Ser Met Val Thr
            180                 185                 190
Val Pro Ser Ser Arg Trp Pro Ser Glu Thr Phe Thr Cys Asn Val Ala
        195                 200                 205
His Pro Ala Thr Asn Thr Lys Val Asp Lys Pro Val Ala Lys Glu Cys
    210                 215                 220
Glu Cys Lys Cys Asn Cys Asn Asn Cys Pro Cys Pro Gly Cys Gly Leu
225                 230                 235                 240
Leu Gly Gly Pro Ser Val Phe Ile Phe Pro Pro Lys Pro Lys Asp Ile
                245                 250                 255
Leu Val Thr Ala Arg Thr Pro Thr Val Thr Cys Val Val Asp Leu
            260                 265                 270
Asp Pro Glu Asn Pro Glu Val Gln Ile Ser Trp Phe Val Asp Ser Lys
        275                 280                 285
Gln Val Gln Thr Ala Asn Thr Gln Pro Arg Glu Glu Gln Ser Asn Gly
    290                 295                 300
Thr Tyr Arg Val Val Ser Val Leu Pro Ile Gly His Gln Asp Trp Leu
305                 310                 315                 320
Ser Gly Lys Gln Phe Lys Cys Lys Val Asn Asn Lys Ala Leu Pro Ser
                325                 330                 335
Pro Ile Glu Glu Ile Ile Ser Lys Thr Pro Gly Gln Ala His Gln Pro
            340                 345                 350
Asn Val Tyr Val Leu Pro Pro Ser Arg Asp Glu Met Ser Lys Asn Thr
        355                 360                 365
Val Thr Leu Thr Cys Leu Val Lys Asp Phe Phe Pro Pro Glu Ile Asp
    370                 375                 380
Val Glu Trp Gln Ser Asn Gly Gln Gln Glu Pro Glu Ser Lys Tyr Arg
385                 390                 395                 400
Met Thr Pro Pro Gln Leu Asp Glu Asp Gly Ser Tyr Phe Leu Tyr Ser
                405                 410                 415
Lys Leu Ser Val Asp Lys Ser Arg Trp Gln Arg Gly Asp Thr Phe Ile
            420                 425                 430
Cys Ala Val Met His Glu Ala Leu His Asn His Tyr Thr Gln Ile Ser
        435                 440                 445
Leu Ser His Ser Pro Gly Lys
    450                 455

<210> SEQ ID NO 14
<211> LENGTH: 453
<212> TYPE: PRT
<213> ORGANISM: Artificial Sequence
<220> FEATURE:
<223> OTHER INFORMATION: full heavy chain - VH2 and HCD

<400> SEQUENCE: 14

Glu Val Gln Leu Val Glu Ser Gly Gly Asp Leu Val Asn Pro Gly Gly
```

-continued

```
1               5                   10                  15
Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
            35                  40                  45

Gly Val Trp Ala Gly Gly Ala Thr Asp Tyr Asn Ser Ala Leu Lys
50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Thr Leu Tyr Ala Met Asp Ala Trp
                100                 105                 110

Gly Gln Gly Thr Leu Val Thr Val Ser Ser Ala Ser Thr Ala Pro
                115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Thr Val Thr
                180                 185                 190

Val Pro Ser Ser Arg Trp Pro Ser Glu Thr Phe Thr Cys Asn Val Val
                195                 200                 205

His Pro Ala Ser Asn Thr Lys Val Asp Lys Pro Val Pro Lys Glu Ser
    210                 215                 220

Thr Cys Lys Cys Ile Ser Pro Cys Pro Val Pro Glu Ser Leu Gly Gly
225                 230                 235                 240

Pro Ser Val Phe Ile Phe Pro Pro Lys Pro Lys Asp Ile Leu Arg Ile
                245                 250                 255

Thr Arg Thr Pro Glu Ile Thr Cys Val Val Leu Asp Leu Gly Arg Glu
                260                 265                 270

Asp Pro Glu Val Gln Ile Ser Trp Phe Val Asp Gly Lys Glu Val His
                275                 280                 285

Thr Ala Lys Thr Gln Pro Arg Glu Gln Gln Phe Asn Ser Thr Tyr Arg
    290                 295                 300

Val Val Ser Val Leu Pro Ile Glu His Gln Asp Trp Leu Thr Gly Lys
305                 310                 315                 320

Glu Phe Lys Cys Arg Val Asn His Ile Gly Leu Pro Ser Pro Ile Glu
                325                 330                 335

Arg Thr Ile Ser Lys Ala Arg Gly Gln Ala His Gln Pro Ser Val Tyr
                340                 345                 350

Val Leu Pro Pro Ser Pro Lys Glu Leu Ser Ser Ser Asp Thr Val Thr
                355                 360                 365

Leu Thr Cys Leu Ile Lys Asp Phe Tyr Pro Pro Glu Ile Asp Val Glu
    370                 375                 380

Trp Gln Ser Asn Gly Gln Pro Glu Pro Glu Ser Lys Tyr His Thr Thr
385                 390                 395                 400

Ala Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Thr Phe Thr Cys Ala
                420                 425                 430
```

Val Met His Glu Ala Leu Gln Asn His Tyr Thr Asp Leu Ser Leu Ser
            435                 440                 445

His Ser Pro Gly Lys
        450

<210> SEQ ID NO 15
<211> LENGTH: 453
<212> TYPE: PRT
<213> ORGANISM: Artificial Sequence
<220> FEATURE:
<223> OTHER INFORMATION: VH1 and aglycosylated HCA

<400> SEQUENCE: 15

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu His Ser Leu Ser Ser Met Val Thr
            180                 185                 190

Val Pro Ser Ser Arg Trp Pro Ser Glu Thr Phe Thr Cys Asn Val Val
        195                 200                 205

His Pro Ala Ser Asn Thr Lys Val Asp Lys Pro Val Phe Asn Glu Cys
    210                 215                 220

Arg Cys Thr Asp Thr Pro Pro Cys Pro Val Pro Glu Pro Leu Gly Gly
225                 230                 235                 240

Pro Ser Val Leu Ile Phe Pro Pro Lys Pro Lys Asp Ile Leu Arg Ile
                245                 250                 255

Thr Arg Thr Pro Glu Val Thr Cys Val Val Leu Asp Leu Gly Arg Glu
            260                 265                 270

Asp Pro Glu Val Gln Ile Ser Trp Phe Val Asp Gly Lys Glu Val His
        275                 280                 285

Thr Ala Lys Thr Gln Ser Arg Glu Gln Gln Phe Ala Gly Thr Tyr Arg
    290                 295                 300

Val Val Ser Val Leu Pro Ile Glu His Gln Asp Trp Leu Thr Gly Lys
305                 310                 315                 320

Glu Phe Lys Cys Arg Val Asn His Ile Asp Leu Pro Ser Pro Ile Glu
                325                 330                 335

```
Arg Thr Ile Ser Lys Ala Arg Gly Arg Ala His Lys Pro Ser Val Tyr
            340                 345                 350

Val Leu Pro Pro Ser Pro Lys Glu Leu Ser Ser Ser Asp Thr Val Ser
            355                 360                 365

Ile Thr Cys Leu Ile Lys Asp Phe Tyr Pro Pro Asp Ile Asp Val Glu
370                 375                 380

Trp Gln Ser Asn Gly Gln Gln Glu Pro Glu Arg Lys His Arg Met Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Pro Phe Thr Cys Ala
            420                 425                 430

Val Met His Glu Thr Leu Gln Asn His Tyr Thr Asp Leu Ser Leu Ser
            435                 440                 445

His Ser Pro Gly Lys
    450

<210> SEQ ID NO 16
<211> LENGTH: 457
<212> TYPE: PRT
<213> ORGANISM: Artificial Sequence
<220> FEATURE:
<223> OTHER INFORMATION: VH1 and aglycosylated HCB

<400> SEQUENCE: 16

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
            35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Pro Asp Cys Pro Lys Cys Pro Ala Pro
225                 230                 235                 240
```

-continued

Glu Met Leu Gly Gly Pro Ser Val Phe Ile Phe Pro Pro Lys Pro Lys
            245                 250                 255

Asp Thr Leu Leu Ile Ala Arg Thr Pro Glu Val Thr Cys Val Val Val
        260                 265                 270

Asp Leu Asp Pro Glu Asp Pro Glu Val Gln Ile Ser Trp Phe Val Asp
    275                 280                 285

Gly Lys Gln Met Gln Thr Ala Lys Thr Gln Pro Arg Glu Glu Gln Phe
290                 295                 300

Ala Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
        355                 360                 365

Asn Thr Val Ser Leu Thr Cys Leu Ile Lys Asp Phe Tyr Pro Pro Asp
    370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
        435                 440                 445

Glu Ser Leu Ser His Ser Pro Gly Lys
    450                 455

<210> SEQ ID NO 17
<211> LENGTH: 455
<212> TYPE: PRT
<213> ORGANISM: Artificial Sequence
<220> FEATURE:
<223> OTHER INFORMATION: VH1 and aglycosylated HCC

<400> SEQUENCE: 17

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Gln Ser Gly Ser Thr
    130                 135                 140

```
Val Ala Leu Ala Cys Leu Val Ser Gly Tyr Ile Pro Glu Pro Val Thr
145                 150                 155                 160

Val Ser Trp Asn Ser Val Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Thr Asn Thr Lys Val Asp Lys Pro Val Ala Lys Glu Cys
    210                 215                 220

Glu Cys Lys Cys Asn Cys Asn Asn Cys Pro Cys Pro Gly Cys Gly Leu
225                 230                 235                 240

Leu Gly Gly Pro Ser Val Phe Ile Phe Pro Pro Lys Pro Lys Asp Ile
                245                 250                 255

Leu Val Thr Ala Arg Thr Pro Thr Val Thr Cys Val Val Val Asp Leu
            260                 265                 270

Asp Pro Glu Asn Pro Glu Val Gln Ile Ser Trp Phe Val Asp Ser Lys
        275                 280                 285

Gln Val Gln Thr Ala Asn Thr Gln Pro Arg Glu Glu Gln Ser Ala Gly
    290                 295                 300

Thr Tyr Arg Val Val Ser Val Leu Pro Ile Gly His Gln Asp Trp Leu
305                 310                 315                 320

Ser Gly Lys Gln Phe Lys Cys Lys Val Asn Asn Lys Ala Leu Pro Ser
                325                 330                 335

Pro Ile Glu Glu Ile Ile Ser Lys Thr Pro Gly Gln Ala His Gln Pro
            340                 345                 350

Asn Val Tyr Val Leu Pro Pro Ser Arg Asp Glu Met Ser Lys Asn Thr
        355                 360                 365

Val Thr Leu Thr Cys Leu Val Lys Asp Phe Phe Pro Pro Glu Ile Asp
    370                 375                 380

Val Glu Trp Gln Ser Asn Gly Gln Gln Glu Pro Glu Ser Lys Tyr Arg
385                 390                 395                 400

Met Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Ile Ser
        435                 440                 445

Leu Ser His Ser Pro Gly Lys
    450                 455

<210> SEQ ID NO 18
<211> LENGTH: 453
<212> TYPE: PRT
<213> ORGANISM: Artificial Sequence
<220> FEATURE:
<223> OTHER INFORMATION: VH1 and aglycosylated HCD

<400> SEQUENCE: 18

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45
```

Gly Gly Val Trp Ala Gly Ala Thr Asp Tyr Asn Ser Ala Leu Lys
 50                  55                  60

Ser Arg Leu Thr Ile Thr Arg Asp Thr Ser Lys Ser Thr Val Phe Leu
 65                  70                  75                  80

Lys Met His Ser Leu Gln Ser Glu Asp Thr Ala Thr Tyr Tyr Cys Ala
                 85                  90                  95

Arg Asp Gly Gly Tyr Ser Ser Ser Thr Leu Tyr Ala Met Asp Ala Trp
             100                 105                 110

Gly Gln Gly Thr Leu Val Thr Val Ser Ser Ala Ser Thr Thr Ala Pro
         115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Thr Val Thr
            180                 185                 190

Val Pro Ser Ser Arg Trp Pro Ser Glu Thr Phe Thr Cys Asn Val Val
        195                 200                 205

His Pro Ala Ser Asn Thr Lys Val Asp Lys Pro Val Pro Lys Glu Ser
    210                 215                 220

Thr Cys Lys Cys Ile Ser Pro Cys Pro Val Pro Glu Ser Leu Gly Gly
225                 230                 235                 240

Pro Ser Val Phe Ile Phe Pro Pro Lys Pro Lys Asp Ile Leu Arg Ile
                245                 250                 255

Thr Arg Thr Pro Glu Ile Thr Cys Val Val Leu Asp Leu Gly Arg Glu
            260                 265                 270

Asp Pro Glu Val Gln Ile Ser Trp Phe Val Asp Gly Lys Glu Val His
        275                 280                 285

Thr Ala Lys Thr Gln Pro Arg Glu Gln Gln Phe Ala Ser Thr Tyr Arg
290                 295                 300

Val Val Ser Val Leu Pro Ile Glu His Gln Asp Trp Leu Thr Gly Lys
305                 310                 315                 320

Glu Phe Lys Cys Arg Val Asn His Ile Gly Leu Pro Ser Pro Ile Glu
                325                 330                 335

Arg Thr Ile Ser Lys Ala Arg Gly Gln Ala His Gln Pro Ser Val Tyr
            340                 345                 350

Val Leu Pro Pro Ser Pro Lys Glu Leu Ser Ser Ser Asp Thr Val Thr
        355                 360                 365

Leu Thr Cys Leu Ile Lys Asp Phe Tyr Pro Pro Glu Ile Asp Val Glu
    370                 375                 380

Trp Gln Ser Asn Gly Gln Pro Glu Pro Glu Ser Lys Tyr His Thr Thr
385                 390                 395                 400

Ala Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Thr Phe Thr Cys Ala
            420                 425                 430

Val Met His Glu Ala Leu Gln Asn His Tyr Thr Asp Leu Ser Leu Ser
        435                 440                 445

His Ser Pro Gly Lys
    450

<210> SEQ ID NO 19
<211> LENGTH: 453
<212> TYPE: PRT
<213> ORGANISM: Artificial Sequence
<220> FEATURE:
<223> OTHER INFORMATION: VH2 and aglycosylated HCA

<400> SEQUENCE: 19

```
Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu His Ser Leu Ser Ser Met Val Thr
            180                 185                 190

Val Pro Ser Ser Arg Trp Pro Ser Glu Thr Phe Thr Cys Asn Val Val
        195                 200                 205

His Pro Ala Ser Asn Thr Lys Val Asp Lys Pro Val Phe Asn Glu Cys
    210                 215                 220

Arg Cys Thr Asp Thr Pro Pro Cys Pro Val Pro Glu Pro Leu Gly Gly
225                 230                 235                 240

Pro Ser Val Leu Ile Phe Pro Pro Lys Pro Lys Asp Ile Leu Arg Ile
                245                 250                 255

Thr Arg Thr Pro Glu Val Thr Cys Val Val Leu Asp Leu Gly Arg Glu
            260                 265                 270

Asp Pro Glu Val Gln Ile Ser Trp Phe Val Asp Gly Lys Glu Val His
        275                 280                 285

Thr Ala Lys Thr Gln Ser Arg Glu Gln Gln Phe Ala Gly Thr Tyr Arg
    290                 295                 300

Val Val Ser Val Leu Pro Ile Glu His Gln Asp Trp Leu Thr Gly Lys
305                 310                 315                 320

Glu Phe Lys Cys Arg Val Asn His Ile Asp Leu Pro Ser Pro Ile Glu
                325                 330                 335

Arg Thr Ile Ser Lys Ala Arg Gly Arg Ala His Lys Pro Ser Val Tyr
            340                 345                 350

Val Leu Pro Pro Ser Pro Lys Glu Leu Ser Ser Ser Asp Thr Val Ser
        355                 360                 365
```

-continued

```
Ile Thr Cys Leu Ile Lys Asp Phe Tyr Pro Pro Asp Ile Asp Val Glu
            370                 375                 380

Trp Gln Ser Asn Gly Gln Gln Glu Pro Glu Arg Lys His Arg Met Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Pro Phe Thr Cys Ala
                420                 425                 430

Val Met His Glu Thr Leu Gln Asn His Tyr Thr Asp Leu Ser Leu Ser
                435                 440                 445

His Ser Pro Gly Lys
    450
```

<210> SEQ ID NO 20
<211> LENGTH: 457
<212> TYPE: PRT
<213> ORGANISM: Artificial Sequence
<220> FEATURE:
<223> OTHER INFORMATION: VH2 and aglycosylated HCB

<400> SEQUENCE: 20

```
Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
                20                  25                  30

Asn Val Asn Trp Val Arg Gln Ala Leu Gly Arg Gly Leu Glu Trp Val
                35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
                100                 105                 110

Gly Gln Gly Thr Leu Val Thr Val Ser Ser Ala Ser Thr Thr Ala Pro
                115                 120                 125

Ser Val Phe Pro Leu Ala Pro Ser Cys Gly Ser Thr Ser Gly Ser Thr
                130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
                180                 185                 190

Val Pro Ser Ser Arg Trp Pro Ser Glu Thr Phe Thr Cys Asn Val Ala
                195                 200                 205

His Pro Ala Ser Lys Thr Lys Val Asp Lys Pro Val Pro Lys Arg Glu
                210                 215                 220

Asn Gly Arg Val Pro Arg Pro Asp Cys Pro Lys Cys Pro Ala Pro
225                 230                 235                 240

Glu Met Leu Gly Gly Pro Ser Val Phe Ile Phe Pro Pro Lys Pro Lys
                245                 250                 255

Asp Thr Leu Leu Ile Ala Arg Thr Pro Glu Val Thr Cys Val Val Val
                260                 265                 270
```

```
Asp Leu Asp Pro Glu Asp Pro Glu Val Gln Ile Ser Trp Phe Val Asp
            275                 280                 285

Gly Lys Gln Met Gln Thr Ala Lys Thr Gln Pro Arg Glu Glu Gln Phe
290                 295                 300

Ala Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
        355                 360                 365

Asn Thr Val Ser Leu Thr Cys Leu Ile Lys Asp Phe Tyr Pro Pro Asp
370                 375                 380

Ile Asp Val Glu Trp Gln Ser Asn Gly Gln Gln Glu Pro Glu Ser Lys
385                 390                 395                 400

Tyr Arg Thr Thr Pro Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
        435                 440                 445

Glu Ser Leu Ser His Ser Pro Gly Lys
            450                 455

<210> SEQ ID NO 21
<211> LENGTH: 455
<212> TYPE: PRT
<213> ORGANISM: Artificial Sequence
<220> FEATURE:
<223> OTHER INFORMATION: VH2 and aglycosylated HCC

<400> SEQUENCE: 21

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Gln Met His Ser Leu Arg Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Gln Ser Gly Ser Thr
    130                 135                 140

Val Ala Leu Ala Cys Leu Val Ser Gly Tyr Ile Pro Glu Pro Val Thr
145                 150                 155                 160

Val Ser Trp Asn Ser Val Ser Leu Thr Ser Gly Val His Thr Phe Pro
                165                 170                 175
```

```
Ser Val Leu Gln Ser Ser Gly Leu Tyr Ser Leu Ser Ser Met Val Thr
            180                 185                 190
Val Pro Ser Ser Arg Trp Pro Ser Glu Thr Phe Thr Cys Asn Val Ala
        195                 200                 205
His Pro Ala Thr Asn Thr Lys Val Asp Lys Pro Val Ala Lys Glu Cys
    210                 215                 220
Glu Cys Lys Cys Asn Cys Asn Asn Cys Pro Cys Pro Gly Cys Gly Leu
225                 230                 235                 240
Leu Gly Gly Pro Ser Val Phe Ile Phe Pro Pro Lys Pro Lys Asp Ile
                245                 250                 255
Leu Val Thr Ala Arg Thr Pro Thr Val Thr Cys Val Val Val Asp Leu
            260                 265                 270
Asp Pro Glu Asn Pro Glu Val Gln Ile Ser Trp Phe Val Asp Ser Lys
        275                 280                 285
Gln Val Gln Thr Ala Asn Thr Gln Pro Arg Glu Glu Gln Ser Ala Gly
    290                 295                 300
Thr Tyr Arg Val Val Ser Val Leu Pro Ile Gly His Gln Asp Trp Leu
305                 310                 315                 320
Ser Gly Lys Gln Phe Lys Cys Lys Val Asn Asn Lys Ala Leu Pro Ser
                325                 330                 335
Pro Ile Glu Glu Ile Ile Ser Lys Thr Pro Gly Gln Ala His Gln Pro
            340                 345                 350
Asn Val Tyr Val Leu Pro Pro Ser Arg Asp Glu Met Ser Lys Asn Thr
        355                 360                 365
Val Thr Leu Thr Cys Leu Val Lys Asp Phe Phe Pro Pro Glu Ile Asp
    370                 375                 380
Val Glu Trp Gln Ser Asn Gly Gln Gln Glu Pro Glu Ser Lys Tyr Arg
385                 390                 395                 400
Met Thr Pro Pro Gln Leu Asp Glu Asp Gly Ser Tyr Phe Leu Tyr Ser
                405                 410                 415
Lys Leu Ser Val Asp Lys Ser Arg Trp Gln Arg Gly Asp Thr Phe Ile
            420                 425                 430
Cys Ala Val Met His Glu Ala Leu His Asn His Tyr Thr Gln Ile Ser
        435                 440                 445
Leu Ser His Ser Pro Gly Lys
    450                 455

<210> SEQ ID NO 22
<211> LENGTH: 453
<212> TYPE: PRT
<213> ORGANISM: Artificial Sequence
<220> FEATURE:
<223> OTHER INFORMATION: VH2 and aglycosylated HCD

<400> SEQUENCE: 22

Glu Val Gln Leu Val Glu Ser Gly Gly Asp Leu Val Asn Pro Gly Gly
1               5                   10                  15
Thr Leu Thr Leu Ser Cys Val Val Ser Gly Phe Ser Leu Thr Asn Asn
            20                  25                  30
Asn Val Asn Trp Val Arg Gln Ala Leu Gly Arg Gly Leu Glu Trp Val
        35                  40                  45
Gly Gly Val Trp Ala Gly Gly Ala Thr Asp Tyr Asn Ser Ala Leu Lys
    50                  55                  60
Ser Arg Leu Thr Ile Thr Arg Asp Thr Ser Lys Ser Thr Val Phe Leu
65                  70                  75                  80
```

```
Gln Met His Ser Leu Arg Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
            115                 120                 125

Ser Val Phe Pro Leu Ala Pro Ser Cys Gly Ser Thr Ser Gly Ser Thr
            130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Val Thr
                180                 185                 190

Val Pro Ser Ser Arg Trp Pro Ser Glu Thr Phe Thr Cys Asn Val Val
            195                 200                 205

His Pro Ala Ser Asn Thr Lys Val Asp Lys Pro Val Pro Lys Glu Ser
    210                 215                 220

Thr Cys Lys Cys Ile Ser Pro Cys Pro Val Pro Glu Ser Leu Gly Gly
225                 230                 235                 240

Pro Ser Val Phe Ile Phe Pro Pro Lys Pro Lys Asp Ile Leu Arg Ile
                245                 250                 255

Thr Arg Thr Pro Glu Ile Thr Cys Val Val Leu Asp Leu Gly Arg Glu
            260                 265                 270

Asp Pro Glu Val Gln Ile Ser Trp Phe Val Asp Gly Lys Glu Val His
            275                 280                 285

Thr Ala Lys Thr Gln Pro Arg Glu Gln Gln Phe Ala Ser Thr Tyr Arg
    290                 295                 300

Val Val Ser Val Leu Pro Ile Glu His Gln Asp Trp Leu Thr Gly Lys
305                 310                 315                 320

Glu Phe Lys Cys Arg Val Asn His Ile Gly Leu Pro Ser Pro Ile Glu
                325                 330                 335

Arg Thr Ile Ser Lys Ala Arg Gly Gln Ala His Gln Pro Ser Val Tyr
            340                 345                 350

Val Leu Pro Pro Ser Pro Lys Glu Leu Ser Ser Ser Asp Thr Val Thr
            355                 360                 365

Leu Thr Cys Leu Ile Lys Asp Phe Tyr Pro Pro Glu Ile Asp Val Glu
    370                 375                 380

Trp Gln Ser Asn Gly Gln Pro Glu Pro Glu Ser Lys Tyr His Thr Thr
385                 390                 395                 400

Ala Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Thr Phe Thr Cys Ala
            420                 425                 430

Val Met His Glu Ala Leu Gln Asn His Tyr Thr Asp Leu Ser Leu Ser
            435                 440                 445

His Ser Pro Gly Lys
    450

<210> SEQ ID NO 23
<211> LENGTH: 23
<212> TYPE: PRT
<213> ORGANISM: Artificial Sequence
<220> FEATURE:
<223> OTHER INFORMATION: VL - FR1
```

```
<400> SEQUENCE: 23

Asp Ile Gln Met Thr Gln Ser Pro Ala Ser Leu Ser Leu Ser Gln Glu
1               5                   10                  15

Glu Lys Val Thr Ile Thr Cys
            20

<210> SEQ ID NO 24
<211> LENGTH: 23
<212> TYPE: PRT
<213> ORGANISM: Artificial Sequence
<220> FEATURE:
<223> OTHER INFORMATION: VL2 - FR1

<400> SEQUENCE: 24

Asp Ile Val Met Thr Gln Ser Pro Ala Ser Leu Ser Leu Ser Gln Glu
1               5                   10                  15

Glu Lys Val Thr Ile Thr Cys
            20

<210> SEQ ID NO 25
<211> LENGTH: 15
<212> TYPE: PRT
<213> ORGANISM: Artificial Sequence
<220> FEATURE:
<223> OTHER INFORMATION: VL - FR2

<400> SEQUENCE: 25

Trp Tyr Gln Gln Lys Pro Gly Gln Ala Pro Lys Leu Leu Ile Tyr
1               5                   10                  15

<210> SEQ ID NO 26
<211> LENGTH: 32
<212> TYPE: PRT
<213> ORGANISM: Artificial Sequence
<220> FEATURE:
<223> OTHER INFORMATION: VL - FR3

<400> SEQUENCE: 26

Gly Val Pro Ser Arg Phe Ser Gly Ser Gly Ser Gly Thr Glu Tyr Ser
1               5                   10                  15

Leu Thr Ile Asn Ser Leu Glu Ser Glu Asp Val Ala Val Tyr Phe Cys
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: VL2 - FR3

<400> SEQUENCE: 27

Gly Val Pro Ser Arg Phe Ser Gly Ser Gly Ser Gly Thr Glu Phe Ser
1               5                   10                  15

Leu Thr Ile Ser Ser Leu Glu Pro Glu Asp Val Ala Val Tyr Tyr Cys
            20                  25                  30

<210> SEQ ID NO 28
<211> LENGTH: 10
<212> TYPE: PRT
<213> ORGANISM: Artificial Sequence
<220> FEATURE:
<223> OTHER INFORMATION: VL - FR4

<400> SEQUENCE: 28
```

```
Phe Gly Ala Gly Thr Lys Val Glu Leu Lys
1               5                   10

<210> SEQ ID NO 29
<211> LENGTH: 30
<212> TYPE: PRT
<213> ORGANISM: Artificial Sequence
<220> FEATURE:
<223> OTHER INFORMATION: VH - FR1

<400> SEQUENCE: 29

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: VH - FR2

<400> SEQUENCE: 30

Trp Val Arg Gln Ala Leu Gly Arg Gly Leu Glu Trp Val Gly
1               5                   10

<210> SEQ ID NO 31
<211> LENGTH: 32
<212> TYPE: PRT
<213> ORGANISM: Artificial Sequence
<220> FEATURE:
<223> OTHER INFORMATION: VH - FR3

<400> SEQUENCE: 31

Arg Leu Thr Ile Thr Arg Asp Thr Ser Lys Ser Thr Val Phe Leu Lys
1               5                   10                  15

Met His Ser Leu Gln Ser Glu Asp Thr Ala Thr Tyr Tyr Cys Ala Arg
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: VH2 - FR3

<400> SEQUENCE: 32

Arg Leu Thr Ile Thr Arg Asp Thr Ser Lys Ser Thr Val Phe Leu Gln
1               5                   10                  15

Met His Ser Leu Arg Ser Glu Asp Thr Ala Thr Tyr Tyr Cys Ala Arg
            20                  25                  30

<210> SEQ ID NO 33
<211> LENGTH: 11
<212> TYPE: PRT
<213> ORGANISM: Artificial Sequence
<220> FEATURE:
<223> OTHER INFORMATION: VH - FR4

<400> SEQUENCE: 33

Trp Gly Gln Gly Thr Leu Val Thr Val Ser Ser
1               5                   10
```